US006245337B1

(12) United States Patent
St. Geme, III et al.

(10) Patent No.: US 6,245,337 B1
(45) Date of Patent: *Jun. 12, 2001

(54) HAEMOPHILUS ADHERENCE AND PENETRATION PROTEINS

(75) Inventors: Joseph W. St. Geme, III, St. Louis, MO (US); Stanley Falkow, Portola Valley, CA (US)

(73) Assignees: Washington University, St. Louis, MO (US); The Board of Trustees of the Leland Stanford Junior University, Palo Alto, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/296,791

(22) Filed: Aug. 25, 1994

(51) Int. Cl.[7] ................................................. A61K 39/102

(52) U.S. Cl. ................................... 424/256.1; 424/190.1; 530/350; 435/69.1; 435/69.3

(58) Field of Search ............................ 424/190.1, 256.1; 530/350; 435/69.1, 69.3

(56) References Cited

FOREIGN PATENT DOCUMENTS

9011367 * 10/1990 (WO) ............................. C12P/21/02

OTHER PUBLICATIONS van Hom et al, The EMBO Journal 8: 3535–3540, 1989.*
Thomas et al, Infection & Immunity 58: 1909–1913, 1990.*
Guleg et al Infection & Immunity 44: 41–48, 1984.*
St. Geme et al Molecular Microbiology 14:217–233 1994.*
Houghten et al Vaccine 86, pp. 21–25, 1986.*
Lewin Science vol. 237, p. 1570 When Does Homology Mean Something Else? 1987.*
Reech et al, Cell vol. 50, p. 667 Homology in Proteins and Nucleic Acids: A Terminology Middle and a Way out, 1987.*
Pichichero, M.E., "Do Pili Play A Role In Pathogenicity of *Haemophilus Influenzae* Type B", *The Lancet*, 56(2) 960–962: (1982).
Bakaletz, L.O., et al., "Frequency of Fimbriation of nontypable *Haemophilus influenzae* and Its Ability To Adhere to Chinchilla and Human Respiratiory Epithelium", *Infection and Immunity*, 56(2): 331–335, (1988).
Marieke van Ham, S., et al., "Cloning and expression in *Escherichia coil* of *Haemophilus influenzae* fimbrial genes establishes adherence to oropharyngeal epithelial cells", *The EMBO Journal*, 8(11):3535–3540, (1989).

Barenkamp, S.J., et al., "Cloning Expression, and DNA Sequence Analysis of Genes Encoding Nontypeable *Haemophilus influenzae* High–Molecular–Weight Surface–Exposed Proteins Related to Filamentous Hemagglutinin of *Bordetella Pertussis*", *Infection and Immunity*, 60(4):1302–1313, (1992).
St. Geme, J.W., et al., "High–molecular–weight proteins of nontypable *Haemophilus influezae* mediate attachment to human epithelial cells", *Proc. Natl. Acad. Sci. USA*, 90:2875–2879, (1993).
St. Gemme, et al., "*Haemophilus Influenzae* Adheres to and Enters Cultured Human Epithelial Cells", *Infection and Immunity*, 58(12): 4036–4044, (1990).
St. Geme, J.W., "Surface Structures and Adherence Properties of Diverse Strains of *Haemophilus Influenzae* Biogroup Aegyptius", *Infection and Immunity*, 59(10):3366–3371, (1991).
Simon, D., et al., "*Escherichia coli* expressing a *Neisseria gonorrhoeae* opacity–associated outer membrane protein invade human cervical and endometrial epithelial cell lines", *Proc. Natl. Acad. Sci. USA*, 89:5512–5516, (1992).
Krivan, H.C., et al., "Many pulmonary pathogenic bacteria bind specifically to the carbohydrate sequence GalNAcβ1–4Gal found in some glycolipids", *Proc. Natl. Acad. Sci. USA*, 85:6157–6161, (1988).
Venkatesan, M.M., et al., "Characterization of invasion plasmid antigen genes (ipaBCD) from *Shigella flexneri*", *Proc. Natl. Acad. Sci. USA*, 85:9317–9321, (1988).
Benz, I., et al., "AIDA–I, the adhesin involved in diffuse adherence of the diarrhoeagenic *Escherichia coli* strain 2787 (0126:H27), is synthesized via a precursor molecule", *Molecular Microbiology*, 6(11):1539–1546, (1992).
Isberg, R.R.,et al. "Identification of Invasin: A Protein That Allows Enteric Bacteria to Penetrate Cultured Mammalian Cells", *Cell*, 60:769–778, (1987).
Koomey, J.M., et al., "Nucleotide Sequence Homology Between the Immunoglubulin A1 Protease Genes of *Neisseria gonorrhoeae, Neisseria meningitidis,* and *Haemophilus influenzae*" Infection and Immunity, 43(1):101–107, (1984).
Forsgren, J., et al., "*Haemophilus influenzae* Resides and Multiplies Intracellulary in Human Adenoid Tissue as Demonstrated by In Situ Hybridization and Bacterial Viability Assay", *Infection and Immunity*, 62(2):673–679, (1994).
Pohlner, J., et al., "Gene Structure and extracellular secretion of *Neisseria gonorrhoeae* IgA protease", *Nature*, 325(29):458–462, (1987).
Provence, D.L., et al., "Isolation and Characterization of a Gene Involved in Hemagglutination by an Avian Pathogenic *Escherichia coli* Strain", *Infection and Immunity*, 62(4):1369–1380, (1994).

(List continued on next page.)

Primary Examiner—Jennifer Graser
(74) Attorney, Agent, or Firm—Richard F. Trecartin; Flehr Hohbach Test Albritton & Herbert LLP

(57) ABSTRACT

Haemophilus adhesion and penetration proteins, nucleic acids, vaccines and monoclonal antibodies are provided.

5 Claims, 23 Drawing Sheets

OTHER PUBLICATIONS

Poulsen, K., et al., "Cloning and Sequencing of the Immunoglobulin A1 Protease Gene (iga) of *Haemophilus influenzae* Serotype b", *Infection and Immunity*, 57(10):3097–3105, (1989).

Poulsen, K., et al., "A Comparative Genetic Study of Serologically Distinct *Haemophilus influenzae* Type 1 Immunoglobulin A1 Proteases", *Journal of Bacteriology*, 174(9):2913–2921, (1992).

Uphoff, T.S., et al., "Nucleotide Sequencing of the *Proteus mirabilis* Calcium–Independent Homelysin Genes (hpmA and hpmB) Reveals Sequence Similarity with the *Serratia marcescens* Hemolysin Genes (sh1A and sh1B)", *Journal of Bacteriology*, 172(3):1206–1216, (1990).

Brennan, M.J., et al., "Identification of a 69–Kilodalton Nonfimbrial Protein As an Agglutinogen of *Bordetella pertussis*", *Infection and Immunity*, 56(12):3189–3195, (1988).

Charles, I.G., et al., "Molecular cloning and characterization of protective outer membrane protein p. 69 from *Bordetella pertussis*", *Proc. Natl. Acad. Sci. USA*, pp. 86:3554–3558 (1989).

Leininger, E., et al., "Comparative Roles of the Arg–Gly–Asp Sequence Present in the *Bordetella pertussis* Adhesins Pertactin and Filamentous Hemagglutinin", *Infection and Immunity*, 60(6):2380–2385, (1992).

Leininger, E., et al., "Pertactin, an Arg–Gly–Asp–containing *Bordetella pertussis* surface protein that promotes adherence of mammalian cells", *Proc. Natl. Acad. Sci., USA.*, 88:345–349, (1991).

Ewanowich, C.A., et al., "Invasion of HeLa 229 Cells by Virulent *Bordetella pertussis*", *Infection and Immunity*, 57(9):2698–2704, (1989).

Thomas, W.R., et al., "Expression in *Escherichia coli* of a High–Molecular–Weight Protective Surface Antigen Found in Nontypeable and Type b *Haemophilus influenzae*," *Infection and Immunity*, 58(6):1909–1913.

* cited by examiner

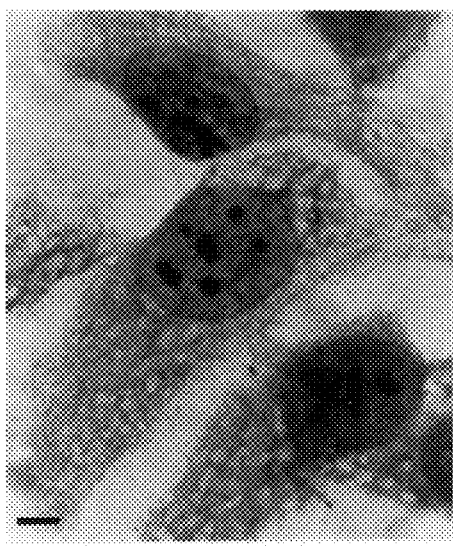 
FIG._1A        FIG._1B

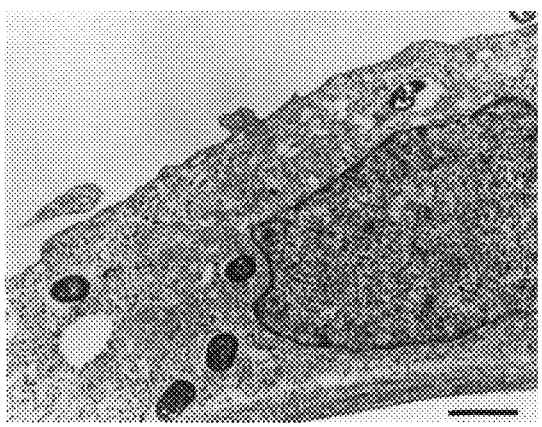 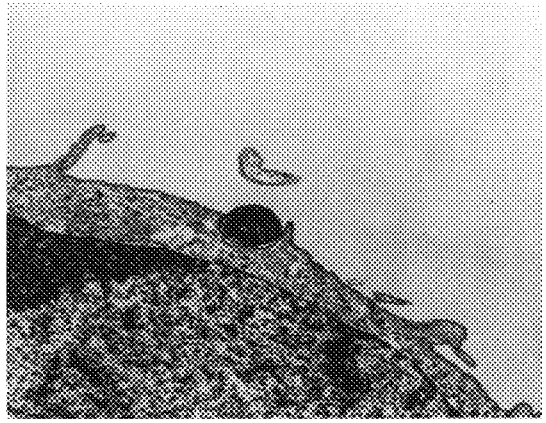
FIG._2A  FIG._2B

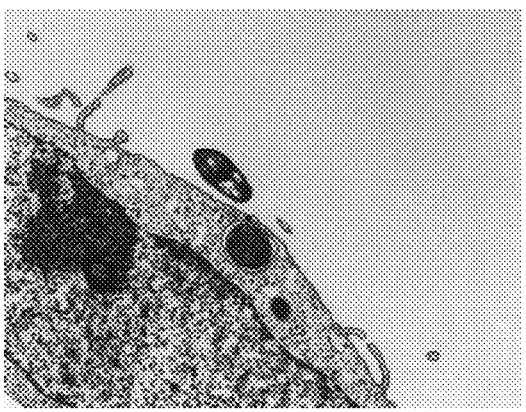 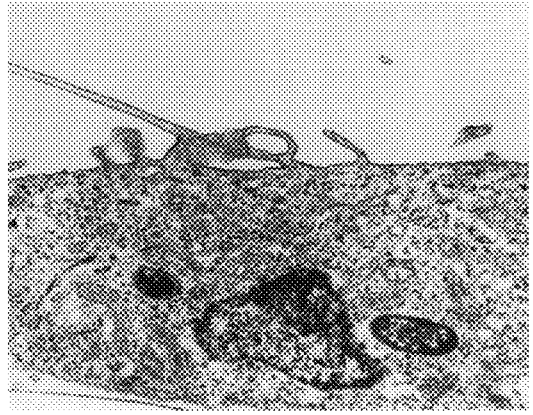
FIG._2C  FIG._2D

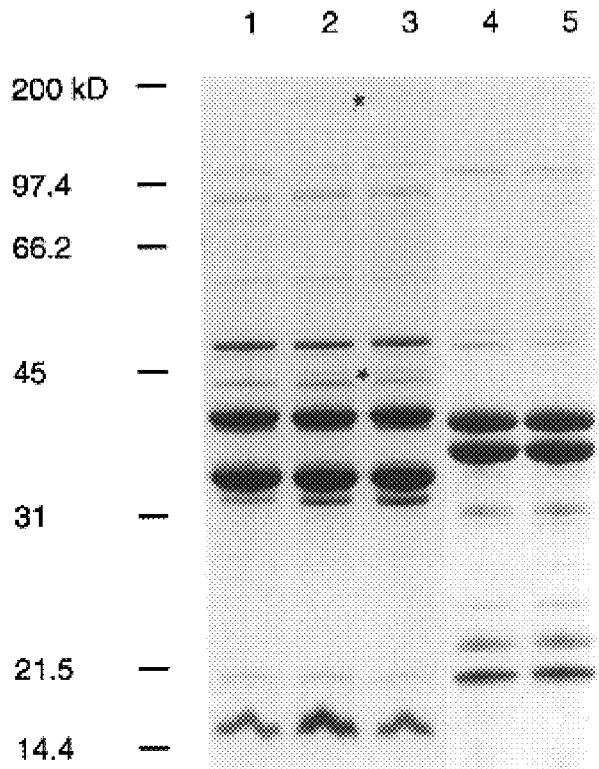
FIG._3
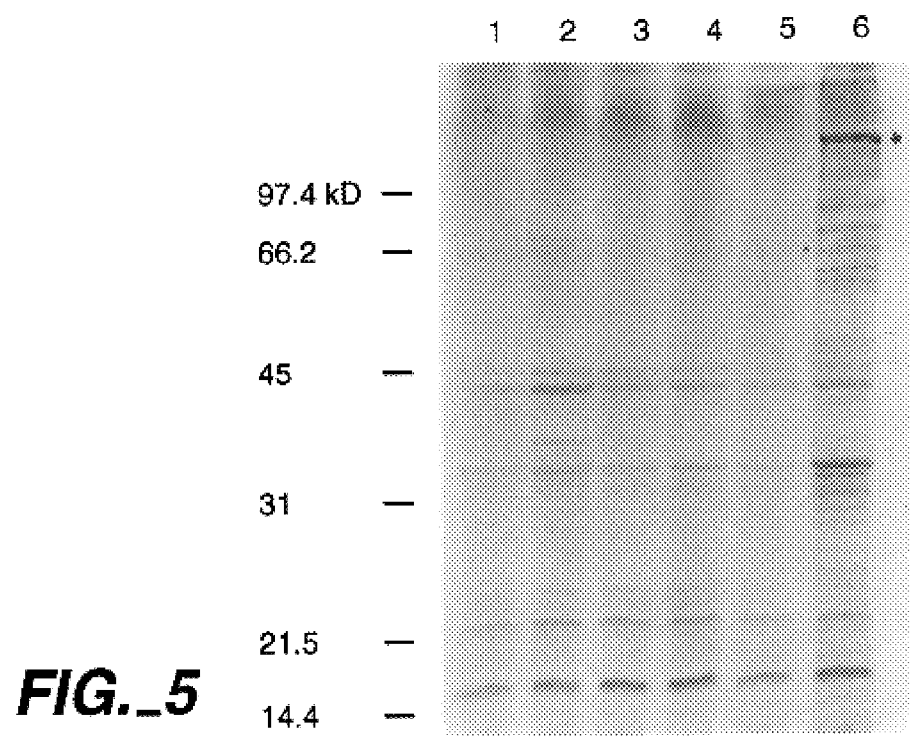
FIG._5

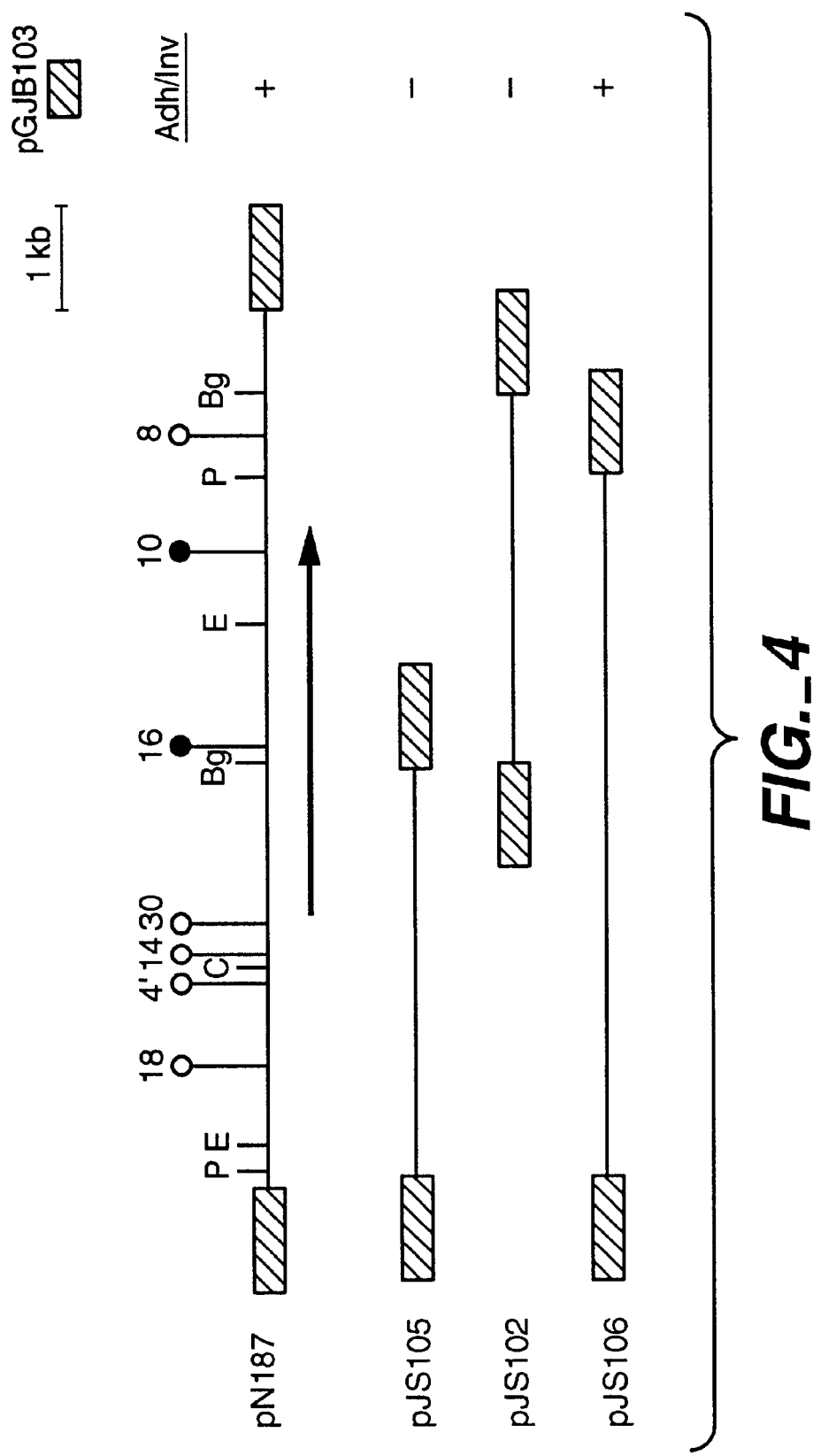
FIG._4

```
         10                  30                  50                      70                   90
TCAATAGTCGTTTAACTAGTATTTTTTAATACGAAAAATTACTTAATAAACATTATGAAAAAAACTGTATTCGTCTTAATTTT
         ___                                                            M  K  K  T  V  F  R  L  N  F
         -35                         -10
          110                 130                 150                 170
TTAACCGCTTGCATTTCATTAGGGATAGTATCGCAAGCTGTGGGCTGGTCACACTTATTTTGGGATTGATTACCAATATTATCGTGATTTT
 L  T  A  C  I  S  L  G  I  V  S  Q  A  W  A  G  H  T  Y  F  F  G  I  D  Y  Q  Y  Y  R  D  F
          190                 210                 230                 250                 270
GCCGAGAATAAAGGGAAGTTCACAGTTGGGGCTCAAAATATTAAGGTTTATAACAAACAAGGGCAATTAGTTGGCACATCAATGACAAAA
 A  E  N  K  G  K  F  T  V  G  A  Q  N  I  K  V  Y  N  K  Q  G  Q  L  V  G  T  S  M  T  K
          290                 310                 330                 350
GCCCCGATGATTGATTTTTCTGTAGTGTCACGTAACGGCGTGGCAGCCTTGGTTGAAATCAATATATTGTGAGCGTGGCACATAACGTA
 A  P  M  I  D  F  S  V  V  S  R  N  G  V  A  A  L  V  E  N  Q  Y  I  V  S  V  A  H  N  V
          370                 390                 410                 430                 450
GGATATACAGATGTTGATTTTGGTGCAGAGGGAAACAACCCCGATCAACATCGTTTTACTTATAAGATTGTAAAACGAAATAACTACAAA
 G  Y  T  D  V  D  F  G  A  E  G  N  N  P  D  Q  H  R  F  T  Y  K  I  V  K  R  N  N  Y  K
          470                 490                 510                 530
AAAGATAATTTACATCCTTATGAGGACGATTACCATAATCCACGATTACATAAATTCGTTACAGAAGCGGCTCCAATTGATATGACTTCG
 K  D  N  L  H  P  Y  E  D  D  Y  H  N  P  R  L  H  K  F  V  T  E  A  A  P  I  D  M  T  S
          550                 570                 590                 610                 630
AATATGAATGGCAGTACTTATTCAGATAGAACAAAATATCCAGAACGTGTTCGTATCGGCTGTGACGGCAGTTTGGCCGAAATGATCAA
 N  M  N  G  S  T  Y  S  D  R  T  K  Y  P  E  R  V  R  I  G  S  G  R  Q  F  W  R  N  D  Q
          650                 670                 690                 710
GACAAAGGCGACCAAGTTGCCGGTGCATATCATTATCTGACAGCTGGCAATACACACAATCAGCGTGGAGCAGGTAATGGATATTCGTAT
 D  K  G  D  Q  V  A  G  A  Y  H  Y  L  T  A  G  N  T  H  N  Q  R  G  A  G  N  G  Y  S  Y
```

FIG._6A

```
        730                    750                    770                    790                    810
TTGGGAGGCGATGTTCGTAAAGCGGGAGAATATGGTCCATTACCGATTGCAGGCTCAAAGGGGACAGTGGTTCTCCGATGTTTATTTAT
 L  G  G  D  V  R  K  A  G  E  Y  G  P  L  P  I  A  G  S  K  G  D  S  G  S  P  M  F  I  Y
        830                    850                    870                    890
GATGCTGAAAAACAAAAATGGTTAATTAATGGGATATTACGGGAAGGCAACCCCTTTTGAAGGCAAAGAAAATGGGTTTCAATTGGTTCGC
 D  A  E  K  Q  K  W  L  I  N  G  I  L  R  E  G  N  P  F  E  G  K  E  N  G  F  Q  L  V  R
        910                    930                    950                    970                    990
AAATCTTATTTTGATGAAATTTTCGAAAGAGATTTACATACATCACTTTACACCCGAGCTGGTAATGGAGTGTACACAATTAGTGGAAAT
 K  S  Y  F  D  E  I  F  E  R  D  L  H  T  S  L  Y  T  R  A  G  N  G  V  Y  T  I  S  G  N
        1010                   1030                   1050                   1070
GATAATGGTCAGGGGTCTATAACTCAGAAATCAGGAATACCATCAGAAATAAAAATTACGTTAGCAAATATGAGTTTACCTTTGAAAGAG
 D  N  G  Q  G  S  I  T  Q  K  S  G  I  P  S  E  I  K  I  T  L  A  N  M  S  L  P  L  K  E
        1090                   1110                   1130                   1150                   1170
AAGGATAAAGTTCATAATCCTAGATATGACGGACCTAATATTTATTCTCCACGTTTAAACAATGGAGAAACGCTATATTTTATGGATCAA
 K  D  K  V  H  N  P  R  Y  D  G  P  N  I  Y  S  P  R  L  N  N  G  E  T  L  Y  F  M  D  Q
        1190                   1210                   1230                   1250
AAACAAGGATCATTAATCTTCGCATCTGACATTAACCAAGGGGCGGGGTGCTCTTTATTTTGAGGGTAATTTTACAGTATCTCCAAATTCT
 K  Q  G  S  L  I  F  A  S  D  I  N  Q  G  A  G  G  L  Y  F  E  G  N  F  T  V  S  P  N  S
        1270                   1290                   1310                   1330                   1350
AACCAAACTTGGCAAGGAGCTGGCATACATGTAAGTGAAAATAGCACCGTTACTTGGAAAGTAAATGGCGTTGGAACATGACTTTCT
 N  Q  T  W  Q  G  A  G  I  H  V  S  E  N  S  T  V  T  W  K  V  N  G  V  E  H  D  R  L  S
        1370                   1390                   1410                   1430
AAAATTGGTAAAGGAACATTGCACGTTCAAGCCAAAGGGGAAAATAAAGGTTCGATCAGCGGCGTAGGCGATGGTAAAGTCATTTTGGAGCAG
 K  I  G  K  G  T  L  H  V  Q  A  K  G  E  N  K  G  S  I  S  V  G  D  G  K  V  I  L  E  Q
```

*FIG._6B*

```
                    1450             1470              1490              1510              1530
CAGGCAGACGATCAAGGCAACAAACAAGCCTTTAGTGAAATTGGCTTGGTTAGCGGCAGAGGGACTGTTCAATTAAACGATGATAAACAA
 Q  A  D  D  Q  G  N  K  Q  A  F  S  E  I  G  L  V  S  G  R  G  T  V  Q  L  N  D  D  K  Q 1550             1570              1590              1610
TTTGATACCGATAAATTTTATTTCGGCTTTCGTGGTGGTCGCTTAGATCTTAACGGGCATTCATTAACCTTTAAACGTATCCAAAATACG
 F  D  T  D  K  F  Y  F  G  F  R  G  G  R  L  D  L  N  G  H  S  L  T  F  K  R  I  Q  N  T 1630             1650              1670              1690              1710
GACGAGGGGGCAATGATTGTGAACCATAATACAACTCAAGCCGCTAATGTCACTATTACTGGGAACGAAAGCATTGTTCTACCTAATGGA
 D  E  G  A  M  I  V  N  H  N  T  T  Q  A  A  N  V  T  I  T  G  N  E  S  I  V  L  P  N  G 1730             1750              1770              1790
AATAATATTAATAAACTTGATTACAGAAAAGAAATTGCCTACAACGGTTGGTTTGGCGAAACAGATAAAAATAAACACAATGGGCGATTA
 N  N  I  N  K  L  D  Y  R  K  E  I  A  Y  N  G  W  F  G  E  T  D  K  N  K  H  N  G  R  L 1810             1830              1850              1870              1890
AACCTTATTTATAAACCAACCACAGAAGATCGTACTTTGCTACTTTTATCAGGTGGTACAAATTTAAAAGGCGATATTACCCAAACAAAGGT
 N  L  I  Y  K  P  T  T  E  D  R  T  L  L  L  S  G  G  T  N  L  K  G  D  I  T  Q  T  K  G 1910             1930              1950              1970
AAACTATTTTTCAGCGGTAGACCGACCACCGCCACACGCCTACAATCATTTAAATAAACGTTGGTCAGAAATGGAAGGTATACCACAAGGCGAA
 K  L  F  F  S  G  R  P  T  P  H  A  Y  N  H  L  N  K  R  W  S  E  M  E  G  I  P  Q  G  E 1990             2010              2030              2050              2070
ATTGTGTGGGATCACGATTGGATCAACCGTACATTTAAAGCTGAAAACTTCCAAATTAAAGGCGGAAGTGCGGTTGTTTCTCGCAATGTT
 I  V  W  D  H  D  W  I  N  R  T  F  K  A  E  N  F  Q  I  K  G  G  S  A  V  V  S  R  N  V 2090             2110              2130              2150
TCTTCAATTGAGGGAAATTGGACAGTCAGCAATAAATGCCACATTTGGTGTGTGCCAAATCAACAAATACCATTTGCACGCGT
 S  S  I  E  G  N  W  T  V  S  N  N  A  N  A  T  F  G  V  V  P  N  Q  Q  N  T  I  C  T  R
```

FIG._6C

```
                        2190                    2210                    2230                    2250
         2170
TCAGATTGGACAGGATTAACGACTTGTCAAAAAGTGGATTAACCGATACAAAAGTTATTAATTCTATACCAAAAACACAAATCAATGGC
 S  D  W  T  G  L  T  T  C  Q  K  V  D  L  T  D  T  K  V  I  N  S  I  P  K  T  Q  I  N  G 2270                    2290                    2310                    2330
TCTATTAATTTAACTGATAATGCGAATGCGGCGAATGTTAAAGGTTTAGCAAAACTTAATGGCAATGTCACTTTAACAAATCACAGCCAATTT
 S  I  N  L  T  D  N  A  T  A  N  V  K  G  L  A  K  L  N  G  N  V  T  L  T  N  H  S  Q  F 2350                    2370                    2390                    2410                    2430
ACATTAAGCAACAATGCCACCCAAATATTCGACTTTCCGACAATTCAACTGCAACGGTGGATAATGCAAACTTGAACGGTAAT
 T  L  S  N  N  A  T  Q  I  F  D  F  P  T  I  Q  L  Q  R  W  I  M  Q  T  *  T  V  N 2450                    2470                    2490                    2510
GTGCATTTAACGGATTCAGCTCAATTTTCTTTAAAAACAGCCATTTTTCGCACCCAAATTCAGGGAGACAAAGGCACAACAGTGACGTTG
 V  H  L  T  D  S  A  Q  F  S  L  K  N  S  H  F  S  H  Q  I  Q  G  D  K  G  T  T  V  T  L 2530                    2550                    2570                    2590                    2610
GAAAATGCGACTTGGACAATGCCTAGCGATACTACATTGCAGAATTAACGCTAAATAACAGTACGATCACGTTAAATTCAGCTTATTCA
 E  N  A  T  W  T  M  P  S  D  T  T  L  Q  N  L  T  L  N  N  S  T  I  T  L  N  S  A  Y  S 2630                    2650                    2670                    2690
GCTAGCTCAAACAATACGCCACGTCGCCGTTCATTAGAGACGGAAACAACGCCAACATCGGCAGAACATCGTTTCAACACATTGACAGTA
 A  S  S  N  N  T  P  R  R  R  S  L  E  T  E  T  T  P  T  S  A  E  H  R  F  N  T  L  T  V 2710                    2730                    2750                    2770                    2790
AATGGTAAATTGAGTGGGCAAGGCACATTCCAATTTACTTCATCTTTATTTGGCTATAAAGCGGATAAAATTATCCAATGACGCT
 N  G  K  L  S  G  Q  G  T  F  Q  F  T  S  S  L  F  G  Y  K  S  D  K  L  K  L  S  N  D  A 2810                    2830                    2850                    2870
GAGGGCGATTACATATTATCTGTTCGCAACACAGGCAAAGAACCCTTGAGCAATTAACTTTGGTTGAAAGCAAAGATAATCAA
 E  G  D  Y  I  L  S  V  R  N  T  G  K  E  P  E  T  L  E  Q  L  T  L  V  E  S  K  D  N  Q

FIG._6D
```

```
      2890                    2910                    2930                    2950                    2970
CCGTTATCAGATAAGCTCAAATTTACTTTAGAAAATGACCACGTTGATGCAGGTGCATTACGTTATAAATTAGTGAAGAATGATGGCGAA
 P  L  S  D  K  L  F  T  L  E  N  D  H  V  D  A  G  A  L  R  Y  K  L  V  K  N  D  G  E 2990                    3010                    3030                    3050
TTCCGCTTGCATAACCCAATAAAAGAGCAGGAATTGCACAATGATTTAGTAAGAGCAAGCAGAACGAACATTAGAAGCAAACAA
 F  R  L  H  N  P  I  K  E  Q  E  L  H  N  D  L  V  R  A  E  Q  A  E  R  T  L  E  A  K  Q 3070                    3090                    3110                    3130                    3150
GTTGAACCGACTGCTAAAACACAAACAGGTGAGCCCAAAGTGCGGTCAAGAGAGCAGCAGAGCGCGTTTCCTGATACCCTGCCTGAT
 V  E  P  T  A  K  T  Q  T  G  E  P  P  K  V  R  S  R  R  A  A  R  A  A  F  P  D  T  L  P  D 3170                    3190                    3210                    3230
CAAAGCCTGTTAAACGCATTAGAAGCCAAACAAGCTGAACTGACTGCTGAAACACAAAAGTAAGGCAAAAACAAAAAGTGCGGTCA
 Q  S  L  L  N  A  L  E  A  K  Q  A  E  L  T  A  E  T  Q  K  S  K  A  K  T  K  K  V  R  S 3250                    3270                    3290                    3310                    3330
AAAAGAGCAGTGTTTTCTGATCCCCCTGCTTGATGATCAAAGCCCTGTTCGCATTAGAAGCCGCCACTTGAGGTTATTGATGCCCCACAGCAATCG
 K  R  A  V  F  S  D  P  L  L  D  D  Q  S  L  F  A  L  E  A  A  L  E  V  I  D  A  P  Q  Q  S 3350                    3370                    3390                    3410
GAAAAAGATCGTCTAGCTCAAGAAGAAGCGGAAAAAGAAGCTGATCAGCCCGTTATTCAAATAGTGCGTTATCAGAA
 E  K  D  R  L  A  Q  E  E  A  E  K  Q  R  K  Q  D  L  I  S  R  Y  S  N  S  A  L  S  E 3430                    3450                    3470                    3490                    3510
TTATCTGCAACAGTAAATAGTATGCTTTCTGTTCAAGATGAATTAGATCGTCTTTTTGTAGATCAAGCACAATCTGCCGTGTGGACAAAT
 L  S  A  T  V  N  S  M  L  S  V  Q  D  E  L  D  R  L  F  V  D  Q  A  Q  S  A  V  W  T  N 3530                    3550                    3570                    3590
ATCGCACAGGATAAAAGACGCTATGATTCCTGATGCGTTCCGTGCTTATCAGCAGCAGAAAACGAACTTACGTCAAATTGGGGTGCAAAAA
 I  A  Q  D  K  R  R  Y  D  S  D  A  F  R  A  Y  Q  Q  Q  K  T  N  L  R  Q  I  G  V  Q  K
```

*FIG._6E*

```
                3630                    3650                    3670                    3690
GCCTTAGCTAATGGACGAATTGGGGCAGTTTTCTCGCATAGCCGTTCAGATAATACCTTTGATGAACAGGTTAAAAATCACGCGACATTA
 A  L  A  N  G  R  I  G  A  V  F  S  H  S  R  S  D  N  T  F  D  E  Q  V  K  N  H  A  T  L
      3710                    3730                    3750                    3770
ACGATGATGTCGGGTTTTGCCCAATATCAATGGGGCGATTTACAATTTGGTGTAAACGTGGGAACGGGAATCAGTGCGAGTAAAATGGCT
 T  M  M  S  G  F  A  Q  Y  Q  W  G  D  L  Q  F  G  V  N  V  G  T  G  I  S  A  S  K  M  A
      3790                    3810                    3830                    3850                    3870
GAAGAACAAAGCCCGAAAAATTCATCCACGAAAAGCGATAAATTATGGCGTGAATGCAAGTTATCAGTTCCGTTTAGGGCAATTGGGCATTCAG
 E  E  Q  S  R  K  I  H  R  K  A  I  N  Y  G  V  N  A  S  Y  Q  F  R  L  G  Q  L  G  I  Q
      3890                    3910                    3930                    3950
CCTTATTTTGGAGTTAATCGCTATTTTATTGAACGTGAAAATTATCAATCTGAGGAAGTGAGAGTGAAAACGCCTAGCCTTGCATTTAAT
 P  Y  F  G  V  N  R  Y  F  F  I  E  R  E  N  Y  Q  S  E  E  V  R  V  K  T  P  S  L  A  F  N
      3970                    3990                    4010                    4030                    4050
CGCTATAATGCTGGCATTCGAGTTGATTATACATTTACTCCGACAGATAATATCAGCGTTAAGCCTTATTTCTTCGTCAATTATGTTGAT
 R  Y  N  A  G  I  R  V  D  Y  T  F  T  P  T  D  N  I  S  V  K  P  Y  F  F  V  N  Y  V  D
      4070                    4090                    4110                    4130
GTTTCAAACGCTAACGTACAAACCACGGTAAATCTCACGGTGTTGCAACAACCATTTGGACGTTATTGGCAAAAAGAAGTGGGATTAAAG
 V  S  N  A  N  V  Q  T  T  V  N  L  T  V  L  Q  Q  P  F  G  R  Y  W  Q  K  E  V  G  L  K
      4150                    4170                    4190                    4210                    4230
GCAGAAATTTTACATTTCCAAATTTCCGCTTTTATCTCAAAATCTCAAGGTTCACAAGTTCACAACTCGGCAAACAGCAAAATGTGGGCGTGAAATTG
 A  E  I  L  H  F  Q  I  S  A  F  I  S  K  S  Q  G  S  Q  L  G  K  Q  Q  N  V  G  V  K  L
      4250                    4270                    4290                    4310
GGCTATCGTTGTTGGTAAAATCAACACATAATTTTATCGTTTATTGATAAACAAGGTGGGTCAGATCAGATCCCACCTTTTTTATTCCAATAAT
 G  Y  R  W  *
```

```
                1                                                                    50
Hap             MKKTVFRLNF  LTACISLGIV  SQAWAGHTYF  GIDYQYYRDF  AENKGKFTVG
HK368IGA        MLNKKFKLNF  IALTVAYALT  PYTEAALVRD  DVDYQIFRDF  AENKGKFSVG
HK393IGA        MLNKKFKLNF  IALTVAYALT  PYTEAALVRD  DVDYQIFRDF  AENKGKFSVG
HK715IGA        MLNKKFKLNF  IALTVAYALT  PYTEAALVRD  DVDYQIFRDF  AENKGKFSVG
HK61IGA         MLNKKFKLNF  IALTVAYALT  PYTEAALVRD  DVDYQIFRDF  AENKGKFSVG
Consensus       M----F-LNF  --------    ------A---  --DYQ---RDF  AENKG-F-VG 51                                                                   100
Hap             AQNIKVYNKQ  GQLVGTSMTK  A.PMIDFSVV  SRNG.VAALV  ENQYIVSVAH
HK368IGA        ATNVLVKDKN  NKDLGTALPN  GIPMIDFSVV  DVDKRIATLI  NPQYVVGVKH
HK393IGA        ATNVEVRDKN  NRPLGNVLPN  GIPMIDFSVV  DVDKRIATLV  NPQYVVGVKH
HK715IGA        ATNVEVRDKN  NHSLGNVLPN  GIPMIDFSVV  DVDKRIATLI  NPQYVVGVKH
HK61IGA         ATNVEVRDKK  NQSLGSALPN  GIPMIDFSVV  DVDKRIATLV  NPQYVVGVKH
Consensus       A-N--V--K-  -----G----  --PMIDFSVV  ----A-L---  --QY-V-V-H 101                                                                  150
Hap             .....NVGY  TDVDFGAEGN  NPDQHR....  ..FTYKIVKR  NNY.......
HK368IGA        VSNGVSELHF  GNLNGNMNNG  NAKAHRDVSS  EENRYFSVEK  NEYPTKLNGK
HK393IGA        VSNGVSELHF  GNLNGNMNNG  NAKAHRDVSS  EENRYYTVEK  NEYPTKLNGK
HK715IGA        VSNGVSELHF  GNLNGNMNNG  NDKSHRDVSS  EENRYFSVEK  NEYPTKLNGK
HK61IGA         VSNGVSELHF  GNLNGNMNNG  NAKSHRDVSS  EENRYYTVEK  NEYPTKLNGK
Consensus       ----------  ----------  N---HR----  ----Y--V--  N---------

151                                                                  200
Hap             ...KKDNLH  PYEDDYHNPR  LHKFVTEAAP  IDM.TSNMNG  STYSDRTKYP
HK368IGA        TVTTEDQ.TQ  KRREDYYMPR  LDKFVTEVAP  IEASTASSDA  GTYNDQNKYP
HK393IGA        AVTTEDQ.AQ  KRREDYYMPR  LDKFVTEVAP  IEASTDSSDA  GTYNNKDKYP
HK715IGA        AVTTEDQ.TQ  KRREDYYMPR  LDKFVTEVAP  IEASTASSDA  GTYNDQNKYP
HK61IGA         FTTKEEQDAQ  KRREDYYMPR  LDKFVTEVAP  IEASTANNNK  GEYNNSDKYP
Consensus       ----------  ---DY--PR  L-KFVTE-AP  I---T-----  --Y----KYP
```

```
           201
Hap        ERVRIGSGRQ F.........  ..........  ......WRNDQ DKGDQVAGAY
HK368IGA   AFVRLGSGSQ FIYKKGDNYS  LIL.......N NH....EVGG  NNLKLVGDAY
HK393IGA   YFVRLGSGTQ FIYENGTRYE  LWL.......G KEGQKSDAGG  YNLKLVGNAY
HK715IGA   AFVRLGSGSQ FIYKKGDNYS  LIL.......N NH....EVGG  NNLKLVGDAY
HK61IGA    AFVRLGSGSQ FIYKKGSRYQ  LILTEKDKQG  NLLRNWDVGG  DNLELVGNAY
Consensus  --VR-GSG-Q F---------  ----------  ----------  ----V--AY
                                                              250

251
Hap        HYLTAGNTHN ORGAGNGYSY  LGG......D  VRKAGEYGPL  PIAGSKGDSG
HK368IGA   TYGIAGTPYK VNHENNGLIG  FGNSKEEHSD  PKGILSQDPL  TNYAVLGDSG
HK393IGA   TYGIAGTPYE VNHENDGLIG  FGNSNNEYIN  PKEILSKKPL  TNYAVLGDSG
HK715IGA   TYGIAGTPYK VNHENNGLIG  FGNSKEEHSD  PKGILSQDPL  TNYAVLGDSG
HK61IGA    TYGIAGTPYK VNHENNGLIG  FGNSKEEHSD  PKGILSQDPL  TNYAVLGDSG
Consensus  -Y--AG---- ------G---  ----G-----  ------PL--  ----GDSG
                                                              300

301
Hap        SPMFIYDAEK QKWLINGILR  EGNPFEGKEN  GFQLVRKSYF  D.EIFERDLH
HK368IGA   SPLFVYDREK GKWLFLGSYD  FWAGYN....  ....KKSWQ   EWNIYKSQFT
HK393IGA   SPLFVYDREK GKWLFLGSYD  YWAGYN....  ....KKSWQ   EWNIYKPEFA
HK715IGA   SPLFVYDREK GKWLFLGSYD  FWAGYN....  ....KKSWQ   EWNIYKPEFA
HK61IGA    SPLFVYDREK GKWLFLGSYD  FWAGYN....  ....KKSWQ   EWNIYKHEFA
Consensus  SP-F-YD-EK -KWL--G---  ----------  -----KS---  ----I----
                                                              350

351
Hap        TSLYTRAGNG VYTISGNDNG  QGSITQKSGI  PSEIKITLAN  MSLPLKEKDK
HK368IGA   KDVLNKDSAG SLIGSKTDYS  WSSNGKTSTI  TGGEK....S  LNVDLAD...
HK393IGA   EKIYEOYSAG SLIGSKTDYS  WSSNGKTSTI  TGGEK....S  LNVDLAD...
HK715IGA   KTVLDKDTAG SLTGSNTQYN  WNPTGKTSVI  SNGSE....S  LNVDLFD...
HK61IGA    EKIYQQYSAG SLTGSNTQYT  WQATGSTSTI  TGGGE....P  LSVDLTD...
Consensus  --------G- -------S--  ----------  ----S-I---  ----L----
                                                              400
```

FIG._7B

```
              401
Hap         VHNPRYDGPN IYSPRLNNGE TLYFMDQKQG SLIFASDINQ GAGGLYFEGN
HK368IGA    .......GKD ....KPNHGK SVTFEG...SG TLTLNNNIDQ GAGGLFFEGD
HK393IGA    .......GKD ....KPNHGK SVTFEG...SG TLTLNNNIDQ GAGGLFFEGD
HK715IGA    .....SSQD  TDSKKNNHGK SVTLRG...SG TLTLNNNIDQ GAGGLFFEGD
HK61IGA     .......GKD ....KPNHGK SITLKG...SG TLTLNNHHDQ GAGGLFFEGD
Consensus   ---------- -------N-G ---------G -L------I-Q GAGGL-FEG-
                                                              450

451
Hap         FTVSPNSNQ. TWQGAGIHVS ENSTVTWKVN GVEHDRLSKI GKGTLHVQAK
HK368IGA    YEVKGTSDNT TWKGAGVSVA EGKTVTWKVH NPQYDRLAKI GKGTLIVEGT
HK393IGA    YEVKGTSDNT TWKGAGVSVA EGKTVTWKVH NPQYDRLAKI GKGTLIVEGT
HK715IGA    YEVKGTSDST TWKGAGVSVA DGKTVTWKVH NPKSDRLAKI GKGTLIVEGK
HK61IGA     YEVKGTSDST TWKGAGVSVA DGKTVTWKVH NPKYDRLAKI GKGTLVVEGK
Consensus   --V----S-- TW-GAG--V- ---TVTWKV- ----DRL-KI GKGTL-V---
                                                              500

501
Hap         GENKGSISVG DGKVILEQQA DDQGNKQAFS EIGLVSGRGT VQLNDDKQFD
HK368IGA    GDNKGSLKVG DGTVILKQQT NGSGQ.HAFA SVGIVSGRST LVLNDDKQVD
HK393IGA    GDNKGSLKVG DGTVILKQQT NGSGQ.HAFA SVGIVSGRST LVLNDDKQVD
HK715IGA    GENKGSLKVG DGTVILKQQA DANNKVKAFS QVGIVSGRST VVLNDDKQVD
HK61IGA     GKNEGLLKVG DGTVILKQKA DANNKVQAFS QVGIVSGRST LVLNDDKQVD
Consensus   G-N-G---VG DG-VIL-Q-- -------AF- --G-VSGR-T --LNDDKQ-D
                                                              550

551
Hap         TDKFYFGFRG GRLDLNGHSL TFKRIQNTDE GAMIVNHNTT QAANVTITGN
HK368IGA    PNSIYFGFRG GRLDLNGNSL TFDHIRNIDD GARLVNHNMT NASNITITGE
HK393IGA    PNSIYFGFRG GRLDLNGNSL TFDHIRNIDD GARLVNHSTS KHSTVTITGD
HK715IGA    PNSIYFGFRG GRLDANGNNL TFEHIRNIDD GARLVNHNTS KTSTVTITGE
HK61IGA     PNSIYFGFRG GRLDLNGNSL TFDHIRNIDD GARVVNHNMT NTSNITITGE
Consensus   ----YFGFRG GRLD-NG--L TF---I-N-D- GA--VNH--- -----TITG-
                                                              600
```

FIG. 7C

```
            601
Hap         ESIVLPNG.. .......... .......... .......... ..........
HK368IGA    SLITDPNTIT PYNIDAPDED NPYAFRRIKD GGQLYLNLEN YTYYALRKGA
HK393IGA    NLITDPNNVS IYYVKPLEDD NPYAIRQIKY GYQLYFNEEN RTYYALKKDA
HK715IGA    SLITDPNTIT PYNIDAPDED NPYAFRRIKD GGQLYLNLEN YTYYALRKGA
HK61IGA     SLITNPNTIT SYNIEAQDDD HPLRIRSIPY R.QLYFNQDN RSYYTLKKGA
Consensus   --I---PN--- ---------- ---------- ---------- ----------
                                                              650

651                                                700
Hap         .......... .......... .......... ..........N NINKLDYRKE
HK368IGA    STRSELPKNS GESNENWLYM GKTSDEAKRN VMHINNERM   IAYNGWFGET
HK393IGA    SIRSEFPQNR GESNNSWLYM GTEKADAQKN AMNHINNERM   NGFNGYFGEE
HK715IGA    STRSELPKNS GESNENWLYM GKTSDEAKRN VMNHINNERM   NGFNGYFGEE
HK61IGA     STRSELPQNS GESNENWLYM GRTSDEAKRN VMNHINNERM   NGFNGYFGEE
Consensus   ---------- ---------- ---------N ----N-----   ---NG-FGE- 701                                                750
Hap         D.KNKHNGRL NLIYKPTTED RTLLLSGGTN LKGDITQTKG KLFFSGRPTP
HK368IGA    EGK..NNGNL NVTFKGKSEQ NRFLLTGGTN LNGDLTVEKG TLFLSGRPTP
HK393IGA    EGK..NNGNL NVTFKGKSEQ NRFLLTGGTN LNGDLNVQQG TLFLSGRPTP
HK715IGA    EGK..NNGNL NVTFKGKSEQ NRFLLTGGTN LNGDLKVEKG TLFLSGRPTP
HK61IGA     ETKATQNGKL NVTFNGKSDQ NRFLLTGGTN LNGDLNVEKG TLFLSGRPTP
Consensus   --K---NG-L N--------- ---LL-GGTN L--GD------G -LF-SGRPTP 751                                                800
Hap         HAYNHLNKRW SEMEG...IPQ GEIVWDHDWI NRTFKAENFQ IKGGSAVVS.
HK368IGA    HARDIAGISS TKKDPHFAEN NEVVVEDDWI NRNFKATTMN VTGNASLYSG
HK393IGA    HARDIAGISS TKKDSHFSEN NEVVVEDDWI NRNFKATNIN VTNNATLYSG
HK715IGA    HARDIAGISS TKKDQHFAEN NEVVVEDDWI NFNERATNIN VTNNATLYSG
HK61IGA     HARDIAGISS TKKDPHFTEN NEVVVEDDWI NRNFKATTMN VTGNASLYSG
Consensus   HA-------- ---------- ---E-V---DWI NR-FKA---- ------S---
```

FIG. 7D

```
              801
Hap           RNVSSIEGNW TVSNNANATF GVVPNQQNTI CTRSDWTGLT TCQKVDLTDT   850
HK368IGA      RNVANITSNI TASNKAQVHI GY..KTGDTV CVRSDYTGYV TCTTDKLSD.
HK393IGA      RNVESITSNI TASNNAKVHI GY..KAGDTV CVRSDYTGYV TCTTDKLSD.
HK715IGA      RNVANITSNI TASDNAKVHI GY..KAGDTV CVRSDYTGYV TCTTDKLSD.
HK61IGA       RNVANITSNI TASNNAQVHI GY..KTGDTV CVRSDYTGYV TCHNSNLSE.
Consensus     RNV---I--N T-S--A---- G-------T- C-RSD-TG-- TC----L---
                                                             *
              851
Hap           KVINSIPKTQ INGSINLTDN ATANVRGLAK LNGNVTLTNH SQFTLSNNAT   900
HK368IGA      KALNSFNPTN LRGNVNLTES A......... .......... ..........
HK393IGA      KALNSFNPTN LRGNVNLTES A......... .......... ..........
HK715IGA      KALNSFNATN VSGNVNLSGN A......... .......... ..........
HK61IGA       KALNSFNPTN LRGNVNLTEN A......... .......... ..........
Consensus     K--NS---T- --G--NL--- A--------- ---------- ----------
                                  *

901
Hap           QIGNIRLSDN STATVDNANL NGNVHLTDSA QFSLKNSHFS HQIQGDKGTT   950
HK368IGA      .......... .NFVLGKANL FGTIQSRGNS QVRLT..... ..........
HK393IGA      .......... .NFVLGKANL FGTIQSRGNS QVRLT..... ..........
HK715IGA      .......... .NFVLGKANL FGTISGTGNS QVRLT..... ..........
HK61IGA       .......... .SFTLGKANL FGTIQSIGTS QVNLK..... ..........
Consensus     ---------- ------ANL -G-------- Q--L------ ----------

951
Hap           VTLENATWTM PSDTTLQNLT LNNSTITLNS AYSASSNNTP RRRSLETETT   1000
HK368IGA      ...ENSHWHL TGNSDVHQLD LANGHIHLNS ADNSNNVTK. ..........
HK393IGA      ...ENSHWHL TGNSDVHQLD LANGHIHLNS ADNSNNVTK. ..........
HK715IGA      ...ENSHMHL TGDSNVNQLN LDKGHIHLNA QNDANKVTT. ..........
HK61IGA       ...ENSHWHL TGNSNVNQLN LTNGHIHLNA QNDANKVTT. ..........
Consensus     ---EN--W-- ---------L L---I--LN- ---------- ----------
```

FIG. 7E

```
            1001                                                      1050
Hap         PTSAEHRFNT  LTVNGKLSGQ  GTFQFTSSLF  GYKSDKLKLS  NDAEGDYILS
HK368IGA    ........YNT LTVNS.LSGN  GSFYYLTDLS  NKQGDKVVVT  KSATGNFTLQ
HK393IGA    ........YNT LTVNS.LSGN  GSFYYLTDLS  NKQGDKVVVT  KSATGNFTLQ
HK715IGA    ........YNT LTVNS.LSGN  GSFYYLTDLS  NKQGDKVVVT  KSATGNFTLQ
HK61IGA     ........YNT LTVNS.LSGN  GSFYYWVDFT  NNKSNKVVVN  -----K----
Consensus   -------NT   LTVN--LSG-  G-F-------  ----------  --A--G---L-

1051                                                      1100
Hap         VRNTGKEPET  LEQLTLVESK  DNQPLSDKLK  FTLENDHVDA  GALRYKLVKN
HK368IGA    VADKTGEPNH  .NELTLFDAS  KAQR..DHLN  VSLVGNTVDL  GAWKYKLRNV
HK393IGA    VADKTGEPNH  .NELTLFDAS  KAQR..DHLN  VSLVGNTVDL  GAWKYKLRNV
HK715IGA    VADKTGEPTK  .NELTLFDAS  NATR..NNLN  VSLVGNTVDL  GAWKYKLRNV
HK61IGA     VADKTGEPNH  .NELTLFDAS  NATR..NNLE  VTLANGSVDR  GAWKYKLRNV
Consensus   V------EP--  ---LTL----  --------    --L----VD--  GA---YKL---

1101                                                      1150
Hap         DGEFRLHNPI  KEQELHNDLV  ..........  ..........  ..........
HK368IGA    NGRYDLYNP.  .EVEKRNQTV  DTTNITTPNN  IQADVPSVPS  NNEEIARVDE
HK393IGA    NGRYDLYNP.  .EVEKRNQTV  DTTNITTPNN  IQADVPSVPS  NNEEIARVDE
HK715IGA    NGRYDLYNP.  .EVEKRNQTV  DTTNITTPNN  IQADVPSVPS  NNEEIARV.E
HK61IGA     NGRYDLYNP.  .EVEKRNQTV  DTTNITTPND  IQADAPSAQS  NNEEIARV.E
Consensus   -G----L-NP-  -E--E---N--V  ----------  ----------  ----------

1151                                                      1200
Hap         ..........  ..........  ..........  ..........  ..........
HK368IGA    APVPPPAPAT  ..........  ..........  ..........  ..........
HK393IGA    APVPPPAPAT  ..........  ..........  ..........  ..........
HK715IGA    TPVPPPAPAT  ..........  ..........  ..........  ..........
HK61IGA     TPVPPPAPAT  ESAIASEQPE  TRPAETAQPA  MEETNTANST  ETAPKSDTAT
Consensus   ----------  ----------  ----------  ----------  ----------
```

FIG._7F

```
                                                                    1250
Hap          . . . . . . . . . . .   . . . . . . . . . .   RAEQAERTLE  AKQVEPT. . .   . . . . . . . . . .
HK368IGA     . . . . . . . . . . .   PSETTETVAE           NSKQESKTVE  KNEQDATETT    AQNREVAKEA
HK393IGA     . . . . . . . . . . .   PSETTETVAE           NSKQESKTVE  KNEQDATETT    AQNREVAKEA
HK715IGA     . . . . . . . . . . .   PSETTETVAE           NSKQESKTVE  KNEQDATETT    AQNGEVAEEA
HK61IGA      QTENPNSESV              PSETTEKVAE           NPPQENETVA  KNEQEATEPT    PQNGEVAKED
Consensus    – – – – – – – – – –     – – – – – – – – – –  – – –Q– – – – – – –T– – –  – – – – – – – – – –

1251                                           1300
Hap          . . . .AKTQT            GE. . . . . . . . .  . . . . . . . . . .       . . . . . . . . . .
HK368IGA     KSNVKANTQT              NEVAQSGSET           KETQTTETK.                . . . .ETATVE
HK393IGA     KSNVKANTQT              NEVAQSGSET           KETQTTETK.                . . . .ETATVE
HK715IGA     KPNVKANTQT              NEVAQSGSET           EETQTTEIK.                . . . .ETAKVE
HK61IGA      QPTVEANTQT              NEATQSEGKT           EETQTAETKS                EPTESVTVSE       NQPEKTVSQS
Consensus    – – – –A–TQT            – –E– – – – – –      – – – – – – – – – –       – – – – – – – – – –

1301                                           1350
Hap          . . . . . . . . . . .   . . . . . . . . . .  . . . . . . . . . .       . . . . . . . . . .
HK368IGA     KEEK. . . . .           . . . . . . . . . .  . . . . . . . . . .       . . . . . . . . . .
HK393IGA     KEEK. . . . .           . . . . . . . . . .  . . . . . . . . . .       . . . . . . . . . .
HK715IGA     KEEEKAKVEKE             EKAKVEKDEI           QEAPQMASET                 SPKQAKPAPK       EVSTDTKVEE
HK61IGA      TEDKVVVEKE              EKAKVETEET           QKAPQVTSKE                 PPKQAEPAPE       EVPTDTNAEE
Consensus    – – – – – – – – – –     – – – – – – – – – –  – – – – – – – – – –       – – – – – – – – – –

1351                                           1400
Hap          . . . . . . . . . . .   . . . . . . . . . .  . . . . . . . . . .       . . . . . . . . . .
HK368IGA     . . . . . . . . . . .   . . . . . . . . . .  . . . . . . . . . .       . . . . . . . . . .
HK393IGA     . . . . . . . . . . .   . . . . . . . . . .  . . . . . . . . . .       . . . . . . . . . .
HK715IGA     TQVQAQPQTQ              STTVAAAEAT           SPNSKPAEET                 .QPSEKTNAE       PVTPVVSKNQ
HK61IGA      A. .QALQQTQ             PTTVAAAETT           SPNSKPAEET                 QQPSEKTNAE       PVTPVVS. . .
Consensus    – – – – – – – – – –     – – – – – – – – – –  – – – – – – – – – –       – – – – – – – – – –
```

FIG._7G

```
              1401                                              1450
Hap           ..........  ..........  ..........  .....PKVRS  RRAARAAFPD  TLP.......
HK368IGA      ..........  ..........  ....AKVETE  KTQEVPKVTS  QVSPKQEQSE  T.........
HK393IGA      TENTTDQPTE  REKTAKVETE  ....AKVETE  KTQEVPKVTS  QVSPKQEQSE  T.........
HK71SIGA      .ENTATQPTE  TEETAKVEKE  ..........  KTQEPPQVAS  QASPKQEQSE  T.........
HK61IGA       ..........  ..........  ..........  KTQEVPQVAS  QESPKQEQPA  AKPQAQTKPQ
Consensus     ----------  ----------  ----------  ----P-V--S  ----------  ----------

1451                                              1500
Hap           ..........  ..........  ..........  ..........  ..........  .........V
HK368IGA      ..........  ..........  ..........  ..........  ..........  .........V
HK393IGA      ..........  ..........  ..........  ..........  ..........  .........V
HK71SIGA      ..........  ..........  ..........  ..........  ..........  .........V
HK61IGA       AEPARENVLT  TKNVGEPQPQ  AQPQTQSTAV  PTTGETAANS  KPAAKPQAQA
Consensus     ----------  ----------  ----------  ----------  ----------  ----------

1501                                              1550
Hap           ...D        QSLLNALEA.  ......KQAEL  TAETQKSKAK  TKK.......
HK368IGA      QPQAEPAREN  DPTVNIKEP.  ...QSQTNT   TADTEQPAKE  TSSNVE....
HK393IGA      QPQAEPAREN  DPTVNIKEP.  ...QSQTNT   TADTEQPAKE  TSSNVE....
HK71SIGA      QPQAVLESEN  VPTVNNAEEV  QAQLQTQTSA  TVSTKQPAPE  NSINTG....
HK61IGA       KPQTEPAREN  VSTVNTKEP.  ....QSQTSA  TVSTEQPAKE  TSSNVEQPAP
Consensus     ----------  ----N---E-  -------Q--  ----T-----  ----------

1551                                              1600
Hap           ..........  ..........  ..........  .........V  RSKRAVFSDP  LLDQSL....
HK368IGA      ..........  ..........  ..........  ....QPVT    ESTTVNTGNS  VVEN......
HK393IGA      ..........  ..........  ..........  ....QPVT    ESTTVNTGNS  VVEN......
HK71SIGA      ...SAT      AITETAEKSD  KPQTETAAST  EDASQHKANT  VADNSVANNS
HK61IGA       ENSINTGSAT  TMTETAEKSD  KPQMET..VT  ENDRQPEANT  VADNSVANNS
Consensus     ----------  ----------  ----------  ----------  ----------  ----------
```

FIG._7H

```
          1601                                                      1650
Hap       ..........  ..........  .F ALEAAALEVID APQQSEKDRL AQEEAEKQRK
HK368IGA  ..........  ..........  .. .......... PENTTPATTQ PTVNSESSN.
HK393IGA  ..........  ..........  .. .......... PENTTPATTQ PTVNSESSN.
HK715IGA  ESSEPKSRRR  RSISQPQETS  .. .......... AEETTAASTD ETTIADNSKR
HK61IGA   ESSESKSRRR  RSVSQPKETS  .. .......... AEETTVASTQ ETTVDNSVST
Consensus ----------  ----------  -- ---------- ---------- ----------

1651                                                      1700
Hap       ..........  ..........  .......... .......... ..QKDLI
HK368IGA  SVRSVPHNVE  PATTSSND..  .......... .......... RSTVALCDLT
HK393IGA  SVRSVPHNVE  PATTSSND..  .......... .......... RSTVALCDLT
HK715IGA  SVRS.....E  PTVTNGSD..  .......... .......... RSTVALRDLT
HK61IGA   SVQTNSYEPV  ELPTENAENA  ENVQSGNNVA .......... NSQPALRNLT
Consensus ----------  ----------  ---------- ---------- ----------

1701                                                      1750
Hap       LSA.....TV  NSMLSVQDEL  DRL.FVDQAQ SAVWTNIAQD KRRYDSDAFR
HK368IGA  ARAKAQFVAL  NVGKAVSQHI  SQLEMNNEGQ YNVWVSNTSM NKNYSSSQYR
HK393IGA  ARAKAQFVAL  NVGKAVSQHI  SQLEMNNEGQ YNVWVSNTSM NKNYSSSQYR
HK715IGA  AMAKAQFVAL  NVGKAVSQHI  SQLEMNNEGQ YNVWVSNTSM NENYSSSQYR
HK61IGA   AMAKAQFVAL  NVGKAVSQHI  SQLEMNNEGQ YNVWISNTSM NKNYSSEQYR
Consensus ----A-----  N-----V---  ---L------ ---VW----- ---Y-S---R 1751                                                      1800
Hap       AYQQQKTNLR  QIGVQKALAN  GRIGAVFSHS RSDNTFDEQV KNHATLTMMS
HK368IGA  RFSSKSTQTQ  LGWDQTISNN  VQLGGVFTYV RNSNNFDKAT SKN.TLAQVN
HK393IGA  RFSSKSTQTQ  LGWDQTISNN  VQLGGVFTYV RNSNNFDKAT SKN.TLAQVN
HK715IGA  RFSSKSTQTQ  LGWDQTISNN  VQLGGVFTYV RNSNNFDKAS SKN.TLAQVN
HK61IGA   RFSSKSTQTQ  LGWDQTISNN  VQLGGVFTYV RNSNNFDKAS SKN.TLAQVN
Consensus ------T---  ----Q-----  ---G-VF--- R--N-FD--- ----TL----
```

FIG._71

```
              1801                                                                            1850
Hap           GFAQYQWGDL QF..GVNVGT GISASKMAEE QSRKIHRKAI NYGVNASYQF
HK368IGA      FYSKY.YADN HWYLGIDLGY GKFQSKLQTN HNAKFARHTA QFGLTAGKAF
HK393IGA      FYSKY.YADN HWYLGIDLGY GKFQSKLQTN HNAKFARHTA QFGLTAGKAF
HK715IGA      FYSKY.YADN HWYLGIDLGY GKFQSNLKTN HNAKFARHTA QFGLTAGKAF
HK61IGA       FYSKY.YADN HWYLGIDLGY GKFQSNLQTN NNAKFARHTA QIGLTAGKAF
Consensus     -----Y---- ------G--- ------S--- -------K-R --G--A---F 1851                                                                            1900
Hap           RLGQLGIQPY FGVNRYFIER ENYQSEEVRV KTPSLAFNRY NAGIRVDYTF
HK368IGA      NLGNFGITPI VGVRYSYLSN ADFALDQARI KVNPISVKTA FAQVDLSYTY
HK393IGA      NLGNFGITPI VGVRYSYLSN ADFALDQARI KVNPISVKTA FAQVDLSYTY
HK715IGA      NLGNFGITPI VGVRYSYLSN ANFALAKDRI KVNPISVKTA FAQVDLSYTY
HK61IGA       NLGNFAVKPT VGVRYSYLSN ADFALAQDRI KVNPISVKTA FAQVDLSYTY
Consensus     -LG-----P- ------GV-- --------R- K--------- -A-----YT- 1901                                                                            1950
Hap           TPTDNISVKP YFFVNYVDVS NANVQTTVNL TVLQQPFGRY WQKEVGLKAE
HK368IGA      .HLGEFSVTP ILSARY.DAN QGSGKINVNG YDFAYNVENQ QQYNAGLKLK
HK393IGA      .HLGEFSVTP ILSARY.DAN QGSGKINVNG YDFAYNVENQ QQYNAGLKLK
HK715IGA      .HLGEFSVTP ILSARY.DTN QGSGKINVNQ YDFAYNVENQ QQYNAGLKLK
HK61IGA       .HLGEFSITP ILSARY.DAN QGNGKINVSV YDFAYNVENQ QQYNAGLKLK
Consensus     -------S--P ------Y-D-- --------V-- K--------- -Q----GLK--

1951                              1982
Hap           ILHFQISAFI SKSQGSQLGK QQNVGVKLGY RW
HK368IGA      YHNVKLSLIG GLTKAKQAEK QKTAELKLSF SF
HK393IGA      YHNVKLSLIG GLTKAKQAEK QKTAELKLSF SF
HK715IGA      YHNVKLSLIG GLTKAKQAEK QKTAELKLSF SF
HK61IGA       YHNVKLSLIG GLTKAKQAEK QKTAEVKLSF SF
Consensus     -------S--- ---------- -----Q---K-  Q------KL-- --
```

FIG._7J

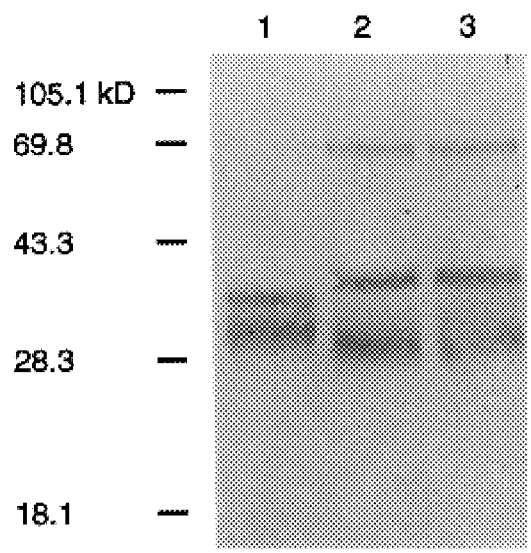
FIG._8
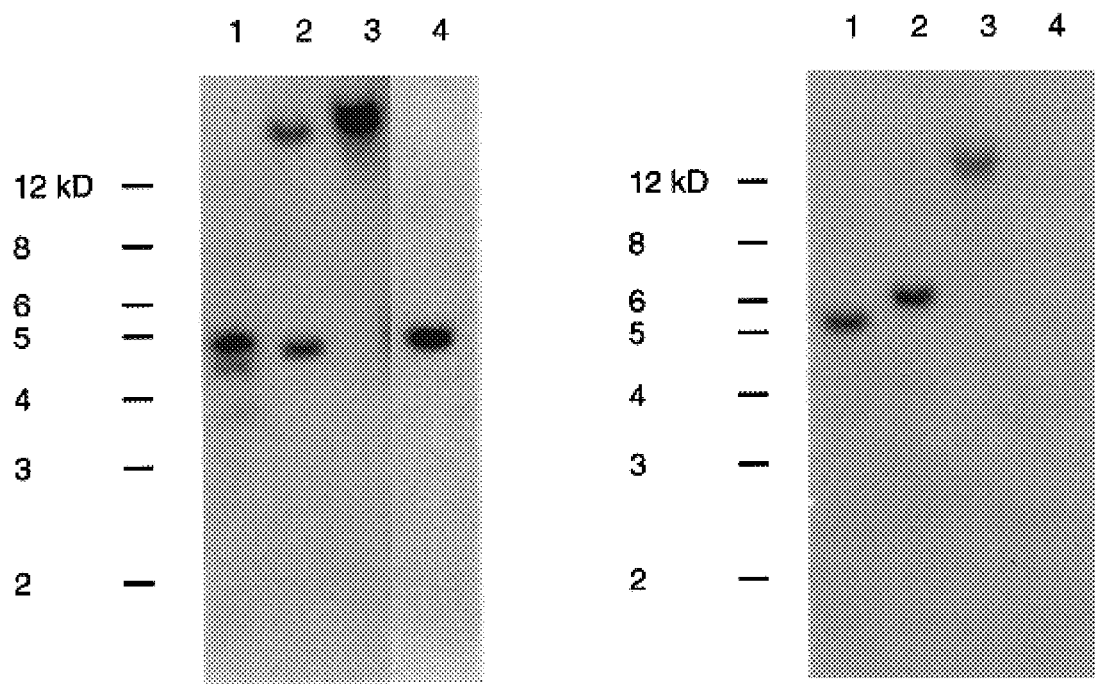
FIG._9A   FIG._9B

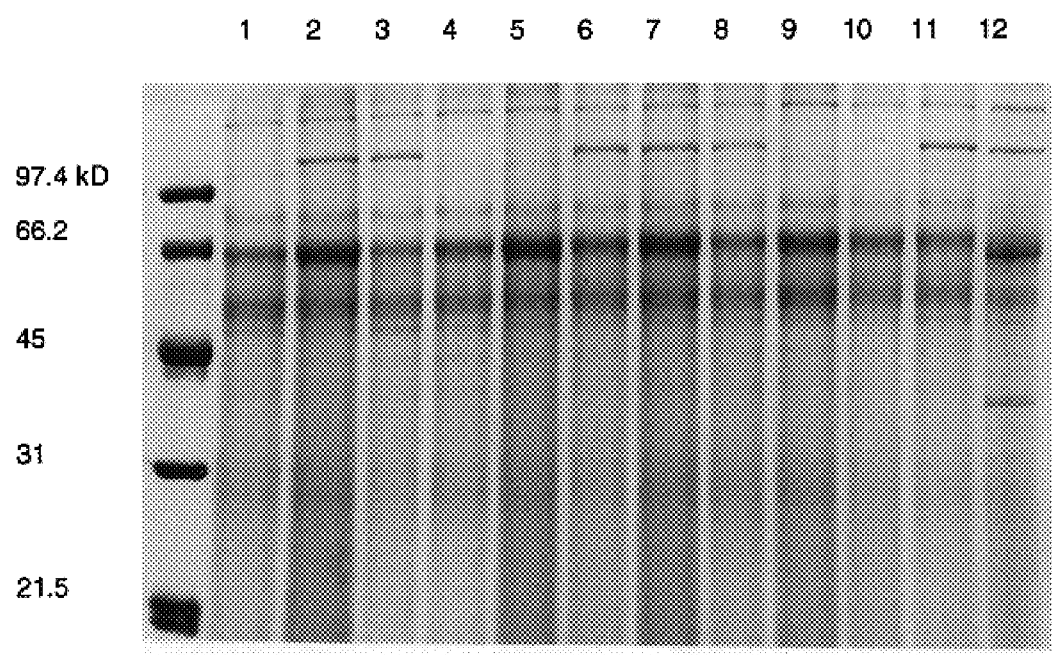
FIG._10

SEQUENCE LISTING (1) GENERAL INFORMATION:

(iii) NUMBER OF SEQUENCES: 9

(2) INFORMATION FOR SEQ ID NO:1:

```
    (i) SEQUENCE CHARACTERISTICS:
        (A) LENGTH: 4319 base pairs
        (B) TYPE: nucleic acid
        (C) STRANDEDNESS: double
        (D) TOPOLOGY: both (ix) FEATURE:
        (A) NAME/KEY: CDS
        (B) LOCATION: 60..4241

(xi) SEQUENCE DESCRIPTION: SEQ ID NO:1:

TCAATAGTCG TTTAACTAGT ATTTTTTAAT ACGAAAAATT ACTTAATTAA ATAAACATT          59

ATG AAA AAA ACT GTA TTT CGT CTT AAT TTT TTA ACC GCT TGC ATT TCA         107
Met Lys Lys Thr Val Phe Arg Leu Asn Phe Leu Thr Ala Cys Ile Ser
 1               5                  10                  15

TTA GGG ATA GTA TCG CAA GCG TGG GCT GGT CAC ACT TAT TTT GGG ATT         155
Leu Gly Ile Val Ser Gln Ala Trp Ala Gly His Thr Tyr Phe Gly Ile
                20                  25                  30

GAT TAC CAA TAT TAT CGT GAT TTT GCC GAG AAT AAA GGG AAG TTC ACA         203
Asp Tyr Gln Tyr Tyr Arg Asp Phe Ala Glu Asn Lys Gly Lys Phe Thr
            35                  40                  45

GTT GGG GCT CAA AAT ATT AAG GTT TAT AAC AAA CAA GGG CAA TTA GTT         251
Val Gly Ala Gln Asn Ile Lys Val Tyr Asn Lys Gln Gly Gln Leu Val
        50                  55                  60

GGC ACA TCA ATG ACA AAA GCC CCG ATG ATT GAT TTT TCT GTA GTG TCA         299
Gly Thr Ser Met Thr Lys Ala Pro Met Ile Asp Phe Ser Val Val Ser
 65                 70                  75                  80

CGT AAC GGC GTG GCA GCC TTG GTT GAA AAT CAA TAT ATT GTG AGC GTG         347
Arg Asn Gly Val Ala Ala Leu Val Glu Asn Gln Tyr Ile Val Ser Val
                85                  90                  95

GCA CAT AAC GTA GGA TAT ACA GAT GTT GAT TTT GGT GCA GAG GGA AAC         395
Ala His Asn Val Gly Tyr Thr Asp Val Asp Phe Gly Ala Glu Gly Asn
            100                 105                 110

AAC CCC GAT CAA CAT CGT TTT ACT TAT AAG ATT GTA AAA CGA AAT AAC         443
Asn Pro Asp Gln His Arg Phe Thr Tyr Lys Ile Val Lys Arg Asn Asn
        115                 120                 125

TAC AAA AAA GAT AAT TTA CAT CCT TAT GAG GAC GAT TAC CAT AAT CCA         491
Tyr Lys Lys Asp Asn Leu His Pro Tyr Glu Asp Asp Tyr His Asn Pro
130                 135                 140

CGA TTA CAT AAA TTC GTT ACA GAA GCG GCT CCA ATT GAT ATG ACT TCG         539
Arg Leu His Lys Phe Val Thr Glu Ala Ala Pro Ile Asp Met Thr Ser
145                 150                 155                 160

AAT ATG AAT GGC AGT ACT TAT TCA GAT AGA ACA AAA TAT CCA GAA CGT         587
Asn Met Asn Gly Ser Thr Tyr Ser Asp Arg Thr Lys Tyr Pro Glu Arg
                165                 170                 175

GTT CGT ATC GGC TCT GGA CGG CAG TTT TGG CGA AAT GAT CAA GAC AAA         635
Val Arg Ile Gly Ser Gly Arg Gln Phe Trp Arg Asn Asp Gln Asp Lys
            180                 185                 190

GGC GAC CAA GTT GCC GGT GCA TAT CAT TAT CTG ACA GCT GGC AAT ACA         683
Gly Asp Gln Val Ala Gly Ala Tyr His Tyr Leu Thr Ala Gly Asn Thr
        195                 200                 205

CAC AAT CAG CGT GGA GCA GGT AAT GGA TAT TCG TAT TTG GGA GGC GAT         731
His Asn Gln Arg Gly Ala Gly Asn Gly Tyr Ser Tyr Leu Gly Gly Asp
    210                 215                 220

GTT CGT AAA GCG GGA GAA TAT GGT CCA TTA CCG ATT GCA GGC TCA AAG         779
Val Arg Lys Ala Gly Glu Tyr Gly Pro Leu Pro Ile Ala Gly Ser Lys
225                 230                 235                 240

GGG GAC AGT GGT TCT CCG ATG TTT ATT TAT GAT GCT GAA AAA CAA AAA         827
Gly Asp Ser Gly Ser Pro Met Phe Ile Tyr Asp Ala Glu Lys Gln Lys
                245                 250                 255
```

```
TGG TTA ATT AAT GGG ATA TTA CGG GAA GGC AAC CCT TTT GAA GGC AAA      875
Trp Leu Ile Asn Gly Ile Leu Arg Glu Gly Asn Pro Phe Glu Gly Lys
        260                 265                 270

GAA AAT GGG TTT CAA TTG GTT CGC AAA TCT TAT TTT GAT GAA ATT TTC      923
Glu Asn Gly Phe Gln Leu Val Arg Lys Ser Tyr Phe Asp Glu Ile Phe
            275                 280                 285

GAA AGA GAT TTA CAT ACA TCA CTT TAC ACC CGA GCT GGT AAT GGA GTG      971
Glu Arg Asp Leu His Thr Ser Leu Tyr Thr Arg Ala Gly Asn Gly Val
290                 295                 300

TAC ACA ATT AGT GGA AAT GAT AAT GGT CAG GGG TCT ATA ACT CAG AAA     1019
Tyr Thr Ile Ser Gly Asn Asp Asn Gly Gln Gly Ser Ile Thr Gln Lys
305                 310                 315                 320

TCA GGA ATA CCA TCA GAA ATT AAA ATT ACG TTA GCA AAT ATG AGT TTA     1067
Ser Gly Ile Pro Ser Glu Ile Lys Ile Thr Leu Ala Asn Met Ser Leu
                325                 330                 335

CCT TTG AAA GAG AAG GAT AAA GTT CAT AAT CCT AGA TAT GAC GGA CCT     1115
Pro Leu Lys Glu Lys Asp Lys Val His Asn Pro Arg Tyr Asp Gly Pro
                340                 345                 350

AAT ATT TAT TCT CCA CGT TTA AAC AAT GGA GAA ACG CTA TAT TTT ATG     1163
Asn Ile Tyr Ser Pro Arg Leu Asn Asn Gly Glu Thr Leu Tyr Phe Met
            355                 360                 365

GAT CAA AAA CAA GGA TCA TTA ATC TTC GCA TCT GAC ATT AAC CAA GGG     1211
Asp Gln Lys Gln Gly Ser Leu Ile Phe Ala Ser Asp Ile Asn Gln Gly
370                 375                 380

GCG GGT GGT CTT TAT TTT GAG GGT AAT TTT ACA GTA TCT CCA AAT TCT     1259
Ala Gly Gly Leu Tyr Phe Glu Gly Asn Phe Thr Val Ser Pro Asn Ser
385                 390                 395                 400

AAC CAA ACT TGG CAA GGA GCT GGC ATA CAT GTA AGT GAA AAT AGC ACC     1307
Asn Gln Thr Trp Gln Gly Ala Gly Ile His Val Ser Glu Asn Ser Thr
                405                 410                 415

GTT ACT TGG AAA GTA AAT GGC GTG GAA CAT GAT CGA CTT TCT AAA ATT     1355
Val Thr Trp Lys Val Asn Gly Val Glu His Asp Arg Leu Ser Lys Ile
                420                 425                 430

GGT AAA GGA ACA TTG CAC GTT CAA GCC AAA GGG GAA AAT AAA GGT TCG     1403
Gly Lys Gly Thr Leu His Val Gln Ala Lys Gly Glu Asn Lys Gly Ser
            435                 440                 445

ATC AGC GTA GGC GAT GGT AAA GTC ATT TTG GAG CAG CAG GCA GAC GAT     1451
Ile Ser Val Gly Asp Gly Lys Val Ile Leu Glu Gln Gln Ala Asp Asp
450                 455                 460

CAA GGC AAC AAA CAA GCC TTT AGT GAA ATT GGC TTG GTT AGC GGC AGA     1499
Gln Gly Asn Lys Gln Ala Phe Ser Glu Ile Gly Leu Val Ser Gly Arg
465                 470                 475                 480

GGG ACT GTT CAA TTA AAC GAT GAT AAA CAA TTT GAT ACC GAT AAA TTT     1547
Gly Thr Val Gln Leu Asn Asp Asp Lys Gln Phe Asp Thr Asp Lys Phe
                485                 490                 495

TAT TTC GGC TTT CGT GGT GGT CGC TTA GAT CTT AAC GGG CAT TCA TTA     1595
Tyr Phe Gly Phe Arg Gly Gly Arg Leu Asp Leu Asn Gly His Ser Leu
                500                 505                 510

ACC TTT AAA CGT ATC CAA AAT ACG GAC GAG GGG GCA ATG ATT GTG AAC     1643
Thr Phe Lys Arg Ile Gln Asn Thr Asp Glu Gly Ala Met Ile Val Asn
            515                 520                 525

CAT AAT ACA ACT CAA GCC GCT AAT GTC ACT ATT ACT GGG AAC GAA AGC     1691
His Asn Thr Thr Gln Ala Ala Asn Val Thr Ile Thr Gly Asn Glu Ser
530                 535                 540

ATT GTT CTA CCT AAT GGA AAT AAT ATT AAT AAA CTT GAT TAC AGA AAA     1739
Ile Val Leu Pro Asn Gly Asn Asn Ile Asn Lys Leu Asp Tyr Arg Lys
545                 550                 555                 560

GAA ATT GCC TAC AAC GGT TGG TTT GGC GAA ACA GAT AAA AAT AAA CAC     1787
Glu Ile Ala Tyr Asn Gly Trp Phe Gly Glu Thr Asp Lys Asn Lys His
                565                 570                 575
```

```
AAT GGG CGA TTA AAC CTT ATT TAT AAA CCA ACC ACA GAA GAT CGT ACT      1835
Asn Gly Arg Leu Asn Leu Ile Tyr Lys Pro Thr Thr Glu Asp Arg Thr
                580                 585                 590

TTG CTA CTT TCA GGT GGT ACA AAT TTA AAA GGC GAT ATT ACC CAA ACA      1883
Leu Leu Leu Ser Gly Gly Thr Asn Leu Lys Gly Asp Ile Thr Gln Thr
            595                 600                 605

AAA GGT AAA CTA TTT TTC AGC GGT AGA CCG ACA CCG CAC GCC TAC AAT      1931
Lys Gly Lys Leu Phe Phe Ser Gly Arg Pro Thr Pro His Ala Tyr Asn
        610                 615                 620

CAT TTA AAT AAA CGT TGG TCA GAA ATG GAA GGT ATA CCA CAA GGC GAA      1979
His Leu Asn Lys Arg Trp Ser Glu Met Glu Gly Ile Pro Gln Gly Glu
625                 630                 635                 640

ATT GTG TGG GAT CAC GAT TGG ATC AAC CGT ACA TTT AAA GCT GAA AAC      2027
Ile Val Trp Asp His Asp Trp Ile Asn Arg Thr Phe Lys Ala Glu Asn
                645                 650                 655

TTC CAA ATT AAA GGC GGA AGT GCG GTG GTT TCT CGC AAT GTT TCT TCA      2075
Phe Gln Ile Lys Gly Gly Ser Ala Val Val Ser Arg Asn Val Ser Ser
            660                 665                 670

ATT GAG GGA AAT TGG ACA GTC AGC AAT AAT GCA AAT GCC ACA TTT GGT      2123
Ile Glu Gly Asn Trp Thr Val Ser Asn Asn Ala Asn Ala Thr Phe Gly
        675                 680                 685

GTT GTG CCA AAT CAA CAA AAT ACC ATT TGC ACG CGT TCA GAT TGG ACA      2171
Val Val Pro Asn Gln Gln Asn Thr Ile Cys Thr Arg Ser Asp Trp Thr
690                 695                 700

GGA TTA ACG ACT TGT CAA AAA GTG GAT TTA ACC GAT ACA AAA GTT ATT      2219
Gly Leu Thr Thr Cys Gln Lys Val Asp Leu Thr Asp Thr Lys Val Ile
705                 710                 715                 720

AAT TCT ATA CCA AAA ACA CAA ATC AAT GGC TCT ATT AAT TTA ACT GAT      2267
Asn Ser Ile Pro Lys Thr Gln Ile Asn Gly Ser Ile Asn Leu Thr Asp
                725                 730                 735

AAT GCA ACG GCG AAT GTT AAA GGT TTA GCA AAA CTT AAT GGC AAT GTC      2315
Asn Ala Thr Ala Asn Val Lys Gly Leu Ala Lys Leu Asn Gly Asn Val
            740                 745                 750

ACT TTA ACA AAT CAC AGC CAA TTT ACA TTA AGC AAC AAT GCC ACC CAA      2363
Thr Leu Thr Asn His Ser Gln Phe Thr Leu Ser Asn Asn Ala Thr Gln
        755                 760                 765

ATA GGC AAT ATT CGA CTT TCC GAC AAT TCA ACT GCA ACG GTG GAT AAT      2411
Ile Gly Asn Ile Arg Leu Ser Asp Asn Ser Thr Ala Thr Val Asp Asn
770                 775                 780

GCA AAC TTG AAC GGT AAT GTG CAT TTA ACG GAT TCA GCT CAA TTT TCT      2459
Ala Asn Leu Asn Gly Asn Val His Leu Thr Asp Ser Ala Gln Phe Ser
785                 790                 795                 800

TTA AAA AAC AGC CAT TTT TCG CAC CAA ATT CAG GGA GAC AAA GGC ACA      2507
Leu Lys Asn Ser His Phe Ser His Gln Ile Gln Gly Asp Lys Gly Thr
                805                 810                 815

ACA GTG ACG TTG GAA AAT GCG ACT TGG ACA ATG CCT AGC GAT ACT ACA      2555
Thr Val Thr Leu Glu Asn Ala Thr Trp Thr Met Pro Ser Asp Thr Thr
            820                 825                 830

TTG CAG AAT TTA ACG CTA AAT AAC AGT ACG ATC ACG TTA AAT TCA GCT      2603
Leu Gln Asn Leu Thr Leu Asn Asn Ser Thr Ile Thr Leu Asn Ser Ala
        835                 840                 845

TAT TCA GCT AGC TCA AAC AAT ACG CCA CGT CGC CGT TCA TTA GAG ACG      2651
Tyr Ser Ala Ser Ser Asn Asn Thr Pro Arg Arg Arg Ser Leu Glu Thr
850                 855                 860

GAA ACA ACG CCA ACA TCG GCA GAA CAT CGT TTC AAC ACA TTG ACA GTA      2699
Glu Thr Thr Pro Thr Ser Ala Glu His Arg Phe Asn Thr Leu Thr Val
865                 870                 875                 880

AAT GGT AAA TTG AGT GGG CAA GGC ACA TTC CAA TTT ACT TCA TCT TTA      2747
Asn Gly Lys Leu Ser Gly Gln Gly Thr Phe Gln Phe Thr Ser Ser Leu
```

|  |  |  |  |  |  |  |  |  |  |  |  |  |  |  |  |
|---|---|---|---|---|---|---|---|---|---|---|---|---|---|---|---|
|  |  |  |  | 885 |  |  |  | 890 |  |  |  |  | 895 |  |  |
| TTT | GGC | TAT | AAA | AGC | GAT | AAA | TTA | AAA | TTA | TCC | AAT | GAC | GCT | GAG | GGC | 2795
| Phe | Gly | Tyr | Lys | Ser | Asp | Lys | Leu | Lys | Leu | Ser | Asn | Asp | Ala | Glu | Gly |
|  |  |  | 900 |  |  |  | 905 |  |  |  |  | 910 |  |  |  |
| GAT | TAC | ATA | TTA | TCT | GTT | CGC | AAC | ACA | GGC | AAA | GAA | CCC | GAA | ACC | CTT | 2843
| Asp | Tyr | Ile | Leu | Ser | Val | Arg | Asn | Thr | Gly | Lys | Glu | Pro | Glu | Thr | Leu |
|  |  |  | 915 |  |  |  | 920 |  |  |  |  | 925 |  |  |  |
| GAG | CAA | TTA | ACT | TTG | GTT | GAA | AGC | AAA | GAT | AAT | CAA | CCG | TTA | TCA | GAT | 2891
| Glu | Gln | Leu | Thr | Leu | Val | Glu | Ser | Lys | Asp | Asn | Gln | Pro | Leu | Ser | Asp |
|  | 930 |  |  |  |  | 935 |  |  |  |  | 940 |  |  |  |  |
| AAG | CTC | AAA | TTT | ACT | TTA | GAA | AAT | GAC | CAC | GTT | GAT | GCA | GGT | GCA | TTA | 2939
| Lys | Leu | Lys | Phe | Thr | Leu | Glu | Asn | Asp | His | Val | Asp | Ala | Gly | Ala | Leu |
| 945 |  |  |  |  | 950 |  |  |  |  | 955 |  |  |  |  | 960 |
| CGT | TAT | AAA | TTA | GTG | AAG | AAT | GAT | GGC | GAA | TTC | CGC | TTG | CAT | AAC | CCA | 2987
| Arg | Tyr | Lys | Leu | Val | Lys | Asn | Asp | Gly | Glu | Phe | Arg | Leu | His | Asn | Pro |
|  |  |  | 965 |  |  |  | 970 |  |  |  |  | 975 |  |  |  |
| ATA | AAA | GAG | CAG | GAA | TTG | CAC | AAT | GAT | TTA | GTA | AGA | GCA | GAG | CAA | GCA | 3035
| Ile | Lys | Glu | Gln | Glu | Leu | His | Asn | Asp | Leu | Val | Arg | Ala | Glu | Gln | Ala |
|  |  |  | 980 |  |  |  | 985 |  |  |  |  | 990 |  |  |  |
| GAA | CGA | ACA | TTA | GAA | GCC | AAA | CAA | GTT | GAA | CCG | ACT | GCT | AAA | ACA | CAA | 3083
| Glu | Arg | Thr | Leu | Glu | Ala | Lys | Gln | Val | Glu | Pro | Thr | Ala | Lys | Thr | Gln |
|  |  | 995 |  |  |  |  | 1000 |  |  |  |  | 1005 |  |  |  |
| ACA | GGT | GAG | CCA | AAA | GTG | CGG | TCA | AGA | AGA | GCA | GCG | AGA | GCA | GCG | TTT | 3131
| Thr | Gly | Glu | Pro | Lys | Val | Arg | Ser | Arg | Arg | Ala | Ala | Arg | Ala | Ala | Phe |
|  | 1010 |  |  |  |  | 1015 |  |  |  |  | 1020 |  |  |  |  |
| CCT | GAT | ACC | CTG | CCT | GAT | CAA | AGC | CTG | TTA | AAC | GCA | TTA | GAA | GCC | AAA | 3179
| Pro | Asp | Thr | Leu | Pro | Asp | Gln | Ser | Leu | Leu | Asn | Ala | Leu | Glu | Ala | Lys |
| 1025 |  |  |  |  | 1030 |  |  |  |  | 1035 |  |  |  |  | 1040 |
| CAA | GCT | GAA | CTG | ACT | GCT | GAA | ACA | CAA | AAA | AGT | AAG | GCA | AAA | ACA | AAA | 3227
| Gln | Ala | Glu | Leu | Thr | Ala | Glu | Thr | Gln | Lys | Ser | Lys | Ala | Lys | Thr | Lys |
|  |  |  | 1045 |  |  |  | 1050 |  |  |  |  | 1055 |  |  |  |
| AAA | GTG | CGG | TCA | AAA | AGA | GCA | GTG | TTT | TCT | GAT | CCC | CTG | CTT | GAT | CAA | 3275
| Lys | Val | Arg | Ser | Lys | Arg | Ala | Val | Phe | Ser | Asp | Pro | Leu | Leu | Asp | Gln |
|  |  |  | 1060 |  |  |  | 1065 |  |  |  |  | 1070 |  |  |  |
| AGC | CTG | TTC | GCA | TTA | GAA | GCC | GCA | CTT | GAG | GTT | ATT | GAT | GCC | CCA | CAG | 3323
| Ser | Leu | Phe | Ala | Leu | Glu | Ala | Ala | Leu | Glu | Val | Ile | Asp | Ala | Pro | Gln |
|  |  |  | 1075 |  |  |  | 1080 |  |  |  |  | 1085 |  |  |  |
| CAA | TCG | GAA | AAA | GAT | CGT | CTA | GCT | CAA | GAA | GAA | GCG | GAA | AAA | CAA | CGC | 3371
| Gln | Ser | Glu | Lys | Asp | Arg | Leu | Ala | Gln | Glu | Glu | Ala | Glu | Lys | Gln | Arg |
|  |  |  | 1090 |  |  |  | 1095 |  |  |  |  | 1100 |  |  |  |
| AAA | CAA | AAA | GAC | TTG | ATC | AGC | CGT | TAT | TCA | AAT | AGT | GCG | TTA | TCA | GAA | 3419
| Lys | Gln | Lys | Asp | Leu | Ile | Ser | Arg | Tyr | Ser | Asn | Ser | Ala | Leu | Ser | Glu |
| 1105 |  |  |  |  | 1110 |  |  |  |  | 1115 |  |  |  |  | 1120 |
| TTA | TCT | GCA | ACA | GTA | AAT | AGT | ATG | CTT | TCT | GTT | CAA | GAT | GAA | TTA | GAT | 3467
| Leu | Ser | Ala | Thr | Val | Asn | Ser | Met | Leu | Ser | Val | Gln | Asp | Glu | Leu | Asp |
|  |  |  | 1125 |  |  |  | 1130 |  |  |  |  | 1135 |  |  |  |
| CGT | CTT | TTT | GTA | GAT | CAA | GCA | CAA | TCT | GCC | GTG | TGG | ACA | AAT | ATC | GCA | 3515
| Arg | Leu | Phe | Val | Asp | Gln | Ala | Gln | Ser | Ala | Val | Trp | Thr | Asn | Ile | Ala |
|  |  |  | 1140 |  |  |  | 1145 |  |  |  |  | 1150 |  |  |  |
| CAG | GAT | AAA | AGA | CGC | TAT | GAT | TCT | GAT | GCG | TTC | CGT | GCT | TAT | CAG | CAG | 3563
| Gln | Asp | Lys | Arg | Arg | Tyr | Asp | Ser | Asp | Ala | Phe | Arg | Ala | Tyr | Gln | Gln |
|  |  |  | 1155 |  |  |  | 1160 |  |  |  |  | 1165 |  |  |  |
| CAG | AAA | ACG | AAC | TTA | CGT | CAA | ATT | GGG | GTG | CAA | AAA | GCC | TTA | GCT | AAT | 3611
| Gln | Lys | Thr | Asn | Leu | Arg | Gln | Ile | Gly | Val | Gln | Lys | Ala | Leu | Ala | Asn |
|  |  |  | 1170 |  |  |  | 1175 |  |  |  |  | 1180 |  |  |  |
| GGA | CGA | ATT | GGG | GCA | GTT | TTC | TCG | CAT | AGC | CGT | TCA | GAT | AAT | ACC | TTT | 3659
| Gly | Arg | Ile | Gly | Ala | Val | Phe | Ser | His | Ser | Arg | Ser | Asp | Asn | Thr | Phe |
| 1185 |  |  |  |  | 1190 |  |  |  |  | 1195 |  |  |  |  | 1200 |
| GAT | GAA | CAG | GTT | AAA | AAT | CAC | GCG | ACA | TTA | ACG | ATG | ATG | TCG | GGT | TTT | 3707

-continued

```
Asp Glu Gln Val Lys Asn His Ala Thr Leu Thr Met Met Ser Gly Phe
            1205                1210                1215

GCC CAA TAT CAA TGG GGC GAT TTA CAA TTT GGT GTA AAC GTG GGA ACG        3755
Ala Gln Tyr Gln Trp Gly Asp Leu Gln Phe Gly Val Asn Val Gly Thr
            1220                1225                1230

GGA ATC AGT GCG AGT AAA ATG GCT GAA GAA CAA AGC CGA AAA ATT CAT        3803
Gly Ile Ser Ala Ser Lys Met Ala Glu Glu Gln Ser Arg Lys Ile His
            1235                1240                1245

CGA AAA GCG ATA AAT TAT GGC GTG AAT GCA AGT TAT CAG TTC CGT TTA        3851
Arg Lys Ala Ile Asn Tyr Gly Val Asn Ala Ser Tyr Gln Phe Arg Leu
            1250                1255                1260

GGG CAA TTG GGC ATT CAG CCT TAT TTT GGA GTT AAT CGC TAT TTT ATT        3899
Gly Gln Leu Gly Ile Gln Pro Tyr Phe Gly Val Asn Arg Tyr Phe Ile
1265                1270                1275                1280

GAA CGT GAA AAT TAT CAA TCT GAG GAA GTG AGA GTG AAA ACG CCT AGC        3947
Glu Arg Glu Asn Tyr Gln Ser Glu Glu Val Arg Val Lys Thr Pro Ser
                1285                1290                1295

CTT GCA TTT AAT CGC TAT AAT GCT GGC ATT CGA GTT GAT TAT ACA TTT        3995
Leu Ala Phe Asn Arg Tyr Asn Ala Gly Ile Arg Val Asp Tyr Thr Phe
            1300                1305                1310

ACT CCG ACA GAT AAT ATC AGC GTT AAG CCT TAT TTC TTC GTC AAT TAT        4043
Thr Pro Thr Asp Asn Ile Ser Val Lys Pro Tyr Phe Phe Val Asn Tyr
            1315                1320                1325

GTT GAT GTT TCA AAC GCT AAC GTA CAA ACC ACG GTA AAT CTC ACG GTG        4091
Val Asp Val Ser Asn Ala Asn Val Gln Thr Thr Val Asn Leu Thr Val
            1330                1335                1340

TTG CAA CAA CCA TTT GGA CGT TAT TGG CAA AAA GAA GTG GGA TTA AAG        4139
Leu Gln Gln Pro Phe Gly Arg Tyr Trp Gln Lys Glu Val Gly Leu Lys
1345                1350                1355                1360

GCA GAA ATT TTA CAT TTC CAA ATT TCC GCT TTT ATC TCA AAA TCT CAA        4187
Ala Glu Ile Leu His Phe Gln Ile Ser Ala Phe Ile Ser Lys Ser Gln
            1365                1370                1375

GGT TCA CAA CTC GGC AAA CAG CAA AAT GTG GGC GTG AAA TTG GGC TAT        4235
Gly Ser Gln Leu Gly Lys Gln Gln Asn Val Gly Val Lys Leu Gly Tyr
            1380                1385                1390

CGT TGG TAAAAATCAA CATAATTTTA TCGTTTATTG ATAAACAAGG TGGGTCAGAT         4291
Arg Trp
CAGATCCCAC CTTTTTTATT CCAATAAT                                          4319
```

(2) INFORMATION FOR SEQ ID NO:2:

(i) SEQUENCE CHARACTERISTICS:
        (A) LENGTH: 1394 amino acids
        (B) TYPE: amino acid
        (D) TOPOLOGY: linear (ii) MOLECULE TYPE: protein (xi) SEQUENCE DESCRIPTION: SEQ ID NO:2:

```
Met Lys Lys Thr Val Phe Arg Leu Asn Phe Leu Thr Ala Cys Ile Ser
  1               5                  10                  15

Leu Gly Ile Val Ser Gln Ala Trp Ala Gly His Thr Tyr Phe Gly Ile
                 20                  25                  30

Asp Tyr Gln Tyr Tyr Arg Asp Phe Ala Glu Asn Lys Gly Lys Phe Thr
             35                  40                  45

Val Gly Ala Gln Asn Ile Lys Val Tyr Asn Lys Gln Gly Gln Leu Val
         50                  55                  60

Gly Thr Ser Met Thr Lys Ala Pro Met Ile Asp Phe Ser Val Val Ser
 65                  70                  75                  80

Arg Asn Gly Val Ala Ala Leu Val Glu Asn Gln Tyr Ile Val Ser Val
```

-continued

```
                        85                      90                      95
Ala His Asn Val Gly Tyr Thr Asp Val Asp Phe Gly Ala Glu Gly Asn
                    100                     105                     110
Asn Pro Asp Gln His Arg Phe Thr Tyr Lys Ile Val Lys Arg Asn Asn
                    115                     120                     125
Tyr Lys Lys Asp Asn Leu His Pro Tyr Glu Asp Tyr His Asn Pro
            130                     135                     140
Arg Leu His Lys Phe Val Thr Glu Ala Ala Pro Ile Asp Met Thr Ser
145                     150                     155                     160
Asn Met Asn Gly Ser Thr Tyr Ser Asp Arg Thr Lys Tyr Pro Glu Arg
                    165                     170                     175
Val Arg Ile Gly Ser Gly Arg Gln Phe Trp Arg Asn Asp Gln Asp Lys
                    180                     185                     190
Gly Asp Gln Val Ala Gly Ala Tyr His Tyr Leu Thr Ala Gly Asn Thr
                    195                     200                     205
His Asn Gln Arg Gly Ala Gly Asn Gly Tyr Ser Tyr Leu Gly Gly Asp
            210                     215                     220
Val Arg Lys Ala Gly Glu Tyr Gly Pro Leu Pro Ile Ala Gly Ser Lys
225                     230                     235                     240
Gly Asp Ser Gly Ser Pro Met Phe Ile Tyr Asp Ala Glu Lys Gln Lys
                    245                     250                     255
Trp Leu Ile Asn Gly Ile Leu Arg Glu Gly Asn Pro Phe Glu Gly Lys
                    260                     265                     270
Glu Asn Gly Phe Gln Leu Val Arg Lys Ser Tyr Phe Asp Glu Ile Phe
            275                     280                     285
Glu Arg Asp Leu His Thr Ser Leu Tyr Thr Arg Ala Gly Asn Gly Val
            290                     295                     300
Tyr Thr Ile Ser Gly Asn Asp Asn Gly Gln Gly Ser Ile Thr Gln Lys
305                     310                     315                     320
Ser Gly Ile Pro Ser Glu Ile Lys Ile Thr Leu Ala Asn Met Ser Leu
                    325                     330                     335
Pro Leu Lys Glu Lys Asp Lys Val His Asn Pro Arg Tyr Asp Gly Pro
            340                     345                     350
Asn Ile Tyr Ser Pro Arg Leu Asn Asn Gly Glu Thr Leu Tyr Phe Met
            355                     360                     365
Asp Gln Lys Gln Gly Ser Leu Ile Phe Ala Ser Asp Ile Asn Gln Gly
    370                     375                     380
Ala Gly Gly Leu Tyr Phe Glu Gly Asn Phe Thr Val Ser Pro Asn Ser
385                     390                     395                     400
Asn Gln Thr Trp Gln Gly Ala Gly Ile His Val Ser Glu Asn Ser Thr
                    405                     410                     415
Val Thr Trp Lys Val Asn Gly Val Glu His Asp Arg Leu Ser Lys Ile
                    420                     425                     430
Gly Lys Gly Thr Leu His Val Gln Ala Lys Gly Glu Asn Lys Gly Ser
            435                     440                     445
Ile Ser Val Gly Asp Gly Lys Val Ile Leu Glu Gln Ala Asp Asp
            450                     455                     460
Gln Gly Asn Lys Gln Ala Phe Ser Glu Ile Gly Leu Val Ser Gly Arg
465                     470                     475                     480
Gly Thr Val Gln Leu Asn Asp Asp Lys Gln Phe Asp Thr Asp Lys Phe
                    485                     490                     495
Tyr Phe Gly Phe Arg Gly Gly Arg Leu Asp Leu Asn Gly His Ser Leu
                    500                     505                     510
```

-continued

```
Thr Phe Lys Arg Ile Gln Asn Thr Asp Glu Gly Ala Met Ile Val Asn
        515                 520                 525
His Asn Thr Thr Gln Ala Ala Asn Val Thr Ile Thr Gly Asn Glu Ser
        530                 535                 540
Ile Val Leu Pro Asn Gly Asn Asn Ile Asn Lys Leu Asp Tyr Arg Lys
545                 550                 555                 560
Glu Ile Ala Tyr Asn Gly Trp Phe Gly Glu Thr Asp Lys Asn Lys His
                565                 570                 575
Asn Gly Arg Leu Asn Leu Ile Tyr Lys Pro Thr Thr Glu Asp Arg Thr
            580                 585                 590
Leu Leu Leu Ser Gly Gly Thr Asn Leu Lys Gly Asp Ile Thr Gln Thr
            595                 600                 605
Lys Gly Lys Leu Phe Phe Ser Gly Arg Pro Thr Pro His Ala Tyr Asn
    610                 615                 620
His Leu Asn Lys Arg Trp Ser Glu Met Glu Gly Ile Pro Gln Gly Glu
    625                 630                 635                 640
Ile Val Trp Asp His Asp Trp Ile Asn Arg Thr Phe Lys Ala Glu Asn
                645                 650                 655
Phe Gln Ile Lys Gly Gly Ser Ala Val Val Ser Arg Asn Val Ser Ser
            660                 665                 670
Ile Glu Gly Asn Trp Thr Val Ser Asn Asn Ala Asn Ala Thr Phe Gly
            675                 680                 685
Val Val Pro Asn Gln Gln Asn Thr Ile Cys Thr Arg Ser Asp Trp Thr
        690                 695                 700
Gly Leu Thr Thr Cys Gln Lys Val Asp Leu Thr Asp Thr Lys Val Ile
705                 710                 715                 720
Asn Ser Ile Pro Lys Thr Gln Ile Asn Gly Ser Ile Asn Leu Thr Asp
                725                 730                 735
Asn Ala Thr Ala Asn Val Lys Gly Leu Ala Lys Leu Asn Gly Asn Val
            740                 745                 750
Thr Leu Thr Asn His Ser Gln Phe Thr Leu Ser Asn Asn Ala Thr Gln
            755                 760                 765
Ile Gly Asn Ile Arg Leu Ser Asp Asn Ser Thr Ala Thr Val Asp Asn
    770                 775                 780
Ala Asn Leu Asn Gly Asn Val His Leu Thr Asp Ser Ala Gln Phe Ser
785                 790                 795                 800
Leu Lys Asn Ser His Phe Ser His Gln Ile Gln Gly Asp Lys Gly Thr
                805                 810                 815
Thr Val Thr Leu Glu Asn Ala Thr Trp Thr Met Pro Ser Asp Thr Thr
            820                 825                 830
Leu Gln Asn Leu Thr Leu Asn Asn Ser Thr Ile Thr Leu Asn Ser Ala
            835                 840                 845
Tyr Ser Ala Ser Ser Asn Asn Thr Pro Arg Arg Ser Leu Glu Thr
    850                 855                 860
Glu Thr Thr Pro Thr Ser Ala Glu His Arg Phe Asn Thr Leu Thr Val
865                 870                 875                 880
Asn Gly Lys Leu Ser Gly Gln Gly Thr Phe Gln Phe Thr Ser Ser Leu
                885                 890                 895
Phe Gly Tyr Lys Ser Asp Lys Leu Lys Leu Ser Asn Asp Ala Glu Gly
            900                 905                 910
Asp Tyr Ile Leu Ser Val Arg Asn Thr Gly Lys Glu Pro Glu Thr Leu
            915                 920                 925
```

```
Glu Gln Leu Thr Leu Val Glu Ser Lys Asp Asn Gln Pro Leu Ser Asp
    930                 935                 940

Lys Leu Lys Phe Thr Leu Glu Asn Asp His Val Asp Ala Gly Ala Leu
945                 950                 955                 960

Arg Tyr Lys Leu Val Lys Asn Asp Gly Glu Phe Arg Leu His Asn Pro
                965                 970                 975

Ile Lys Glu Gln Glu Leu His Asn Asp Leu Val Arg Ala Glu Gln Ala
                980                 985                 990

Glu Arg Thr Leu Glu Ala Lys Gln Val Glu Pro Thr Ala Lys Thr Gln
                995                1000                1005

Thr Gly Glu Pro Lys Val Arg Ser Arg Arg Ala Ala Arg Ala Ala Phe
        1010                1015                1020

Pro Asp Thr Leu Pro Asp Gln Ser Leu Leu Asn Ala Leu Glu Ala Lys
1025                1030                1035                1040

Gln Ala Glu Leu Thr Ala Glu Thr Gln Lys Ser Lys Ala Lys Thr Lys
                1045                1050                1055

Lys Val Arg Ser Lys Arg Ala Val Phe Ser Asp Pro Leu Leu Asp Gln
                1060                1065                1070

Ser Leu Phe Ala Leu Glu Ala Ala Leu Glu Val Ile Asp Ala Pro Gln
        1075                1080                1085

Gln Ser Glu Lys Asp Arg Leu Ala Gln Glu Ala Glu Lys Gln Arg
        1090                1095                1100

Lys Gln Lys Asp Leu Ile Ser Arg Tyr Ser Asn Ser Ala Leu Ser Glu
1105                1110                1115                1120

Leu Ser Ala Thr Val Asn Ser Met Leu Ser Val Gln Asp Glu Leu Asp
                1125                1130                1135

Arg Leu Phe Val Asp Gln Ala Gln Ser Ala Val Trp Thr Asn Ile Ala
                1140                1145                1150

Gln Asp Lys Arg Arg Tyr Asp Ser Asp Ala Phe Arg Ala Tyr Gln Gln
                1155                1160                1165

Gln Lys Thr Asn Leu Arg Gln Ile Gly Val Gln Lys Ala Leu Ala Asn
        1170                1175                1180

Gly Arg Ile Gly Ala Val Phe Ser His Ser Arg Ser Asp Asn Thr Phe
1185                1190                1195                1200

Asp Glu Gln Val Lys Asn His Ala Thr Leu Thr Met Met Ser Gly Phe
                1205                1210                1215

Ala Gln Tyr Gln Trp Gly Asp Leu Gln Phe Gly Val Asn Val Gly Thr
                1220                1225                1230

Gly Ile Ser Ala Ser Lys Met Ala Glu Glu Gln Ser Arg Lys Ile His
        1235                1240                1245

Arg Lys Ala Ile Asn Tyr Gly Val Asn Ala Ser Tyr Gln Phe Arg Leu
        1250                1255                1260

Gly Gln Leu Gly Ile Gln Pro Tyr Phe Gly Val Asn Arg Tyr Phe Ile
1265                1270                1275                1280

Glu Arg Glu Asn Tyr Gln Ser Glu Glu Val Arg Val Lys Thr Pro Ser
                1285                1290                1295

Leu Ala Phe Asn Arg Tyr Asn Ala Gly Ile Arg Val Asp Tyr Thr Phe
                1300                1305                1310

Thr Pro Thr Asp Asn Ile Ser Val Lys Pro Tyr Phe Phe Val Asn Tyr
                1315                1320                1325

Val Asp Val Ser Asn Ala Asn Val Gln Thr Thr Val Asn Leu Thr Val
        1330                1335                1340

Leu Gln Gln Pro Phe Gly Arg Tyr Trp Gln Lys Glu Val Gly Leu Lys
```

```
     1345                1350                1355                1360

Ala Glu Ile Leu His Phe Gln Ile Ser Ala Phe Ile Ser Lys Ser Gln
                    1365                1370                1375

Gly Ser Gln Leu Gly Lys Gln Gln Asn Val Gly Val Lys Leu Gly Tyr
                    1380                1385                1390

Arg Trp (2) INFORMATION FOR SEQ ID NO:3:

(i) SEQUENCE CHARACTERISTICS:
          (A) LENGTH: 1541 amino acids
          (B) TYPE: amino acid
          (D) TOPOLOGY: unknown (xi) SEQUENCE DESCRIPTION: SEQ ID NO:3:

Met Leu Asn Lys Lys Phe Lys Leu Asn Phe Ile Ala Leu Thr Val Ala
1               5                   10                  15

Tyr Ala Leu Thr Pro Tyr Thr Glu Ala Ala Leu Val Arg Asp Asp Val
                20                  25                  30

Asp Tyr Gln Ile Phe Arg Asp Phe Ala Glu Asn Lys Gly Lys Phe Ser
            35                  40                  45

Val Gly Ala Thr Asn Val Leu Val Lys Asp Lys Asn Asn Lys Asp Leu
50                  55                  60

Gly Thr Ala Leu Pro Asn Gly Ile Pro Met Ile Asp Phe Ser Val Val
65                  70                  75                  80

Asp Val Asp Lys Arg Ile Ala Thr Leu Ile Asn Pro Gln Tyr Val Val
                85                  90                  95

Gly Val Lys His Val Ser Asn Gly Val Ser Glu Leu His Phe Gly Asn
                100                 105                 110

Leu Asn Gly Asn Met Asn Asn Gly Asn Ala Lys Ala His Arg Asp Val
            115                 120                 125

Ser Ser Glu Glu Asn Arg Tyr Phe Ser Val Glu Lys Asn Glu Tyr Pro
130                 135                 140

Thr Lys Leu Asn Gly Lys Thr Val Thr Thr Glu Asp Gln Thr Gln Lys
145                 150                 155                 160

Arg Arg Glu Asp Tyr Tyr Met Pro Arg Leu Asp Lys Phe Val Thr Glu
                165                 170                 175

Val Ala Pro Ile Glu Ala Ser Thr Ala Ser Ser Asp Ala Gly Thr Tyr
            180                 185                 190

Asn Asp Gln Asn Lys Tyr Pro Ala Phe Val Arg Leu Gly Ser Gly Ser
            195                 200                 205

Gln Phe Ile Tyr Lys Lys Gly Asp Asn Tyr Ser Leu Ile Leu Asn Asn
            210                 215                 220

His Glu Val Gly Gly Asn Asn Leu Lys Leu Val Gly Asp Ala Tyr Thr
225                 230                 235                 240

Tyr Gly Ile Ala Gly Thr Pro Tyr Lys Val Asn His Glu Asn Asn Gly
                245                 250                 255

Leu Ile Gly Phe Gly Asn Ser Lys Glu Glu His Ser Asp Pro Lys Gly
                260                 265                 270

Ile Leu Ser Gln Asp Pro Leu Thr Asn Tyr Ala Val Leu Gly Asp Ser
            275                 280                 285

Gly Ser Pro Leu Phe Val Tyr Asp Arg Glu Lys Gly Lys Trp Leu Phe
            290                 295                 300

Leu Gly Ser Tyr Asp Phe Trp Ala Gly Tyr Asn Lys Lys Ser Trp Gln
305                 310                 315                 320
```

-continued

```
Glu Trp Asn Ile Tyr Lys Ser Gln Phe Thr Lys Asp Val Leu Asn Lys
            325                 330                 335
Asp Ser Ala Gly Ser Leu Ile Gly Ser Lys Thr Asp Tyr Ser Trp Ser
        340                 345                 350
Ser Asn Gly Lys Thr Ser Thr Ile Thr Gly Gly Glu Lys Ser Leu Asn
            355                 360                 365
Val Asp Leu Ala Asp Gly Lys Asp Lys Pro Asn His Gly Lys Ser Val
        370                 375                 380
Thr Phe Glu Gly Ser Gly Thr Leu Thr Leu Asn Asn Asn Ile Asp Gln
385                 390                 395                 400
Gly Ala Gly Gly Leu Phe Phe Glu Gly Asp Tyr Glu Val Lys Gly Thr
                405                 410                 415
Ser Asp Asn Thr Thr Trp Lys Gly Ala Gly Val Ser Val Ala Glu Gly
                420                 425                 430
Lys Thr Val Thr Trp Lys Val His Asn Pro Gln Tyr Asp Arg Leu Ala
            435                 440                 445
Lys Ile Gly Lys Gly Thr Leu Ile Val Glu Gly Thr Gly Asp Asn Lys
        450                 455                 460
Gly Ser Leu Lys Val Gly Asp Gly Thr Val Ile Leu Lys Gln Gln Thr
465                 470                 475                 480
Asn Gly Ser Gly Gln His Ala Phe Ala Ser Val Gly Ile Val Ser Gly
                485                 490                 495
Arg Ser Thr Leu Val Leu Asn Asp Asp Lys Gln Val Asp Pro Asn Ser
                500                 505                 510
Ile Tyr Phe Gly Phe Arg Gly Gly Arg Leu Asp Leu Asn Gly Asn Ser
            515                 520                 525
Leu Thr Phe Asp His Ile Arg Asn Ile Asp Asp Gly Ala Arg Leu Val
        530                 535                 540
Asn His Asn Met Thr Asn Ala Ser Asn Ile Thr Ile Thr Gly Glu Ser
545                 550                 555                 560
Leu Ile Thr Asp Pro Asn Thr Ile Thr Pro Tyr Asn Ile Asp Ala Pro
                565                 570                 575
Asp Glu Asp Asn Pro Tyr Ala Phe Arg Arg Ile Lys Asp Gly Gly Gln
                580                 585                 590
Leu Tyr Leu Asn Leu Glu Asn Tyr Thr Tyr Tyr Ala Leu Arg Lys Gly
            595                 600                 605
Ala Ser Thr Arg Ser Glu Leu Pro Lys Asn Ser Gly Glu Ser Asn Glu
        610                 615                 620
Asn Trp Leu Tyr Met Gly Lys Thr Ser Asp Glu Ala Lys Arg Asn Val
625                 630                 635                 640
Met Asn His Ile Asn Asn Glu Arg Met Asn Gly Phe Asn Gly Tyr Phe
                645                 650                 655
Gly Glu Glu Glu Gly Lys Asn Asn Gly Asn Leu Asn Val Thr Phe Lys
                660                 665                 670
Gly Lys Ser Glu Gln Asn Arg Phe Leu Leu Thr Gly Gly Thr Asn Leu
            675                 680                 685
Asn Gly Asp Leu Thr Val Glu Lys Gly Thr Leu Phe Leu Ser Gly Arg
        690                 695                 700
Pro Thr Pro His Ala Arg Asp Ile Ala Gly Ile Ser Ser Thr Lys Lys
705                 710                 715                 720
Asp Pro His Phe Ala Glu Asn Asn Glu Val Val Glu Asp Asp Trp
                725                 730                 735
```

-continued

```
Ile Asn Arg Asn Phe Lys Ala Thr Thr Met Asn Val Thr Gly Asn Ala
            740                 745                 750

Ser Leu Tyr Ser Gly Arg Asn Val Ala Asn Ile Thr Ser Asn Ile Thr
            755                 760                 765

Ala Ser Asn Lys Ala Gln Val His Ile Gly Tyr Lys Thr Gly Asp Thr
            770                 775                 780

Val Cys Val Arg Ser Asp Tyr Thr Gly Tyr Val Thr Cys Thr Thr Asp
785                 790                 795                 800

Lys Leu Ser Asp Lys Ala Leu Asn Ser Phe Asn Pro Thr Asn Leu Arg
            805                 810                 815

Gly Asn Val Asn Leu Thr Glu Ser Ala Asn Phe Val Leu Gly Lys Ala
            820                 825                 830

Asn Leu Phe Gly Thr Ile Gln Ser Arg Gly Asn Ser Gln Val Arg Leu
            835                 840                 845

Thr Glu Asn Ser His Trp His Leu Thr Gly Asn Ser Asp Val His Gln
            850                 855                 860

Leu Asp Leu Ala Asn Gly His Ile His Leu Asn Ser Ala Asp Asn Ser
865                 870                 875                 880

Asn Asn Val Thr Lys Tyr Asn Thr Leu Thr Val Asn Ser Leu Ser Gly
            885                 890                 895

Asn Gly Ser Phe Tyr Tyr Leu Thr Asp Leu Ser Asn Lys Gln Gly Asp
            900                 905                 910

Lys Val Val Thr Lys Ser Ala Thr Gly Asn Phe Thr Leu Gln Val
            915                 920                 925

Ala Asp Lys Thr Gly Glu Pro Asn His Asn Glu Leu Thr Leu Phe Asp
            930                 935                 940

Ala Ser Lys Ala Gln Arg Asp His Leu Asn Val Ser Leu Val Gly Asn
945                 950                 955                 960

Thr Val Asp Leu Gly Ala Trp Lys Tyr Lys Leu Arg Asn Val Asn Gly
            965                 970                 975

Arg Tyr Asp Leu Tyr Asn Pro Glu Val Glu Lys Arg Asn Gln Thr Val
            980                 985                 990

Asp Thr Thr Asn Ile Thr Thr Pro Asn Asn Ile Gln Ala Asp Val Pro
            995                 1000                1005

Ser Val Pro Ser Asn Asn Glu Glu Ile Ala Arg Val Asp Glu Ala Pro
            1010                1015                1020

Val Pro Pro Ala Pro Ala Thr Pro Ser Glu Thr Thr Glu Thr Val
1025                1030                1035                1040

Ala Glu Asn Ser Lys Gln Glu Ser Lys Thr Val Glu Lys Asn Glu Gln
            1045                1050                1055

Asp Ala Thr Glu Thr Thr Ala Gln Asn Arg Glu Val Ala Lys Glu Ala
            1060                1065                1070

Lys Ser Asn Val Lys Ala Asn Thr Gln Thr Asn Glu Val Ala Gln Ser
            1075                1080                1085

Gly Ser Glu Thr Lys Glu Thr Gln Thr Thr Glu Thr Ala
            1090                1095                1100

Thr Val Glu Lys Glu Glu Lys Ala Lys Val Glu Thr Glu Lys Thr Gln
1105                1110                1115                1120

Glu Val Pro Lys Val Thr Ser Gln Val Ser Pro Lys Gln Glu Gln Ser
            1125                1130                1135

Glu Thr Val Gln Pro Gln Ala Gly Pro Ala Arg Glu Asn Asp Pro Thr
            1140                1145                1150

Val Asn Ile Lys Glu Pro Gln Ser Gln Thr Asn Thr Thr Ala Asp Thr
```

```
              1155           1160              1165
Glu Gln Pro Ala Lys Glu Thr Ser Ser Asn Val Gln Pro Val Thr
1170           1175              1180
Glu Ser Thr Thr Val Asn Thr Gly Asn Ser Val Val Glu Asn Pro Glu
1185           1190              1195              1200
Asn Thr Thr Pro Ala Thr Thr Gln Pro Thr Val Asn Ser Glu Ser Ser
              1205              1210              1215
Asn Lys Pro Lys Asn Arg His Arg Arg Ser Val Arg Ser Val Pro His
              1220              1225              1230
Asn Val Glu Pro Ala Thr Thr Ser Ser Asn Asp Arg Ser Thr Val Ala
              1235              1240              1245
Leu Cys Asp Leu Thr Ser Thr Asn Thr Asn Ala Val Leu Ser Asp Ala
              1250              1255              1260
Arg Ala Lys Ala Gln Phe Val Ala Leu Asn Val Gly Lys Ala Val Ser
1265              1270              1275              1280
Gln His Ile Ser Gln Leu Glu Met Asn Asn Glu Gly Gln Tyr Asn Val
              1285              1290              1295
Trp Val Ser Asn Thr Ser Met Asn Lys Asn Tyr Ser Ser Ser Gln Tyr
              1300              1305              1310
Arg Arg Phe Ser Ser Lys Ser Thr Gln Thr Gln Leu Gly Trp Asp Gln
              1315              1320              1325
Thr Ile Ser Asn Asn Val Gln Leu Gly Gly Val Phe Thr Tyr Val Arg
              1330              1335              1340
Asn Ser Asn Asn Phe Asp Lys Ala Thr Ser Lys Asn Thr Leu Ala Gln
1345              1350              1355              1360
Val Asn Phe Tyr Ser Lys Tyr Tyr Ala Asp Asn His Trp Tyr Leu Gly
              1365              1370              1375
Ile Asp Leu Gly Tyr Gly Lys Phe Gln Ser Lys Leu Gln Thr Asn His
              1380              1385              1390
Asn Ala Lys Phe Ala Arg His Thr Ala Gln Phe Gly Leu Thr Ala Gly
              1395              1400              1405
Lys Ala Phe Asn Leu Gly Asn Phe Gly Ile Thr Pro Ile Val Gly Val
              1410              1415              1420
Arg Tyr Ser Tyr Leu Ser Asn Ala Asp Phe Ala Leu Asp Gln Ala Arg
1425              1430              1435              1440
Ile Lys Val Asn Pro Ile Ser Val Lys Thr Ala Phe Ala Gln Val Asp
              1445              1450              1455
Leu Ser Tyr Thr Tyr His Leu Gly Glu Phe Ser Val Thr Pro Ile Leu
              1460              1465              1470
Ser Ala Arg Tyr Asp Ala Asn Gln Gly Ser Gly Lys Ile Asn Val Asn
              1475              1480              1485
Gly Tyr Asp Phe Ala Tyr Asn Val Glu Asn Gln Gln Tyr Asn Ala
              1490              1495              1500
Gly Leu Lys Leu Lys Tyr His Asn Val Lys Leu Ser Leu Ile Gly Gly
1505              1510              1515              1520
Leu Thr Lys Ala Lys Gln Ala Glu Lys Gln Lys Thr Ala Glu Leu Lys
              1525              1530              1535
Leu Ser Phe Ser Phe
              1540

(2) INFORMATION FOR SEQ ID NO:4:

(i) SEQUENCE CHARACTERISTICS:
       (A) LENGTH: 1545 amino acids
```

(B) TYPE: amino acid
(D) TOPOLOGY: unknown (xi) SEQUENCE DESCRIPTION: SEQ ID NO:4:

```
Met Leu Asn Lys Lys Phe Lys Leu Asn Phe Ile Ala Leu Thr Val Ala
1               5                   10                  15

Tyr Ala Leu Thr Pro Tyr Thr Glu Ala Ala Leu Val Arg Asp Asp Val
                20                  25                  30

Asp Tyr Gln Ile Phe Arg Asp Phe Ala Glu Asn Lys Gly Lys Phe Ser
                35                  40                  45

Val Gly Ala Thr Asn Val Glu Val Arg Asp Lys Asn Asn Arg Pro Leu
        50                  55                  60

Gly Asn Val Leu Pro Asn Gly Ile Pro Met Ile Asp Phe Ser Val Val
65                  70                  75                  80

Asp Val Asp Lys Arg Ile Ala Thr Leu Val Asn Pro Gln Tyr Val Val
                85                  90                  95

Gly Val Lys His Val Ser Asn Gly Val Ser Glu Leu His Phe Gly Asn
                100                 105                 110

Leu Asn Gly Asn Met Asn Asn Gly Asn Ala Lys Ala His Arg Asp Val
                115                 120                 125

Ser Ser Glu Glu Asn Arg Tyr Tyr Thr Val Lys Asn Glu Tyr Pro
130                 135                 140

Thr Lys Leu Asn Gly Lys Ala Val Thr Thr Glu Asp Gln Ala Gln Lys
145                 150                 155                 160

Arg Arg Glu Asp Tyr Tyr Met Pro Arg Leu Asp Lys Phe Val Thr Glu
                165                 170                 175

Val Ala Pro Ile Glu Ala Ser Thr Asp Ser Ser Thr Ala Gly Thr Tyr
                180                 185                 190

Asn Asn Lys Asp Lys Tyr Pro Tyr Phe Val Arg Leu Gly Ser Gly Thr
                195                 200                 205

Gln Phe Ile Tyr Glu Asn Gly Thr Arg Tyr Glu Leu Trp Leu Gly Lys
                210                 215                 220

Glu Gly Gln Lys Ser Asp Ala Gly Gly Tyr Asn Leu Lys Leu Val Gly
225                 230                 235                 240

Asn Ala Tyr Thr Tyr Gly Ile Ala Gly Thr Pro Tyr Glu Val Asn His
                245                 250                 255

Glu Asn Asp Gly Leu Ile Gly Phe Gly Asn Ser Asn Glu Tyr Ile
                260                 265                 270

Asn Pro Lys Glu Ile Leu Ser Lys Pro Leu Thr Asn Tyr Ala Val
                275                 280                 285

Leu Gly Asp Ser Gly Ser Pro Leu Phe Val Tyr Asp Arg Glu Lys Gly
                290                 295                 300

Lys Trp Leu Phe Leu Gly Ser Tyr Asp Tyr Trp Ala Gly Tyr Asn Lys
305                 310                 315                 320

Lys Ser Trp Gln Glu Trp Asn Ile Tyr Lys Pro Glu Phe Ala Glu Lys
                325                 330                 335

Ile Tyr Glu Gln Tyr Ser Ala Gly Ser Leu Ile Gly Ser Lys Thr Asp
                340                 345                 350

Tyr Ser Trp Ser Ser Asn Gly Lys Thr Ser Thr Ile Thr Gly Gly Glu
                355                 360                 365

Lys Ser Leu Asn Val Asp Leu Ala Asp Gly Lys Asp Lys Pro Asn His
                370                 375                 380

Gly Lys Ser Val Thr Phe Glu Gly Ser Gly Thr Leu Thr Leu Asn Asn
385                 390                 395                 400
```

```
Asn Ile Asp Gln Gly Ala Gly Gly Leu Phe Phe Glu Gly Asp Tyr Glu
                405                 410                 415
Val Lys Gly Thr Ser Asp Asn Thr Thr Trp Lys Gly Ala Gly Val Ser
            420                 425                 430
Val Ala Glu Gly Lys Thr Val Thr Trp Lys Val His Asn Pro Gln Tyr
            435                 440                 445
Asp Arg Leu Ala Lys Ile Gly Lys Gly Thr Leu Ile Val Glu Gly Thr
        450                 455                 460
Gly Asp Asn Lys Gly Ser Leu Lys Val Gly Asp Gly Thr Val Ile Leu
465                 470                 475                 480
Lys Gln Gln Thr Asn Gly Ser Gly Gln His Ala Phe Ala Ser Val Gly
            485                 490                 495
Ile Val Ser Gly Arg Ser Thr Leu Val Leu Asn Asp Asp Lys Gln Val
                500                 505                 510
Asp Pro Asn Ser Ile Tyr Phe Gly Phe Arg Gly Gly Arg Leu Asp Leu
            515                 520                 525
Asn Gly Asn Ser Leu Thr Phe Asp His Ile Arg Asn Ile Asp Glu Gly
        530                 535                 540
Ala Arg Leu Val Asn His Ser Thr Ser Lys His Ser Thr Val Thr Ile
545                 550                 555                 560
Thr Gly Asp Asn Leu Ile Thr Asp Pro Asn Asn Val Ser Ile Tyr Tyr
                565                 570                 575
Val Lys Pro Leu Glu Asp Asp Asn Pro Tyr Ala Ile Arg Gln Ile Lys
            580                 585                 590
Tyr Gly Tyr Gln Leu Tyr Phe Asn Glu Glu Asn Arg Thr Tyr Tyr Ala
        595                 600                 605
Leu Lys Lys Asp Ala Ser Ile Arg Ser Glu Phe Pro Gln Asn Arg Gly
610                 615                 620
Glu Ser Asn Asn Ser Trp Leu Tyr Met Gly Thr Glu Lys Ala Asp Ala
625                 630                 635                 640
Gln Lys Asn Ala Met Asn His Ile Asn Asn Glu Arg Met Asn Gly Phe
            645                 650                 655
Asn Gly Tyr Phe Gly Glu Glu Glu Lys Asn Asn Gly Asn Leu Asn
                660                 665                 670
Val Thr Phe Lys Gly Lys Ser Glu Gln Asn Arg Phe Leu Leu Thr Gly
            675                 680                 685
Gly Thr Asn Leu Asn Gly Asp Leu Asn Val Gln Gln Gly Thr Leu Phe
        690                 695                 700
Leu Ser Gly Arg Pro Thr Pro His Ala Arg Asp Ile Ala Gly Ile Ser
705                 710                 715                 720
Ser Thr Lys Lys Asp Ser His Phe Ser Glu Asn Asn Glu Val Val Val
            725                 730                 735
Glu Asp Asp Trp Ile Asn Arg Asn Phe Lys Ala Thr Asn Ile Asn Val
                740                 745                 750
Thr Asn Asn Ala Thr Leu Tyr Ser Gly Arg Asn Val Glu Ser Ile Thr
            755                 760                 765
Ser Asn Ile Thr Ala Ser Asn Asn Ala Lys Val His Ile Gly Tyr Lys
        770                 775                 780
Ala Gly Asp Thr Val Cys Val Arg Ser Asp Tyr Thr Gly Tyr Val Thr
785                 790                 795                 800
Cys Thr Thr Asp Lys Leu Ser Asp Lys Ala Leu Asn Ser Phe Asn Pro
                805                 810                 815
```

-continued

```
Thr Asn Leu Arg Gly Asn Val Asn Leu Thr Glu Ser Ala Asn Phe Val
        820                 825                 830

Leu Gly Lys Ala Asn Leu Phe Gly Thr Ile Gln Ser Arg Gly Asn Ser
        835                 840                 845

Gln Val Arg Leu Thr Glu Asn Ser His Trp His Leu Thr Gly Asn Ser
        850                 855                 860

Asp Val His Gln Leu Asp Leu Ala Asn Gly His Ile His Leu Asn Ser
865                 870                 875                 880

Ala Asp Asn Ser Asn Asn Val Thr Lys Tyr Asn Thr Leu Thr Val Asn
                885                 890                 895

Ser Leu Ser Gly Asn Gly Ser Phe Tyr Tyr Leu Thr Asp Leu Ser Asn
                900                 905                 910

Lys Gln Gly Asp Lys Val Val Thr Lys Ser Ala Thr Gly Asn Phe
        915                 920                 925

Thr Leu Gln Val Ala Asp Lys Thr Gly Glu Pro Asn His Asn Glu Leu
        930                 935                 940

Thr Leu Phe Asp Ala Ser Lys Ala Gln Arg Asp His Leu Asn Val Ser
945                 950                 955                 960

Leu Val Gly Asn Thr Val Asp Leu Gly Ala Trp Lys Tyr Lys Leu Arg
                965                 970                 975

Asn Val Asn Gly Arg Tyr Asp Leu Tyr Asn Pro Glu Val Glu Lys Arg
                980                 985                 990

Asn Gln Thr Val Asp Thr Thr Asn Ile Thr Thr Pro Asn Asn Ile Gln
        995                 1000                1005

Ala Asp Val Pro Ser Val Pro Ser Asn Asn Glu Glu Ile Ala Arg Val
        1010                1015                1020

Asp Glu Ala Pro Val Pro Pro Ala Pro Ala Thr Pro Ser Glu Thr
1025                1030                1035                1040

Thr Glu Thr Val Ala Glu Asn Ser Lys Gln Glu Ser Lys Thr Val Glu
                1045                1050                1055

Lys Asn Glu Gln Asp Ala Thr Glu Thr Thr Ala Gln Asn Arg Glu Val
                1060                1065                1070

Ala Lys Glu Ala Lys Ser Asn Val Lys Ala Asn Thr Gln Thr Asn Glu
        1075                1080                1085

Val Ala Gln Ser Gly Ser Glu Thr Lys Glu Thr Gln Thr Thr Glu Thr
        1090                1095                1100

Lys Glu Thr Ala Thr Val Glu Lys Glu Glu Lys Ala Lys Val Glu Thr
1105                1110                1115                1120

Glu Lys Thr Gln Glu Val Pro Lys Val Thr Ser Gln Val Ser Pro Lys
                1125                1130                1135

Gln Glu Gln Ser Glu Thr Val Gln Pro Gln Ala Glu Pro Ala Arg Glu
                1140                1145                1150

Asn Asp Pro Thr Val Asn Ile Lys Glu Pro Gln Ser Gln Thr Asn Thr
        1155                1160                1165

Thr Ala Asp Thr Glu Gln Pro Ala Lys Glu Thr Ser Ser Asn Val Glu
        1170                1175                1180

Gln Pro Val Thr Glu Ser Thr Thr Val Asn Thr Gly Asn Ser Val Val
1185                1190                1195                1200

Glu Asn Pro Glu Asn Thr Thr Pro Ala Thr Thr Gln Pro Thr Val Asn
                1205                1210                1215

Ser Glu Ser Ser Asn Lys Pro Lys Asn Arg His Arg Arg Ser Val Arg
                1220                1225                1230

Ser Val Pro His Asn Val Glu Pro Ala Thr Thr Ser Ser Asn Asp Arg
```

-continued

```
              1235                1240                1245
Ser Thr Val Ala Leu Cys Asp Leu Thr Ser Thr Asn Thr Asn Ala Val
         1250                1255                1260

Leu Ser Asp Ala Arg Ala Lys Ala Gln Phe Val Ala Leu Asn Val Gly
1265                1270                1275                1280

Lys Ala Val Ser Gln His Ile Ser Gln Leu Glu Met Asn Asn Glu Gly
              1285                1290                1295

Gln Tyr Asn Val Trp Val Ser Asn Thr Ser Met Asn Lys Asn Tyr Ser
         1300                1305                1310

Ser Ser Gln Tyr Arg Arg Phe Ser Ser Lys Ser Thr Gln Thr Gln Leu
    1315                1320                1325

Gly Trp Asp Gln Thr Ile Ser Asn Asn Val Gln Leu Gly Gly Val Phe
   1330                1335                1340

Thr Tyr Val Arg Asn Ser Asn Asn Phe Asp Lys Ala Thr Ser Lys Asn
1345                1350                1355                1360

Thr Leu Ala Gln Val Asn Phe Tyr Ser Lys Tyr Tyr Ala Asp Asn His
              1365                1370                1375

Trp Tyr Leu Gly Ile Asp Leu Gly Tyr Gly Lys Phe Gln Ser Lys Leu
         1380                1385                1390

Gln Thr Asn His Asn Ala Lys Phe Ala Arg His Thr Ala Gln Phe Gly
    1395                1400                1405

Leu Thr Ala Gly Lys Ala Phe Asn Leu Gly Asn Phe Gly Ile Thr Pro
   1410                1415                1420

Ile Val Gly Val Arg Tyr Ser Tyr Leu Ser Asn Ala Asp Phe Ala Leu
1425                1430                1435                1440

Asp Gln Ala Arg Ile Lys Val Asn Pro Ile Ser Val Lys Thr Ala Phe
              1445                1450                1455

Ala Gln Val Asp Leu Ser Tyr Thr Tyr His Leu Gly Glu Phe Ser Val
         1460                1465                1470

Thr Pro Ile Leu Ser Ala Arg Tyr Asp Ala Asn Gln Gly Ser Gly Lys
    1475                1480                1485

Ile Asn Val Asn Gly Tyr Asp Phe Ala Tyr Asn Val Glu Asn Gln Gln
   1490                1495                1500

Gln Tyr Asn Ala Gly Leu Lys Leu Lys Tyr His Asn Val Lys Leu Ser
1505                1510                1515                1520

Leu Ile Gly Gly Leu Thr Lys Ala Lys Gln Ala Glu Lys Gln Lys Thr
              1525                1530                1535

Ala Glu Leu Lys Leu Ser Phe Ser Phe
         1540                1545

(2) INFORMATION FOR SEQ ID NO:5:

(i) SEQUENCE CHARACTERISTICS:
        (A) LENGTH: 1702 amino acids
        (B) TYPE: amino acid
        (D) TOPOLOGY: unknown (xi) SEQUENCE DESCRIPTION: SEQ ID NO:5:

Met Leu Asn Lys Lys Phe Lys Leu Asn Phe Ile Ala Leu Thr Val Ala
1               5                   10                  15

Tyr Ala Leu Thr Pro Tyr Thr Glu Ala Ala Leu Val Arg Asp Asp Val
              20                  25                  30

Asp Tyr Gln Ile Phe Arg Asp Phe Ala Glu Asn Lys Gly Arg Phe Ser
         35                  40                  45

Val Gly Ala Thr Asn Val Glu Val Arg Asp Lys Asn Asn His Ser Leu
```

```
        50                  55                  60
Gly Asn Val Leu Pro Asn Gly Ile Pro Met Ile Asp Phe Ser Val Val
 65                  70                  75                  80

Asp Val Asp Lys Arg Ile Ala Thr Leu Ile Asn Pro Gln Tyr Val Val
                 85                  90                  95

Gly Val Lys His Val Ser Asn Gly Val Ser Glu Leu His Phe Gly Asn
                100                 105                 110

Leu Asn Gly Asn Met Asn Asn Gly Asn Asp Lys Ser His Arg Asp Val
                115                 120                 125

Ser Ser Glu Glu Asn Arg Tyr Phe Ser Val Glu Lys Asn Glu Tyr Pro
130                 135                 140

Thr Lys Leu Asn Gly Lys Ala Val Thr Thr Glu Asp Gln Thr Gln Lys
145                 150                 155                 160

Arg Arg Glu Asp Tyr Tyr Met Pro Arg Leu Asp Lys Phe Val Thr Glu
                165                 170                 175

Val Ala Pro Ile Glu Ala Ser Thr Ala Ser Ser Asp Ala Gly Thr Tyr
                180                 185                 190

Asn Asp Gln Asn Lys Tyr Pro Ala Phe Val Arg Leu Gly Ser Gly Thr
                195                 200                 205

Gln Phe Ile Tyr Lys Lys Gly Asp Asn Tyr Ser Leu Ile Leu Asn Asn
210                 215                 220

His Glu Val Gly Gly Asn Asn Leu Lys Leu Val Gly Asp Ala Tyr Thr
225                 230                 235                 240

Tyr Gly Ile Ala Gly Thr Pro Tyr Lys Val Asn His Glu Asn Asn Gly
                245                 250                 255

Leu Ile Gly Phe Gly Asn Ser Lys Glu Glu His Ser Asp Pro Lys Gly
                260                 265                 270

Ile Leu Ser Gln Asp Pro Leu Thr Asn Tyr Ala Val Leu Gly Asp Ser
                275                 280                 285

Gly Ser Pro Leu Phe Val Tyr Asp Arg Glu Lys Gly Lys Trp Leu Phe
290                 295                 300

Leu Gly Ser Tyr Asp Phe Trp Ala Gly Tyr Asn Lys Lys Ser Trp Gln
305                 310                 315                 320

Glu Trp Asn Ile Tyr Lys Pro Glu Phe Ala Lys Thr Val Leu Asp Lys
                325                 330                 335

Asp Thr Ala Gly Ser Leu Ile Gly Ser Asn Thr Gln Tyr Asn Trp Asn
                340                 345                 350

Pro Thr Gly Lys Thr Ser Val Ile Ser Asn Gly Ser Glu Ser Leu Asn
                355                 360                 365

Val Asp Leu Phe Asp Ser Ser Gln Asp Thr Asp Ser Lys Lys Asn Asn
                370                 375                 380

His Gly Lys Ser Val Thr Leu Arg Gly Ser Gly Thr Leu Thr Leu Asn
385                 390                 395                 400

Asn Asn Ile Asp Gln Gly Ala Gly Gly Leu Phe Phe Glu Gly Asp Tyr
                405                 410                 415

Glu Val Lys Gly Thr Ser Asp Ser Thr Thr Trp Lys Gly Ala Gly Val
                420                 425                 430

Ser Val Ala Asp Gly Lys Thr Val Thr Trp Lys Val His Asn Pro Lys
                435                 440                 445

Ser Asp Arg Leu Ala Lys Ile Gly Lys Gly Thr Leu Ile Val Glu Gly
                450                 455                 460

Lys Gly Glu Asn Lys Gly Ser Leu Lys Val Gly Asp Gly Thr Val Ile
465                 470                 475                 480
```

```
Leu Lys Gln Gln Ala Asp Ala Asn Asn Lys Val Lys Ala Phe Ser Gln
                485                 490                 495
Val Gly Ile Val Ser Gly Arg Ser Thr Val Val Leu Asn Asp Asp Lys
            500                 505                 510
Gln Val Asp Pro Asn Ser Ile Tyr Phe Gly Phe Arg Gly Gly Arg Leu
            515                 520                 525
Asp Ala Asn Gly Asn Asn Leu Thr Phe Glu His Ile Arg Asn Ile Asp
            530                 535                 540
Asp Gly Ala Arg Leu Val Asn His Asn Thr Ser Lys Thr Ser Thr Val
545                 550                 555                 560
Thr Ile Thr Gly Glu Ser Leu Ile Thr Asp Pro Asn Thr Ile Thr Pro
                565                 570                 575
Tyr Asn Ile Asp Ala Pro Asp Glu Asp Asn Pro Tyr Ala Phe Arg Arg
                580                 585                 590
Ile Lys Asp Gly Gly Gln Leu Tyr Leu Asn Leu Glu Asn Tyr Thr Tyr
                595                 600                 605
Tyr Ala Leu Arg Lys Gly Ala Ser Thr Arg Ser Glu Leu Pro Lys Asn
                610                 615                 620
Ser Gly Glu Ser Asn Glu Asn Trp Leu Tyr Met Gly Lys Thr Ser Asp
625                 630                 635                 640
Ala Ala Lys Arg Asn Val Met Asn His Ile Asn Asn Glu Arg Met Asn
                645                 650                 655
Gly Phe Asn Gly Tyr Phe Gly Glu Glu Glu Gly Lys Asn Asn Gly Asn
                660                 665                 670
Leu Asn Val Thr Phe Lys Gly Lys Ser Glu Gln Asn Arg Phe Leu Leu
                675                 680                 685
Thr Gly Gly Thr Asn Leu Asn Gly Asp Leu Lys Val Glu Lys Gly Thr
                690                 695                 700
Leu Phe Leu Ser Gly Arg Pro Thr Pro His Ala Arg Asp Ile Ala Gly
705                 710                 715                 720
Ile Ser Ser Thr Lys Lys Asp Gln His Phe Ala Glu Asn Asn Glu Val
                725                 730                 735
Val Val Glu Asp Asp Trp Ile Asn Arg Asn Phe Lys Ala Thr Asn Ile
                740                 745                 750
Asn Val Thr Asn Asn Ala Thr Leu Tyr Ser Gly Arg Asn Val Ala Asn
                755                 760                 765
Ile Thr Ser Asn Ile Thr Ala Ser Asp Asn Ala Lys Val His Ile Gly
                770                 775                 780
Tyr Lys Ala Gly Asp Thr Val Cys Val Arg Ser Asp Tyr Thr Gly Tyr
785                 790                 795                 800
Val Thr Cys Thr Thr Asp Lys Leu Ser Asp Lys Ala Leu Asn Ser Phe
                805                 810                 815
Asn Ala Thr Asn Val Ser Gly Asn Val Asn Leu Ser Gly Asn Ala Asn
                820                 825                 830
Phe Val Leu Gly Lys Ala Asn Leu Phe Gly Thr Ile Ser Gly Thr Gly
                835                 840                 845
Asn Ser Gln Val Arg Leu Thr Glu Asn Ser His Trp His Leu Thr Gly
                850                 855                 860
Asp Ser Asn Val Asn Gln Leu Asn Leu Asp Lys Gly His Ile His Leu
865                 870                 875                 880
Asn Ala Gln Asn Asp Ala Asn Lys Val Thr Thr Tyr Asn Thr Leu Thr
                885                 890                 895
```

-continued

```
Val Asn Ser Leu Ser Gly Asn Gly Ser Phe Tyr Tyr Leu Thr Asp Leu
            900                 905                 910

Ser Asn Lys Gln Gly Asp Lys Val Val Thr Lys Ser Ala Thr Gly
            915                 920                 925

Asn Phe Thr Leu Gln Val Ala Asp Lys Thr Gly Glu Pro Thr Lys Asn
            930                 935                 940

Glu Leu Thr Leu Phe Asp Ala Ser Asn Ala Thr Arg Asn Asn Leu Asn
945                 950                 955                 960

Val Ser Leu Val Gly Asn Thr Val Asp Leu Gly Ala Trp Lys Tyr Lys
            965                 970                 975

Leu Arg Asn Val Asn Gly Arg Tyr Asp Leu Tyr Asn Pro Glu Val Glu
            980                 985                 990

Lys Arg Asn Gln Thr Val Asp Thr Thr Asn Ile Thr Thr Pro Asn Asn
            995                 1000                1005

Ile Gln Ala Asp Val Pro Ser Val Pro Ser Asn Asn Glu Glu Ile Ala
            1010                1015                1020

Arg Val Glu Thr Pro Val Pro Pro Ala Pro Ala Thr Pro Ser Glu
1025                1030                1035                1040

Thr Thr Glu Thr Val Ala Glu Asn Ser Lys Gln Glu Ser Lys Thr Val
            1045                1050                1055

Glu Lys Asn Glu Gln Asp Ala Thr Glu Thr Thr Ala Gln Asn Gly Glu
            1060                1065                1070

Val Ala Glu Glu Ala Lys Pro Ser Val Lys Ala Asn Thr Gln Thr Asn
            1075                1080                1085

Glu Val Ala Gln Ser Gly Ser Glu Thr Glu Thr Gln Thr Thr Glu
            1090                1095                1100

Ile Lys Glu Thr Ala Lys Val Glu Lys Glu Lys Ala Lys Val Glu
1105                1110                1115                1120

Lys Glu Lys Ala Lys Val Glu Lys Asp Glu Ile Gln Glu Ala Pro
            1125                1130                1135

Gln Met Ala Ser Glu Thr Ser Pro Lys Gln Ala Lys Pro Ala Pro Lys
            1140                1145                1150

Glu Val Ser Thr Asp Thr Lys Val Glu Glu Thr Gln Val Gln Ala Gln
            1155                1160                1165

Pro Gln Thr Gln Ser Thr Thr Val Ala Ala Ala Glu Ala Thr Ser Pro
            1170                1175                1180

Asn Ser Lys Pro Ala Glu Glu Thr Gln Pro Ser Glu Lys Thr Asn Ala
1185                1190                1195                1200

Glu Pro Val Thr Pro Val Val Ser Lys Asn Gln Thr Glu Asn Thr Thr
            1205                1210                1215

Asp Gln Pro Thr Glu Arg Glu Lys Thr Ala Lys Val Glu Thr Glu Lys
            1220                1225                1230

Thr Gln Glu Pro Pro Gln Val Ala Ser Gln Ala Ser Pro Lys Gln Glu
            1235                1240                1245

Gln Ser Glu Thr Val Gln Pro Gln Ala Val Leu Glu Ser Glu Asn Val
            1250                1255                1260

Pro Thr Val Asn Asn Ala Glu Glu Val Gln Ala Gln Leu Gln Thr Gln
1265                1270                1275                1280

Thr Ser Ala Thr Val Ser Thr Lys Gln Pro Ala Pro Glu Asn Ser Ile
            1285                1290                1295

Asn Thr Gly Ser Ala Thr Ala Ile Thr Glu Thr Ala Glu Lys Ser Asp
            1300                1305                1310

Lys Pro Gln Thr Glu Thr Ala Ala Ser Thr Glu Asp Ala Ser Gln His
```

```
            1315                1320                1325
Lys Ala Asn Thr Val Ala Asp Asn Ser Val Ala Asn Asn Ser Glu Ser
            1330                1335                1340

Ser Glu Pro Lys Ser Arg Arg Arg Ser Ile Ser Gln Pro Gln Glu
1345                1350                1355                1360

Thr Ser Ala Glu Glu Thr Thr Ala Ala Ser Thr Asp Glu Thr Thr Ile
            1365                1370                1375

Ala Asp Asn Ser Lys Arg Ser Lys Pro Asn Arg Arg Ser Arg Arg Ser
            1380                1385                1390

Val Arg Ser Glu Pro Thr Val Thr Asn Gly Ser Asp Arg Ser Thr Val
            1395                1400                1405

Ala Leu Arg Asp Leu Thr Ser Thr Asn Thr Asn Ala Val Ile Ser Asp
            1410                1415                1420

Ala Met Ala Lys Ala Gln Phe Val Ala Leu Asn Val Gly Lys Ala Val
1425                1430                1435                1440

Ser Gln His Ile Ser Gln Leu Glu Met Asn Asn Glu Gly Gln Tyr Asn
            1445                1450                1455

Val Trp Val Ser Asn Thr Ser Met Asn Glu Asn Tyr Ser Ser Ser Gln
            1460                1465                1470

Tyr Arg Arg Phe Ser Ser Lys Ser Thr Gln Thr Gln Leu Gly Trp Asp
            1475                1480                1485

Gln Thr Ile Ser Asn Asn Val Gln Leu Gly Gly Val Phe Thr Tyr Val
            1490                1495                1500

Arg Asn Ser Asn Asn Phe Asp Lys Ala Ser Ser Lys Asn Thr Leu Ala
1505                1510                1515                1520

Gln Val Asn Phe Tyr Ser Lys Tyr Tyr Ala Asp Asn His Trp Tyr Leu
            1525                1530                1535

Gly Ile Asp Leu Gly Tyr Gly Lys Phe Gln Ser Asn Leu Lys Thr Asn
            1540                1545                1550

His Asn Ala Lys Phe Ala Arg His Thr Ala Gln Phe Gly Leu Thr Ala
            1555                1560                1565

Gly Lys Ala Phe Asn Leu Gly Asn Phe Gly Ile Thr Pro Ile Val Gly
            1570                1575                1580

Val Arg Tyr Ser Tyr Leu Ser Asn Ala Asn Phe Ala Leu Ala Lys Asp
1585                1590                1595                1600

Arg Ile Lys Val Asn Pro Ile Ser Val Lys Thr Ala Phe Ala Gln Val
            1605                1610                1615

Asp Leu Ser Tyr Thr Tyr His Leu Gly Glu Phe Ser Val Thr Pro Ile
            1620                1625                1630

Leu Ser Ala Arg Tyr Asp Thr Asn Gln Gly Ser Gly Lys Ile Asn Val
            1635                1640                1645

Asn Gln Tyr Asp Phe Ala Tyr Asn Val Glu Asn Gln Gln Tyr Asn
            1650                1655                1660

Ala Gly Leu Lys Leu Lys Tyr His Asn Val Lys Leu Ser Leu Ile Gly
1665                1670                1675                1680

Gly Leu Thr Lys Ala Lys Gln Ala Glu Lys Gln Lys Thr Ala Glu Leu
            1685                1690                1695

Lys Leu Ser Phe Ser Phe
            1700

(2) INFORMATION FOR SEQ ID NO:6:

(i) SEQUENCE CHARACTERISTICS:
        (A) LENGTH: 1848 amino acids
```

(B) TYPE: amino acid
(D) TOPOLOGY: unknown (xi) SEQUENCE DESCRIPTION: SEQ ID NO:6:

```
Met Leu Asn Lys Lys Phe Lys Leu Asn Phe Ile Ala Leu Thr Val Ala
1               5                   10                  15

Tyr Ala Leu Thr Pro Tyr Thr Glu Ala Ala Leu Val Arg Asp Asp Val
                20                  25                  30

Asp Tyr Gln Ile Phe Arg Asp Phe Ala Glu Asn Lys Gly Lys Phe Ser
            35                  40                  45

Val Gly Ala Thr Asn Val Glu Val Arg Asp Lys Lys Asn Gln Ser Leu
        50                  55                  60

Gly Ser Ala Leu Pro Asn Gly Ile Pro Met Ile Asp Phe Ser Val Val
65                  70                  75                  80

Asp Val Asp Lys Arg Ile Ala Thr Leu Val Asn Pro Gln Tyr Val Val
                85                  90                  95

Gly Val Lys His Val Ser Asn Gly Val Ser Glu Leu His Phe Gly Asn
            100                 105                 110

Leu Asn Gly Asn Met Asn Asn Gly Asn Ala Lys Ser His Arg Asp Val
            115                 120                 125

Ser Ser Glu Glu Asn Arg Tyr Tyr Thr Val Lys Asn Asn Phe Pro
130                 135                 140

Thr Glu Asn Val Thr Ser Phe Thr Lys Glu Glu Gln Asp Ala Gln Lys
145                 150                 155                 160

Arg Arg Glu Asp Tyr Tyr Met Pro Arg Leu Asp Lys Phe Val Thr Glu
                165                 170                 175

Val Ala Pro Ile Glu Ala Ser Thr Ala Asn Asn Asn Lys Gly Glu Tyr
            180                 185                 190

Asn Asn Ser Asp Lys Tyr Pro Ala Phe Val Arg Leu Gly Ser Gly Thr
        195                 200                 205

Gln Phe Ile Tyr Lys Lys Gly Ser Arg Tyr Gln Leu Ile Leu Thr Glu
    210                 215                 220

Lys Asp Lys Gln Gly Asn Leu Leu Arg Asn Trp Asp Val Gly Gly Asp
225                 230                 235                 240

Asn Leu Glu Leu Val Gly Asn Ala Tyr Thr Tyr Gly Ile Ala Gly Thr
                245                 250                 255

Pro Tyr Lys Val Asn His Glu Asn Asn Gly Leu Ile Gly Phe Gly Asn
            260                 265                 270

Ser Lys Glu Glu His Ser Asp Pro Lys Gly Ile Leu Ser Gln Asp Pro
        275                 280                 285

Leu Thr Asn Tyr Ala Val Leu Gly Asp Ser Gly Ser Pro Leu Phe Val
    290                 295                 300

Tyr Asp Arg Glu Lys Gly Lys Trp Leu Phe Leu Gly Ser Tyr Asp Phe
305                 310                 315                 320

Trp Ala Gly Tyr Asn Lys Lys Ser Trp Gln Glu Trp Asn Ile Tyr Lys
                325                 330                 335

His Glu Phe Ala Glu Lys Ile Tyr Gln Gln Tyr Ser Ala Gly Ser Leu
            340                 345                 350

Ile Gly Ser Asn Thr Gln Tyr Thr Trp Gln Ala Thr Gly Ser Thr Ser
        355                 360                 365

Thr Ile Thr Gly Gly Gly Glu Pro Leu Ser Val Asp Leu Thr Asp Gly
    370                 375                 380

Lys Asp Lys Pro Asn His Gly Lys Ser Ile Thr Leu Lys Gly Ser Gly
385                 390                 395                 400
```

-continued

```
Thr Leu Thr Leu Asn Asn His Ile Asp Gln Gly Ala Gly Gly Leu Phe
            405                 410                 415
Phe Glu Gly Asp Tyr Glu Val Lys Gly Thr Ser Asp Ser Thr Thr Trp
            420                 425                 430
Lys Gly Ala Gly Val Ser Val Ala Asp Gly Lys Thr Val Thr Trp Lys
            435                 440                 445
Val His Asn Pro Lys Tyr Asp Arg Leu Ala Lys Ile Gly Lys Gly Thr
            450                 455                 460
Leu Val Val Glu Gly Lys Gly Lys Asn Glu Gly Leu Leu Lys Val Gly
465                 470                 475                 480
Asp Gly Thr Val Ile Leu Lys Gln Lys Ala Asp Ala Asn Asn Lys Val
            485                 490                 495
Gln Ala Phe Ser Gln Val Gly Ile Val Ser Gly Arg Ser Thr Leu Val
            500                 505                 510
Leu Asn Asp Asp Lys Gln Val Asp Pro Asn Ser Ile Tyr Phe Gly Phe
            515                 520                 525
Arg Gly Gly Arg Leu Asp Leu Asn Gly Asn Ser Leu Thr Phe Asp His
            530                 535                 540
Ile Arg Asn Ile Asp Asp Gly Ala Arg Val Val Asn His Asn Met Thr
545                 550                 555                 560
Asn Thr Ser Asn Ile Thr Ile Thr Gly Glu Ser Leu Ile Thr Asn Pro
            565                 570                 575
Asn Thr Ile Thr Ser Tyr Asn Ile Glu Ala Gln Asp Asp His Pro
            580                 585                 590
Leu Arg Ile Arg Ser Ile Pro Tyr Arg Gln Leu Tyr Phe Asn Gln Asp
            595                 600                 605
Asn Arg Ser Tyr Tyr Thr Leu Lys Lys Gly Ala Ser Thr Arg Ser Glu
            610                 615                 620
Leu Pro Gln Asn Ser Gly Glu Ser Asn Glu Asn Trp Leu Tyr Met Gly
625                 630                 635                 640
Arg Thr Ser Asp Ala Ala Lys Arg Asn Val Met Asn His Ile Asn Asn
            645                 650                 655
Glu Arg Met Asn Gly Phe Asn Gly Tyr Phe Gly Glu Glu Thr Lys
            660                 665                 670
Ala Thr Gln Asn Gly Lys Leu Asn Val Thr Phe Asn Gly Lys Ser Asp
            675                 680                 685
Gln Asn Arg Phe Leu Leu Thr Gly Gly Thr Asn Leu Asn Gly Asp Leu
            690                 695                 700
Asn Val Glu Lys Gly Thr Leu Phe Leu Ser Gly Arg Pro Thr Pro His
705                 710                 715                 720
Ala Arg Asp Ile Ala Gly Ile Ser Ser Thr Lys Lys Asp Pro His Phe
            725                 730                 735
Thr Glu Asn Asn Glu Val Val Glu Asp Asp Trp Ile Asn Arg Asn
            740                 745                 750
Phe Lys Ala Thr Thr Met Asn Val Thr Gly Asn Ala Ser Leu Tyr Ser
            755                 760                 765
Gly Arg Asn Val Ala Asn Ile Thr Ser Asn Ile Thr Ala Ser Asn Asn
            770                 775                 780
Ala Gln Val His Ile Gly Tyr Lys Thr Gly Asp Thr Val Cys Val Arg
785                 790                 795                 800
Ser Asp Tyr Thr Gly Tyr Val Thr Cys His Asn Ser Asn Leu Ser Glu
            805                 810                 815
```

-continued

```
Lys Ala Leu Asn Ser Phe Asn Pro Thr Asn Leu Arg Gly Asn Val Asn
            820                 825                 830

Leu Thr Glu Asn Ala Ser Phe Thr Leu Gly Lys Ala Asn Leu Phe Gly
            835                 840                 845

Thr Ile Gln Ser Ile Gly Thr Ser Gln Val Asn Leu Lys Glu Asn Ser
850                 855                 860

His Trp His Leu Thr Gly Asn Ser Asn Val Asn Gln Leu Asn Leu Thr
865                 870                 875                 880

Asn Gly His Ile His Leu Asn Ala Gln Asn Asp Ala Asn Lys Val Thr
                885                 890                 895

Thr Tyr Asn Thr Leu Thr Val Asn Ser Leu Ser Gly Asn Gly Ser Phe
            900                 905                 910

Tyr Tyr Trp Val Asp Phe Thr Asn Lys Ser Asn Lys Val Val Val
            915                 920                 925

Asn Lys Ser Ala Thr Gly Asn Phe Thr Leu Gln Val Ala Asp Lys Thr
            930                 935                 940

Gly Glu Pro Asn His Asn Glu Leu Thr Leu Phe Asp Ala Ser Asn Ala
945                 950                 955                 960

Thr Arg Asn Asn Leu Glu Val Thr Leu Ala Asn Gly Ser Val Asp Arg
                965                 970                 975

Gly Ala Trp Lys Tyr Lys Leu Arg Asn Val Asn Gly Arg Tyr Asp Leu
            980                 985                 990

Tyr Asn Pro Glu Val Glu Lys Arg Asn Gln Thr Val Asp Thr Thr Asn
            995                 1000                1005

Ile Thr Thr Pro Asn Asp Ile Gln Ala Asp Ala Pro Ser Ala Gln Ser
            1010                1015                1020

Asn Asn Glu Glu Ile Ala Arg Val Glu Thr Pro Val Pro Pro Pro Ala
1025                1030                1035                1040

Pro Ala Thr Glu Ser Ala Ile Ala Ser Glu Gln Pro Glu Thr Arg Pro
                1045                1050                1055

Ala Glu Thr Ala Gln Pro Ala Met Glu Glu Thr Asn Thr Ala Asn Ser
                1060                1065                1070

Thr Glu Thr Ala Pro Lys Ser Asp Thr Ala Thr Gln Thr Glu Asn Pro
            1075                1080                1085

Asn Ser Glu Ser Val Pro Ser Glu Thr Thr Glu Lys Val Ala Glu Asn
            1090                1095                1100

Pro Pro Gln Glu Asn Glu Thr Val Ala Lys Asn Glu Gln Glu Ala Thr
1105                1110                1115                1120

Glu Pro Thr Pro Gln Asn Gly Glu Val Ala Lys Glu Asp Gln Pro Thr
                1125                1130                1135

Val Glu Ala Asn Thr Gln Thr Asn Glu Ala Thr Gln Ser Glu Gly Lys
            1140                1145                1150

Thr Glu Glu Thr Gln Thr Ala Glu Thr Lys Ser Glu Pro Thr Glu Ser
            1155                1160                1165

Val Thr Val Ser Glu Asn Gln Pro Glu Lys Thr Val Ser Gln Ser Thr
            1170                1175                1180

Glu Asp Lys Val Val Glu Lys Glu Lys Ala Lys Val Glu Thr
1185                1190                1195                1200

Glu Glu Thr Gln Lys Ala Pro Gln Val Thr Ser Lys Glu Pro Pro Lys
                1205                1210                1215

Gln Ala Glu Pro Ala Pro Glu Val Pro Thr Asp Thr Asn Ala Glu
            1220                1225                1230

Glu Ala Gln Ala Leu Gln Gln Thr Gln Pro Thr Thr Val Ala Ala Ala
```

-continued

```
              1235                1240                1245

Glu Thr Thr Ser Pro Asn Ser Lys Pro Ala Glu Thr Gln Gln Pro
    1250                1255                1260

Ser Glu Lys Thr Asn Ala Glu Pro Val Thr Pro Val Val Ser Glu Asn
1265                1270                1275                1280

Thr Ala Thr Gln Pro Thr Glu Thr Glu Thr Ala Lys Val Glu Lys
                1285                1290                1295

Glu Lys Thr Gln Glu Val Pro Gln Val Ala Ser Gln Glu Ser Pro Lys
                1300                1305                1310

Gln Glu Gln Pro Ala Ala Lys Pro Gln Ala Gln Thr Lys Pro Gln Ala
                1315                1320                1325

Glu Pro Ala Arg Glu Asn Val Leu Thr Thr Lys Asn Val Gly Glu Pro
    1330                1335                1340

Gln Pro Gln Ala Gln Pro Gln Thr Gln Ser Thr Ala Val Pro Thr Thr
1345                1350                1355                1360

Gly Glu Thr Ala Ala Asn Ser Lys Pro Ala Ala Lys Pro Gln Ala Gln
                1365                1370                1375

Ala Lys Pro Gln Thr Glu Pro Ala Arg Glu Asn Val Ser Thr Val Asn
    1380                1385                1390

Thr Lys Glu Pro Gln Ser Gln Thr Ser Ala Thr Val Ser Thr Glu Gln
                1395                1400                1405

Pro Ala Lys Glu Thr Ser Ser Asn Val Glu Gln Pro Ala Pro Glu Asn
    1410                1415                1420

Ser Ile Asn Thr Gly Ser Ala Thr Thr Met Thr Glu Thr Ala Glu Lys
1425                1430                1435                1440

Ser Asp Lys Pro Gln Met Glu Thr Val Thr Glu Asn Asp Arg Gln Pro
                1445                1450                1455

Glu Ala Asn Thr Val Ala Asp Asn Ser Val Ala Asn Asn Ser Glu Ser
                1460                1465                1470

Ser Glu Ser Lys Ser Arg Arg Arg Ser Val Ser Gln Pro Lys Glu
                1475                1480                1485

Thr Ser Ala Glu Glu Thr Thr Val Ala Ser Thr Gln Glu Thr Thr Val
    1490                1495                1500

Asp Asn Ser Val Ser Thr Pro Lys Pro Arg Ser Arg Arg Thr Arg Arg
1505                1510                1515                1520

Ser Val Gln Thr Asn Ser Tyr Glu Pro Val Glu Leu Pro Thr Glu Asn
                1525                1530                1535

Ala Glu Asn Ala Glu Asn Val Gln Ser Gly Asn Asn Val Ala Asn Ser
                1540                1545                1550

Gln Pro Ala Leu Arg Asn Leu Thr Ser Lys Asn Thr Asn Ala Val Ile
                1555                1560                1565

Ser Asn Ala Met Ala Lys Ala Gln Phe Val Ala Leu Asn Val Gly Lys
    1570                1575                1580

Ala Val Ser Gln His Ile Ser Gln Leu Glu Met Asn Asn Glu Gly Gln
1585                1590                1595                1600

Tyr Asn Val Trp Ile Ser Asn Thr Ser Met Asn Lys Asn Tyr Ser Ser
                1605                1610                1615

Glu Gln Tyr Arg Arg Phe Ser Ser Lys Ser Thr Gln Thr Gln Leu Gly
                1620                1625                1630

Trp Asp Gln Thr Ile Ser Asn Asn Val Gln Leu Gly Gly Val Phe Thr
                1635                1640                1645

Tyr Val Arg Asn Ser Asn Asn Phe Asp Lys Ala Ser Ser Lys Asn Thr
    1650                1655                1660
```

-continued

```
Leu Ala Gln Val Asn Phe Tyr Ser Lys Tyr Tyr Ala Asp Asn His Trp
1665                1670                1675                1680

Tyr Leu Gly Ile Asp Leu Gly Tyr Gly Lys Phe Gln Ser Asn Leu Gln
                1685                1690                1695

Thr Asn Asn Ala Lys Phe Ala Arg His Thr Ala Gln Ile Gly Leu
        1700                1705                1710

Thr Ala Gly Lys Ala Phe Asn Leu Gly Asn Phe Ala Val Lys Pro Thr
        1715                1720                1725

Val Gly Val Arg Tyr Ser Tyr Leu Ser Asn Ala Asp Phe Ala Leu Ala
        1730                1735                1740

Gln Asp Arg Ile Lys Val Asn Pro Ile Ser Val Lys Thr Ala Phe Ala
1745                1750                1755                1760

Gln Val Asp Leu Ser Tyr Thr Tyr His Leu Gly Glu Phe Ser Ile Thr
                1765                1770                1775

Pro Ile Leu Ser Ala Arg Tyr Asp Ala Asn Gln Gly Asn Gly Lys Ile
                1780                1785                1790

Asn Val Ser Val Tyr Asp Phe Ala Tyr Asn Val Glu Asn Gln Gln Gln
            1795                1800                1805

Tyr Asn Ala Gly Leu Lys Leu Lys Tyr His Asn Val Lys Leu Ser Leu
1810                1815                1820

Ile Gly Gly Leu Thr Lys Ala Lys Gln Ala Glu Lys Gln Lys Thr Ala
1825                1830                1835                1840

Glu Val Lys Leu Ser Phe Ser Phe
                1845
```

(2) INFORMATION FOR SEQ ID NO:7:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO:7:

```
Gly Asp Ser Gly Ser Pro Met Phe
1               5
```

(2) INFORMATION FOR SEQ ID NO:8:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO:8:

```
Gly Asp Ser Gly Ser Pro Leu Phe
1               5
```

(2) INFORMATION FOR SEQ ID NO:9:

(i) SEQUENCE CHARACTERISTICS:
        (A) LENGTH: 7 amino acids
        (B) TYPE: amino acid
        (D) TOPOLOGY: linear (xi) SEQUENCE DESCRIPTION: SEQ ID NO:9:

```
His Thr Tyr Phe Gly Ile Asp
1               5
```

HAEMOPHILUS ADHERENCE AND PENETRATION PROTEINS

This invention was made with government support under grant numbers HD 29678 and AI 23945 awarded by the National Institute of Health. The government has certain rights in the invention.

FIELD OF THE INVENTION

The invention relates to Haemophilus adhesion and penetration proteins, nucleic acids, and vaccines.

BACKGROUND OF THE INVENTION

Most bacterial diseases begin with colonization of a particular mucosal surface (Beachey et al., 1981, J. Infect. Dis. 143:325–345). Successful colonization requires that an organism overcome mechanical cleansing of the mucosal surface and evade the local immune response. The process of colonization is dependent upon specialized microbial factors that promote binding to host cells (Hultgren et al., 1993 Cell, 73:887–901). In some cases the colonizing organism will subsequently enter (invade) these cells and survive intracellularly (Falkow, 1991, Cell 65:1099–1102).

*Haemophilus influenzae* is a common commensal organism of the human respiratory tract (Kuklinska and Kilian, 1984, Eur. J. Clin. Microbiol. 3:249–252). It is a human-specific organism that normally resides in the human nasopharynx and must colonize this site in order to avoid extinction. This microbe has a number of surface structures capable of promoting attachment to host cells (Guerina et al., 1982, J. Infect. Dis. 146:564; Pichichero et al., 1982, Lancet ii:960–962; St. Geme et al., 1993, Proc. Natl. Acad. Sci. U.S.A. 90:2875–2879). In addition, *H. influenzae* has acquired the capacity to enter and survive within these cells (Forsgren et al., 1994, Infect. Immun. 62:673–679; St. Geme and Falkow, 1990, Infect. Immun. 58:4036–4044; St. Geme and Falkow, 1991, Infect. Immun. 59:1325–1333, Infect. Immun. 59:3366–3371). As a result, this bacterium is an important cause of both localized respiratory tract and systemic disease (Turk, 1984, J. Med. Microbiol. 18:1–16). Nonencapsulated, non-typable strains account for the majority of local disease (Turk, 1984, supra); in contrast, serotype b strains, which express a capsule composed of a polymer of ribose and ribitol-5-phosphate (PRP), are responsible for over 95% of cases of *H. influenzae* systemic disease (Turk, 1982, Clinical importance of *Haemophilus influenzae*, p. 3–9. In S.H. Sell and P. F. Wright (ed.), *Haemophilus influenzae* epidemiology, immunology, and prevention of disease. Elsevier/North-Holland Publishing Co., New York).

The initial step in the pathogenesis of disease due to *H. influenzae* involves colonization of the upper respiratory mucosa (Murphy et al., 1987, J. Infect. Dis. 5:723–731). Colonization with a particular strain may persist for weeks to months, and most individuals remain asymptomatic throughout this period (Spinola et al., 1986, I. Infect. Dis. 154:100–109). However, in certain circumstances colonization will be followed by contiguous spread within the respiratory tract, resulting in local disease in the middle ear, the sinuses, the conjunctiva, or the lungs. Alternatively, on occasion bacteria will penetrate the nasopharyngeal epithelial barrier and enter the bloodstream.

In vitro observations and animal studies suggest that bacterial surface appendages called pili (or fimbriae) play an important role in *H. influenzae* colonization. In 1982 two groups reported a correlation between piliation and increased attachment to human oropharyngeal epithelial cells and erythrocytes (Guerina et al., supra; Pichichero et al., supra). Other investigators have demonstrated that antipilus antibodies block in vitro attachment by piliated *H. influenzae* (Forney et al., 1992, J. Infect. Dis. 165:464–470; van Alphen et al., 1988, Infect. Immun. 56:1800–1806). Recently Weber et al. insertionally inactivated the pilus structural gene in an *H. influenzae* type b strain and thereby eliminated expression of pili; the resulting mutant exhibited a reduced capacity for colonization of year-old monkeys (Weber et al., 1991, Infect. Immun. 59:4724–4728).

A number of reports suggest that nonpilus factors also facilitate Haemophilus colonization. Using the human nasopharyngeal organ culture model, Farley et al. (1986, J. Infect. Dis. 161:274–280) and Loeb et al. (1988, Infect. Immun. 49:484–489) noted that nonpiliated type b strains were capable of mucosal attachment. Read and coworkers made similar observations upon examining nontypable strains in a model that employs nasal turbinate tissue in organ culture (1991, J. Infect. Dis. 163:549–558). In the monkey colonization study by Weber et al. (1991, supra), nonpiliated organisms retained a capacity for colonization, though at reduced densities; moreover, among monkeys originally infected with the piliated strain, virtually all organisms recovered from the nasopharynx were nonpiliated. All of these observations are consistent with the finding that nasopharyngeal isolates from children colonized with *H. influenzae* are frequently nonpiliated (Mason et al., 1985, Infect. Immun. 49:98–103; Brinton et al., 1989, Pediatr. Infect. Dis. J. 8:554–561).

Previous studies have shown that *H. influenzae* are capable of entering (invading) cultured human epithelial cells via a pili-independent mechanism (St. Geme and Falkow, 1990, supra; St. Geme and Falkow, 1991, supra). Although *H. influenzae* is not generally considered an intracellular parasite, a recent report suggests that these in vitro findings may have an in vivo correlate (Forsgren et al., 1994, supra). Forsgren and coworkers examined adenoids from 10 children who had their adenoids removed because of long-standing secretory otitis media or adenoidal hypertrophy. In all 10 cases there were viable intracellular *H. influenzae*. Electron microscopy demonstrated that these organisms were concentrated in the reticular crypt epithelium and in macrophage-like cells in the subepithelial layer of tissue. One possibility is that bacterial entry into host cells provides a mechanism for evasion of the local immune response, thereby allowing persistence in the respiratory tract.

Thus, a vaccine for the therapeutic and prophylactic treatment of Haemophilus infection is desirable. Accordingly, it is an object of the present invention to provide for recombinant Haemophilus Adherence and Penetration (HAP) proteins and variants thereof, and to produce useful quantities of these HAP proteins using recombinant DNA techniques.

It is a further object of the invention to provide recombinant nucleic acids encoding HAP proteins, and expression vectors and host cells containing the nucleic acid encoding the HAP protein.

An additional object of the invention is to provide monoclonal antibodies for the diagnosis of Haemophilus infection.

A further object of the invention is to provide methods for producing the HAP proteins, and a vaccine comprising the HAP proteins of the present invention. Methods for the therapeutic and prophylactic treatment of Haemophilus infection are also provided.

SUMMARY OF THE INVENTION

In accordance with the foregoing objects, the present invention provides recombinant HAP proteins, and isolated or recombinant nucleic acids which encode the HAP proteins of the present invention. Also provided are expression vectors which comprise DNA encoding a HAP protein operably linked to transcriptional and translational regulatory DNA, and host cells which contain the expression vectors.

The invention provides also provides methods for producing HAP proteins which comprises culturing a host cell transformed with an expression vector and causing expression of the nucleic acid encoding the HAP protein to produce a recombinant HAP protein.

The invention also includes vaccines for *Haemophilus influenzae* infection comprising an HAP protein for prophylactic or therapeutic use in generating an immune response in a patient. Methods of treating or preventing Haemophilus influenzae infection comprise administering a vaccine.

BRIEF DESCRIPTION OF THE DRAWINGS

FIGS. 1A and 1B depict light micrographs of *H. influenzae* strains DB117(pGJB103) and DB117(pN187) incubated with Chang epithelial cells. Bacteria were incubated with an epithelial monolayer for 30 minutes before rinsing and straining with Giemsa stain. FIG. 1A: *H. influenzae* strain DB117 carrying cloning vector alone (pGJB103); FIG. 1B: *H. influenzae* strain DB117 harboring recombinant plasmid pH187. Bar represents 3.5 μm.

FIGS. 2A, 2B, 2C and 2D depict thin section transmission electron micrographs demonstrating interaction between *H. influenzae* strains N187 and DB117 (pN187) with Chang epithelial cells. Bacteria were incubated with epithelial monolayers for four hours before rinsing and processing for examination by transmission electron microscopy. FIG. 2A: strain N187 associated with the epithelial cell surface and present in an intracellular location; FIG. 2B: *H. influenzae* DB117 (pH187) in intimate contact with the epithelial cell surface; FIG. 2C: strain DB117(pN187) in the process of entering an epithelial cell; FIG. 2D: strain DB117(pN187) present in an intracellular location. Bar represents 1 μm.

FIG. 3 depicts outer membrane protein profiles of various strains. Outer membrane proteins were isolated on the basis of sarcosyl insolubility and resolved on a 10% SDS-polyacrylamide gel. Proteins were visualized by staining with Coomassie blue. Lane 1, *H. influenzae* strain DB117 (pGJB103); lane 2, strain DB117 (pN187); lane 3, strain DB117(pJS106); lane 4, *E. coli* HB101(pGJB103); lane 5, HB101(pN187). Note novel proteins at ~160 kD and 45 kD marked by asterisks in lanes 2 and 3.

FIG. 4 depicts a restriction map of pN187 and derivatives and locations of mini-Tn10 kan insertions. pN187 is a derivative of pGJB103 that contains an 8.5-kb Sau3AI fragment of chromosomal DNA from *H. influenzae* strain N187. Vector sequences are represented by hatched boxes. Letters above top horizontal line indicate restriction enzyme sites: Bg, BglII; C, ClaI; E, EcoRI; P, PstI. Numbers and lollipops above top horizontal line show positions of mini-Tn10 kan insertions; open lollipops represent insertions that have no effect on adherence and invasion, while closed lollipops indicate insertions that eliminate the capacity of pN187 to promote association with epithelial monolayers. Heavy horizontal line with arrow represents location of hap locus within pN187 and direction of transcription. (+): recombinant plasmids that promote adherence and invasion; (−): recombinant plasmids that fail to promote adherence and invasion.

FIG. 5 depicts the identification of plasmid-encoded proteins using the bacteriophage T7 expression system. Bacteria were radiolabeled with [$^{35}$S] methionine, and whole cell lysates were resolved on a 10% SDS-polyacrylamide gel. Proteins were visualized by autoradiography. Lane 1, *E. coli* XL-1 Blue(pT7-7) uninduced; lane 2, XL-1 Blue(pT7-7) induced with IPTG; lane 3, XL-1 Blue(pJS103) uninduced; lane 4, XL-1 Blue(pJS103) induced with IPTG; lane 5, XL-1 Blue(pJS104) uninduced; lane 6, XL-1 Blue(pJS104) induced with IPTG. The plasmids pJS103 and pJS104 are derivatives of pT7-7 that contain the 6.5-kb PstI fragment from pN187 in opposite orientations. Asterisk indicates overexpressed protein in XL-1 Blue(pJS104).

FIGS. 6A, 6B, and 6C depict the nucleotide sequence (SEQ ID NO:1) and predicted amino acid sequence (SEQ ID NO:2) of hap gene. Putative −10 and −35 sequences 5' to the hap coding sequence are underlined; a putative rho-independent terminator 3' to the hap stop codon is indicated with inverted arrows. The first 25 amino acids of the protein, which are boxed, represent the signal sequence.

FIGS. 7A, 7B, 7C, 7D, 7E, 7F, 7G, and 7H depict a sequence comparison of the hap product and the cloned *H. influenzae* IgA1 proteases. Amino acid homologies between the deduced hap gene product and the iga gene products from *H. influenzae* HK368, (SEQ ID NO:3) HK61, (SEQ ID NO:6) HK393, (SEQ ID NO:4) and HK793 (SEQ ID NO:5) are shown. Dashes indicate gaps introduced in the sequences in order to obtain maximal homology. A consensus sequence for the five proteins is shown on the lower line. The conserved serine-type protease catalytic domain is underlined, and the common active site serine is denoted by an asterisk. The conserved cysteines are also indicated by asterisks.

FIG. 8 depicts the IgA1 protease activity assay. Culture supernatants were assayed for the ability to cleave IgA1. Reaction mixtures were resolved on a 10% SDS-polyacrylamide gel and then transferred to a nitrocellulose membrane. The membrane was probed with antibody against human IgA1 heavy chain. Lane 1, *H. influenzae* strain N187; lane 2, strain DB117(pGJB103); lane 3, strain DB117 (pN187). The cleavage product patterns suggest that strain N187 contains a type 2 IgA1 protease while strains DB117 (pGJB103) and DB117(pN187) contain a type 1 enzyme. The upper band of ~70-kD seen with the DB117 derivatives represents intact IgA1 heavy chain.

FIGS. 9A and 9B depict southern analysis of chromosomal DNA from strain *H. influenzae* N187, probing with hap versus iga. DNA fragments were separated on a 0.7% agarose gel and transferred bidirectionally to nitrocellulose membranes prior to probing with either hap or iga. Lane 1, N187 chromosomal DNA digested with EcoRI; lane 2, N187 chromosomal DNA digested with BglII; lane 3, N187 chromosomal DNA digested with BamHI; lane 4, the 4.8-kb ClaI-PstI fragment from pN187 that contains the intact hap gene. FIG. 9A: Hybridization with the 4.8-kb ClaI-PstI fragment containing the hap gene; FIG. 9B: hybridization with the iga gene from *H. influenzae* strain Rd, carried as a 4.8-kb ClaI-EcoRI fragment in pVD116.

FIG. 10 depicts a SDS-polyacrylamide gel of secreted proteins. Bacteria were grown to late log phase, and culture supernatants were precipitated with trichloroacetic acid and then resolved on a 10% SDS-polyacrylamide gel. Proteins were visualized by staining with Coomassie blue. Lane 1, *H. influenzae* strain DB117(pGJB103); lane 2, DB117(pN187); lane 3, DB 117(pJS106); lane 4, DB117(pJS102); lane 5, DB117(pJS105); lane 6, DB117(Tn10-18); lane 7, DB117 (Tn10-4'); lane 8, DB117(Tn10-30); lane 9, DB117(Tn10-16); lane 10, DB117(Tn10-10); lane 11, DB117(Tn10-8);

lane 12, N187. Asterisk indicates 110-kD secreted protein encoded by hap.

DETAILED DESCRIPTION OF THE INVENTION

The present invention provides novel Haemophilus Adhesion and Penetration (HAP) proteins. In a preferred embodiment, the HAP proteins are from Haemophilus strains, and in the preferred embodiment, from *Haemophilus influenza*. However, using the techniques outlined below, HAP proteins from other *Haemophilus influenzae* strains, or from other bacterial species such as Neisseria spp. or Bordetalla spp. may also be obtained.

A HAP protein may be identified in several ways. A HAP nucleic acid or HAP protein is initially identified by substantial nucleic acid and/or amino acid sequence homology to the sequences shown in FIG. 6. Such homology can be based upon the overall nucleic acid or amino acid sequence.

The HAP proteins of the present invention have limited homology to *Haemophilus influenzae* and *N. gonorrhoeae* serine-type IgA1 proteases. This homology, shown in FIG. 7, is approximately 30–35% at the amino acid level, with several stretches showing 55–60% identity., including amino acids 457–549, 399–466, 572–622, and 233–261. However, the homology between the HAP protein and the IgA1 protease is considerably lower than the similarity among the IgA1 proteases themselves.

In addition, the full length HAP protein has homology to Tsh, a hemagglutinin expressed by an avian *E. coli* strain (Provence and Curtiss 1994, Infect. Immun. 62:1369–1380). The homology is greatest in the N-terminal half of the proteins, and the overall homology is 30.5% homologous. The full length HAP protein also has homology with pertactin, a 69 kD outer membrane protein expressed by *B. pertussis*, with the middle portion of the proteins showing 39% homology. Finally, HAP has 34–52% homology with six regions of HpmA, a calcium-independent hemolysin expressed by *Proteus mirabilis* (Uphoff and Welch, 1990, J. Bacteriol. 172:1206–1216).

As used herein, a protein is a "HAP protein" if the overall homology of the protein sequence to the amino acid sequence shown in FIG. 6 (SEQ ID NO:2) is preferably greater than about 40–50%, more preferably greater than about 60% and most preferably greater than 80%. In some embodiments the homology will be as high as about 90 to 95 or 98%. This homology will be determined using standard techniques known in the art, such as the Best Fit sequence program described by Devereux et al., *Nucl. Acid Res.* 12:387–395 (1984). The alignment may include the introduction of gaps in the sequences to be aligned. In addition, for sequences which contain either more or fewer amino acids than the protein shown in FIG. 6, it is understood that the percentage of homology will be determined based on the number of homologous amino acids in relation to the total number of amino acids. Thus, for example, homology of sequences shorter than that shown in FIG. 6, as discussed below, will be determined using the number of amino acids in the shorter sequence.

HAP proteins of the present invention may be shorter than the amino acid sequence shown in FIG. 6. As shown in the Examples, the HAP protein may undergo post-translational processing similar to that seen for the serine-type IgA1 proteases expressed by *Haemophilus influenzae* and *N. gonorrhoeae*. These proteases are synthesized as preproteins with three functional domains: the N-terminal signal peptide, the protease, and a C-terminal helper domain. Following movement of these proteins into the periplasmic space, the carboxy terminal β-domain of the proenzyme is inserted into the outer membrane, possibly forming a pore (Poulsen et al., 1989, Infect. Immun. 57:3097–3105; Pohlner et al., 1987, Nature (London). 325:458–462; Klauser et al., 1992, EMBO J. 11:2327–2335; Klauser et al., 1993, J. Mol. Biol. 234:579–593). Subsequently the amino end of the protein is exported through the outer membrane, and autoproteolytic cleavage occurs to result in secretion of the mature 100 to 106-kD protease. The 45 to 56-kD C-terminal β-domain remains associated with the outer membrane following the cleavage event. As shown in the Examples, the HAP nucleic acid is associated with expression of a 160 kD outer membrane protein. The secreted gene product is an approximately 110 kD protein, with the simultaneous appearance of a 45 kD outer membrane protein. The 45 kD protein appears to correspond to amino acids from about 960 to about 1394 of FIG. 6. Any one of these proteins is considered a HAP protein for the purposes of this invention.

Thus, in a preferred embodiment, included within the defintion of HAP proteins are portions or fragments of the sequence shown in FIG. 6. The fragments may be fragments of the entire sequence, the 110 kD sequence, or the 45 kD sequence. Generally, the HAP protein fragments may range in size from about 10 amino acids to about 1900 amino acids, with from about 50 to about 1000 amino acids being preferred, and from about 100 to about 500 amino acids also preferred. Particularly preferred fragments are sequences unique to HAP; these sequences have particular use in cloning HAP proteins from other organisms or to generate antibodies specific to HAP proteins. Unique sequences are easily identified by those skilled in the art after examination of the HAP protein sequence and comparison to other proteins; for example, by examination of the sequence alignment shown in FIG. 7. For instance, as compared to the IgA proteases, unique sequences include, but are not limited to, amino acids 11–14, 16–22, 108–120, 155–164, 257–265, 281–288, 318–336, 345–353, 398–416, 684–693, 712–718, 753–761, 871–913, 935–953, 985–1008, 1023–1034, 1067–1076, 1440–1048, 1585–1592, 1631–1639, 1637–1648, 1735–1743, 1863–1871, 1882–1891, 1929–1941, and 1958–1966 (using the numbering of FIG. 7). HAP protein fragments which are included within the definition of a HAP protein include N- or C-terminal truncations and deletions which still allow the protein to be biologically active; for example, which still exhibit proteolytic activity in the case of the 110 kD putative protease sequence. In addition, when the HAP protein is to be used to generate antibodies, for example as a vaccine, the HAP protein must share at least one epitope or determinant with either the full length protein, the 110 kD protein or the 45 kD protein, shown in FIG. 6. In a preferred embodiment, the epitope is unique to the HAP protein; that is, antibodies generated to a unique epitope exhibit little or no cross-reactivity with other proteins. By "epitope" or "determinant" herein is meant a portion of a protein which will generate and/or bind an antibody. Thus, in most instances, antibodies made to a smaller HAP protein will be able to bind to the full length protein.

In some embodiments, the fragment of the HAP protein used to generate antibodies are small; thus, they may be used as haptens and coupled to protein carriers to generate antibodies, as is known in the art.

Preferably, the antibodies are generated to a portion of the HAP protein which remains attached to the *Haemophilus influenzae* organism. For example, the HAP protein can be used to vaccinate a patient to produce antibodies which upon exposure to the *Haemophilus influenzae* organism (e.g. during a subsequent infection) bind to the organism and allow an immune response. Thus, in one embodiment, the antibodies are generated to the roughly 45 kD fragment of the full length HAP protein. Preferably, the antibodies are generated to the portion of the 45 kD fragment which is exposed at the outer membrane.

In an alternative embodiment, the antibodies bind to the mature secreted 110 kD fragment. For example, as explained in detail below, the HAP proteins of the present invention may be administered therapeutically to generate neutralizing antibodies to the 110 kD putative protease, to decrease the undesirable effects of the 100 kD fragment.

In the case of the nucleic acid, the overall homology of the nucleic acid sequence is commensurate with amino acid homology but takes into account the degeneracy in the genetic code and codon bias of different organisms. Accordingly, the nucleic acid sequence homology may be either lower or higher than that of the protein sequence. Thus the homology of the nucleic acid sequence as compared to the nucleic acid sequence of FIG. 6 is preferably greater than 40%, more preferably greater than about 60% and most preferably greater than 80%. In some embodiments the homology will be as high as about 90 to 95 or 98%.

In one embodiment, the nucleic acid homology is determined through hybridization studies. Thus, for example, nucleic acids which hybridize under high stringency to all or part of the nucleic acid sequence shown in FIG. 6 are considered HAP protein genes. High stringency conditions include washes with 0.1XSSC at 65° C. for 2 hours.

The HAP proteins and nucleic acids of the present invention are preferably recombinant. As used herein, "nucleic acid" may refer to either DNA or RNA, or molecules which contain both deoxy- and ribonucleotides. The nucleic acids include genomic DNA, cDNA and oligonucleotides including sense and anti-sense nucleic acids. Specifically included within the definition of nucleic acid are anti-sense nucleic acids. An anti-sense nucleic acid will hybridize to the corresponding non-coding strand of the nucleic acid sequence shown in FIG. 6, but may contain ribonucleotides as well as deoxyribonucleotides. Generally, anti-sense nucleic acids function to prevent expression of mRNA, such that a HAP protein is not made, or made at reduced levels. The nucleic acid may be double stranded, single stranded, or contain portions of both double stranded or single stranded sequence. By the term "recombinant nucleic acid" herein is meant nucleic acid, originally formed in vitro by the manipulation of nucleic acid by endonucleases, in a form not normally found in nature. Thus an isolated HAP protein gene, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Similarly, a "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated away from some or all of the proteins and compounds with which it is normally associated in its wild type host, or found in the absence of the host cells themselves. Thus, the protein may be partially or substantially purified. The definition includes the production of a HAP protein from one organism in a different organism or host cell. Alternatively, the protein may be made at a significantly higher concentration than is normally seen, through the use of a inducible promoter or high expression promoter, such that the protein is made at increased concentration levels. Alternatively, the protein may be in a form not normally found in nature, as in the addition of an epitope tag or amino acid substitutions, insertions and deletions.

Also included with the definition of HAP protein are HAP proteins from other organisms, which are cloned and expressed as outlined below.

In the case of anti-sense nucleic acids, an anti-sense nucleic acid is defined as one which will hybridize to all or part of the corresponding non-coding sequence of the sequence shown in FIG. 6. Generally, the hybridization conditions used for the determination of anti-sense hybridization will be high stringency conditions, such as 0.1XSSC at 65° C.

Once the HAP protein nucleic acid is identified, it can be cloned and, if necessary, its constituent parts recombined to form the entire HAP protein nucleic acid. Once isolated from its natural source, e.g., contained within a plasmid or other vector or excised therefrom as a linear nucleic acid segment, the recombinant HAP protein nucleic acid can be further used as a probe to identify and isolate other HAP protein nucleic acids. It can also be used as a "precursor" nucleic acid to make modified or variant HAP protein nucleic acids and proteins.

Using the nucleic acids of the present invention which encode HAP protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the HAP protein. "Operably linked" in this context means that the transcriptional and translational regulatory DNA is positioned relative to the coding sequence of the HAP protein in such a manner that transcription is initiated. Generally, this will mean that the promoter and transcriptional initiation or start sequences are positioned 5' to the HAP protein coding region. The transcriptional and translational regulatory nucleic acid will generally be appropriate to the host cell used to express the HAP protein; for example, transcriptional and translational regulatory nucleic acid sequences from Bacillus will be used to express the HAP protein in Bacillus. Numerous types of appropriate expression vectors, and suitable regulatory sequences are known in the art for a variety of host cells.

In general, the transcriptional and translational regulatory sequences may include, but are not limited to, promoter sequences, leader or signal sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, the expression vector may comprise additional elements. For example, the expression vector may have two replication systems, thus allowing it to be maintained in two organisms, for example in mammalian or insect cells for expression and in a procaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

The HAP proteins of the present invention are produced by culturing a host cell transformed with an expression vector containing nucleic acid encoding a HAP protein, under the appropriate conditions to induce or cause expression of the HAP protein. The conditions appropriate for HAP protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archebacteria, fungi, and insect and animal cells, including mammalian cells. of particular interest are *Drosophila melangaster* cells, *Saccharomyces cerevisiae* and other yeasts, *E. coli, Bacillus subtilis,* SF9 cells, C129 cells, 293 cells, Neurospora, BHK, CHO, COS, and HeLa cells, immortalized mammalian myeloid and lymphoid cell lines.

In a preferred embodiment, HAP proteins are expressed in bacterial systems. Bacterial expression systems are well known in the art.

A suitable bacterial promoter is any nucleic acid sequence capable of binding bacterial RNA polymerase and initiating the downstream (3') transcription of the coding sequence of HAP protein into inRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In *E. coli,* the ribosome binding site is called the Shine-Delgarno (SD) sequence and includes an initiation codon and a sequence 3–9 nucleotides in length located 3–11 nucleotides upstream of the initiation codon.

The expression vector may also include a signal peptide sequence that provides for secretion of the HAP protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria).

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis, E. coli, Streptococcus cremoris,* and *Streptococcus lividans,* among others.

The bacterial expression vectors are transformed into bacterial host cells using techniques well known in the art, such as calcium chloride treatment, electroporation, and others.

In one embodiment, HAP proteins are produced in insect cells. Expression vectors for the transformation of insect cells, and in particular, baculovirus-based expression vectors, are well known in the art. Briefly, baculovirus is a very large DNA virus which produces its coat protein at very high levels. Due to the size of the baculoviral genome, exogenous genes must be placed in the viral genome by recombination. Accordingly, the components of the expression system include: a transfer vector, usually a bacterial plasmid, which contains both a fragment of the baculovirus genome, and a convenient restriction site for insertion of the HAP protein; a wild type baculovirus with a sequence homologous to the baculovirus-specific fragment in the transfer vector (this allows for the homologous recombination of the heterologous gene into the baculovirus genome); and appropriate insect host cells and growth media.

Mammalian expression systems are also known in the art and are used in one embodiment. A mammalian promoter is any DNA sequence capable of binding mammalian RNA polymerase and initiating the downstream (3') transcription of a coding sequence for HAP protein into mRNA. A promoter will have a transcription initiating region, which is usually place proximal to the 5' end of the coding sequence, and a TATA box, using a located 25–30 base pairs upstream of the transcription initiation site. The TATA box is thought to direct RNA polymerase II to begin RNA synthesis at the correct site. A mammalian promoter will also contain an upstream promoter element, typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, and herpes simplex virus promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenlytion signals include those derived form SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, encapsulation of the polynucleotide (s) in liposomes, and direct microinjection of the DNA into nuclei.

In a preferred embodiment, HAP protein is produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomvces pombe,* and *Yarrowia lipolytica*. Preferred promoter sequences for expression in yeast include the inducible GAL1, 10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP1, and ALG7, which confers resistance to tunicamycin; the G418 resistance gene, which confers resistance to G418; and the CUP1 gene, which allows yeast to grow in the presence of copper ions.

A recombinant HAP protein may be expressed intracellularly or secreted. The HAP protein may also be made as a fusion protein, using techniques well known in the art. Thus, for example, if the desired epitope is small, the HAP protein may be fused to a carrier protein to form an immunogen. Alternatively, the HAP protein may be made as a fusion protein to increase expression.

Also included within the definition of HAP proteins of the present invention are amino acid sequence variants. These variants fall into one or more of three classes: substitutional, insertional or deletional variants. These variants ordinarily are prepared by site specific mutagenesis of nucleotides in the DNA encoding the HAP protein, using cassette mutagenesis or other techniques well known in the art, to produce DNA encoding the variant, and thereafter expressing the DNA in recombinant cell culture as outlined above. However, variant HAP protein fragments having up to about 100–150 residues may be prepared by in vitro synthesis using established techniques. Amino acid sequence variants are characterized by the predetermined nature of the variation, a feature that sets them apart from naturally occurring allelic or interspecies variation of the HAP protein amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed HAP protein variants screened for the optimal combination of desired activity. Techniques for making substitution mutations at predetermined sites in DNA having a known sequence are well known, for example, M13 primer mutagenesis. Screening of the mutants is done using assays of HAP protein activities; for example, mutated HAP genes are placed in HAP deletion strains and tested for HAP activity, as disclosed herein. The creation of deletion strains, given a gene sequence, is known in the art. For example, nucleic acid encoding the variants may be expressed in a *Haemophilus influenzae* strain deficient in the HAP protein, and the adhesion and infectivity of the variant *Haemophilus influenzae* evaluated. Alternatively, the variant HAP protein may be expressed and its biological characteristics evaluated, for example its proteolytic activity.

Amino acid substitutions are typically of single residues; insertions usually will be on the order of from about 1 to 20 amino acids, although considerably larger insertions may be tolerated. Deletions range from about 1 to 30 residues, although in some cases deletions may be much larger, as for example when one of the domains of the HAP protein is deleted.

Substitutions, deletions, insertions or any combination thereof may be used to arrive at a final derivative. Generally these changes are done on a few amino acids to minimize the alteration of the molecule. However, larger changes may be tolerated in certain circumstances.

When small alterations in the characteristics of the HAP protein are desired, substitutions are generally made in accordance with the following chart:

CHART I

| Original Residue | Exemplary Substitutions |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity and will elicit the same immune response as the naturally-occurring analogue, although variants also are selected to modify the characteristics of the polypeptide as needed. Alternatively, the variant may be designed such that the biological activity of the HAP protein is altered. For example, the proteolytic activity of the larger 110 kD domain of the HAP protein may be altered, through the substitution of the amino acids of the active site. The putative catalytic domain of this protein is GDSGSPMF, (SEQ ID NO:7) with the first serine corresponding to the active site serine characteristic of serine type proteases. The residues of the active site may be individually or simultaneously altered to decrease or eliminate proteolytic activity. This may be done to decrease the toxicity or side effects of the vaccine. Similarly, the cleavage site between the 45 kD domain and the 100 kD domain may be altered, for example to eliminate proteolytic processing to form the two domains. Putatively this site is at residue 960.

In a preferred embodiment, the HAP protein is purified or isolated after expression. HAP proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the HAP protein may be purified using a standard anti-HAP antibody column. Ultrafiltration and diafiltration techniques, in conjunction with protein concentration, are also useful. For general guidance in suitable purification techniques, see Scopes, R., Protein Purification, Springer-Verlag, NY (1982). The degree of purification necessary will vary depending on the use of the HAP protein. In some instances no purification will be necessary.

Once expressed and purified if necessary, the HAP proteins are useful in a number of applications.

For example, the HAP protein can be coupled, using standard technology, to affinity chromatography columns. These columns may then be used to purify antibodies from samples obtained from animals or patients exposed to the *Haemophilus influenzae* organism. The purified antibodies may then be used as outlined below.

Additionally, the HAP proteins are useful to make antibodies to HAP proteins. These antibodies find use in a number of applications. In a preferred embodiment, the antibodies are used to diagnose the presence of an *Haemophilus influenzae* infection in a sample or patient. This will be done using techniques well known in the art; for example, samples such as blood or tissue samples may be obtained from a patient and tested for reactivity with the antibodies, for example using standard techniques such as ELISA. In a preferred embodiment, monoclonal antibodies are generated to the HAP protein, using techniques well known in the art. As outlined above, the antibodies may be generated to the full length HAP protein, or a portion of the HAP protein.

Antibodies generated to HAP proteins may also be used in passive immunization treatments, as is known in the art.

Antibodies generated to unique sequences of HAP proteins may also be used to screen expression libraries from other organisms to find, and subsequently clone, HAP nucleic acids from other organisms.

In one embodiment, the antibodies may be directly or indirectly labelled. By "labelled" herein is meant a compound that has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the compound at any position. Thus, for example, the HAP protein antibody may be labelled for detection, or a secondary antibody to the HAP protein antibody may be created and labelled.

In one embodiment, the antibodies generated to the HAP proteins of the present invention are used to purify or separate HAP proteins or the *Haemophilus influenzae* organism from a sample. Thus for example, antibodies generated to HAP proteins which will bind to the *Haemophilus influenzae* organism may be coupled, using standard technology, to affinity chromatography columns. These columns can be used to pull out the Haemophilus organism from environmental or tissue samples. Alternatively, antibodies generated to the soluble 110 kD portion of the full-length portion of the protein shown in FIG. 7 may be used to purify the 110 kD protein from samples.

In a preferred embodiment, the HAP proteins of the present invention are used as vaccines for the prophylactic or therapeutic treatment of a *Haemophilus influenzae* infection in a patient. By "vaccine" herein is meant an antigen or compound which elicits an immune response in an animal or patient. The vaccine may be administered prophylactically, for example to a patient never previously exposed to the antigen, such that subsequent infection by the *Haemophilus influenzae* organism is prevented. Alternatively, the vaccine may be administered therapeutically to a patient previously exposed or infected by the *Haemophilus influenzae* organism. While infection cannot be prevented, in this case an immune response is generated which allows the patient's immune system to more effectively combat the infection. Thus, for example, there may be a decrease or lessening of the symptoms associated with infection. A "patient" for the purposes of the present invention includes both humans and other animals and organisms. Thus the methods are applicable to both human therapy and veterinary applications.

The administration of the HAP protein as a vaccine is done in a variety of ways. Generally, the HAP proteins can be formulated according to known methods to prepare pharmaceutically useful compositions, whereby therapeutically effective amounts of the HAP protein are combined in admixture with a pharmaceutically acceptable carrier vehicle. Suitable vehicles and their formulation are well known in the art. Such compositions will contain an effective amount of the HAP protein together with a suitable amount of vehicle in order to prepare pharmaceutically acceptable compositions for effective administration to the host. The composition may include salts, buffers, carrier proteins such as serum albumin, targeting molecules to localize the HAP protein at the appropriate site or tissue within the organism, and other molecules. The composition may include adjuvants as well.

In one embodiment, the vaccine is administered as a single dose; that is, one dose is adequate to induce a sufficient immune response to prophylactically or therapeutically treat a *Haemophilus influenzae* infection. In alternate embodiments, the vaccine is administered as several doses over a period of time, as a primary vaccination and "booster" vaccinations.

By "therapeutically effective amounts" herein is meant an amount of the HAP protein which is sufficient to induce an immune response. This amount may be different depending on whether prophylactic or therapeutic treatment is desired. Generally, this ranges from about 0.001 mg to about 1 gm. These amounts may be adjusted if adjuvants are used.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes.

EXAMPLES

Example 1

Cloning of the HAP protein

Bacterial Strains, plasmids, and phage. *H. influenzae* strain N187 is a clinical isolate that was originally cultivated from the middle ear fluid of a child with acute otitis media. This strain was classified as nontypable based on the absence of agglutination with typing antisera for *H. influenzae* types a–f (Burroughs Wellcome) and the failure to hybridize with pU038, a plasmid that contains the entire cap b locus (Kroll and Moxon, 1988, J. Bacteriol. 170:859–864).

*H. influenzae* strain DB117 is a red mutant of Rd, a capsule-deficient serotype d strain that has been in the laboratory for over 40 years (Alexander and Leidy, 1951, J. Exp. Med. 83:345–359); DB117 was obtained from G. Barcak (University of Maryland, Baltimore, Md.) (Sellow et al., 1968). DB117 is deficient for in vitro adherence and invasion, as assayed below.

*H. influenzae* strain 12 is the nontypable strain from which the genes encoding the HMW1 and HMW2 proteins were cloned (Barenkamp and Leininger, 1992, Infect. Immun. 60:1302–1313); HMW1 and HMW2 are the prototypic members of a family of nontypable Haemophilus antigenically-related high-molecular-weight adhesive proteins (St. Geme et al., 1993).

*E. coli* HB101, which is nonadherent and noninvasive, has been previously described (Sambrook et al., 1989, Molecular cloning: a laboratory manual, 2nd ed. Cold Spring Harbor Laboratory, Cold Spring Harbor, N.Y. ). *E. coli* DH5a was obtained from Bethesda Research Laboratories. *E. coli* MC1061 was obtained from H. Kimsey (Tufts University, Boston, Mass.). *E. coli* XL-1 Blue and the plasmid pBluescript KS- were obtained from Stratagene. Plasmid pT7-7 and phage mGP1-2 were provided by S. Tabor (Harvard Medical School, Boston, Mass.) (Tabor and Richardson, 1985, Proc. Natl. Acad. Sci. USA. 82:1074–1078). The *E. coli-Haemophilus* shuttle vector pGJB103 (Tomb et al., 1989, Rd. J. Bacteriol. 171:3796–3802) and phage λ1l05 (Way et al. , 1984, Gene. 32:3 69–379) were provided by G. Barcak (University of Maryland, Baltimore, Md.). Plasmid pVD116 harbors the IgA1 protease gene from *H. influenzae* strain Rd (Koomey and Falkow, 1984, Infect. Immun. 43:101–107) and was obtained from M. Koomey (University of Michigan, Ann Arbor, Mich.).

Growth conditions. *H. influenzae* strains were grown as described (Anderson et al., 1972, J. Clin. Invest. 51:31–38). They were stored at −80° C. in brain heart infusion broth with 25% glycerol. *E. coli* strains were grown on LB agar or in LB broth. They were stored at −80° C. in LB broth with 50% glycerol.

For *H. influenzae,* tetracycline was used in a concentration of 5 µg/ml and kanamycin was used in a concentration of 25 µg/ml. For *E. coli,* antibiotics were used in the following concentrations: tetracycline, 12.5 µg/ml; kanamycin, 50 µg/ml; ampicillin, 100 µg/ml.

Recombinant DNA methods. DNA ligations, restriction endonuclease digestions, and gel electrophoresis were performed according to standard techniques (Sambrook et al., 1989, supra). Plasmids were introduced into *E. coli* strains by either chemical transformation or electroporation, as described (Sambrook et al, 1989, supra; Dower et al., 1988, Nucleic Acids Res. 16:617–6145). In *H. influenzae* transformation was performed using the MIV method of Herriott et al. (1970, J. Bacteriol. 101:517–524), and electroporation was carried out using the protocol developed for *E. coli* (Dower et al., 1988, supra).

Construction of genomic library from *H. influenzae* strain N187. High-molecular-weight chromosomal DNA was prepared from 3 ml of an overnight broth culture of *H. influenzae* N187 as previously described (Mekalanos, 1983, Cell. 35:253–263). Following partial digestion with Sau3AI, 8 to 12 kb fragments were eluted into DEAE paper (Schleicher & Schuell, Keene, H. H.) and then ligated to BglII-digested calf intestine phosphatase-treated pGJB103. The ligation mixture was electroporated into *H. influenzae* DB117, and transformants were selected on media containing tetracycline.

Transposon mutagenesis.

Mutagenesis of plasmid DNA was performed using the mini-Tn10 kan element described by Way et al. (1984, supra). Initially, the appropriate plasmid was introduced into *E. coli* MC1061. The resulting strain was infected with λ1105, which carries the mini-Tn10 kan transposon. Transductants were grown overnight in the presence of kanamycin and an antibiotic to select for the plasmid, and plasmid DNA was isolated using the alkaline lysis method. In order to recover plasmids containing a transposon insertion, plasmid DNA was electroporated into *E. coli* DH5α, plating on media containing kanamycin and the appropriate second antibiotic.

In order to establish more precisely the region of pN187 involved in promoting interaction with host cells, initially this plasmid was subjected to restriction endonuclease analysis. Subsequently, several subclones were constructed in the vector pGJB103 and were reintroduced into *H. influenzae* strain DB117. The resulting strains were then examined for adherence and invasion. As summarized in FIG. 4, subclones containing either a 3.9-kb PstI-BglII fragment (pJS105) or the adjoining 4.2-kb BglII fragment (pJS102) failed to confer the capacity to associate with Chang cells. In contrast, a subclone containing an insert that included portions of both of these fragments (pJS106) did promote interaction with epithelial monolayers. Transposon mutagenesis performed on pH187 confirmed that the flanking portions of the insert in this plasmid were not required for the adherent/invasive phenotype. On the other hand, a transposon insertion located adjacent to the BgIII site in pJS106 eliminated adherence and invasion. An insertion between the second EcoRI and PstI sites in this plasmid had a similar effect (FIG. 4).

Examination of plasmid-encoded proteins.

In order to examine plasmid encoded proteins, relevant DNA was ligated into the bacteriophage T7 expression vector pT7-7, and the resulting construct was transformed into *E. coli* XL-1 Blue. Plasmid pT7-7 contains the T7 phage φ10 promoter and ribosomal binding site upstream of a multiple cloning site (Tabor and Richardson, 1985, supra). The T7 promoter was induced by infection with the recombinant M13 phage mGP1-2 and addition of isopropyl-β-D-thiogalactopyranoside (final concentration, 1 mM). Phage mGP1-2 contains the gene encoding T7 RNA polymerase, which activates the φ10 promoter in pT7-7 (Tabor and Richardson, 1985, supra).

Like DB117(pN187), strain DB117 carrying pJS106 expressed new outer membrane proteins 160-kD and 45-kD in size (FIG. 3, lane 3). In order to examine whether the 6.5-kb insert in pJS106 actually encodes these proteins, this fragment of DNA was ligated into the bacteriophage T7 expression vector pT7-7. The resulting plasmid containing the insert in the same orientation as in pN187 was designated pJS104, and the plasmid with the insert in the opposite orientation was designated pJS103. Both pJS104, and p7S103 were introduced into *E. coli* XL-1 Blue, producing XL-1 Blue(pJS104) and XL-1 Blue(pJS103), respectively. As a negative control, pT7-7 was also transformed into XL-1 Blue. The T7 promoter was induced in these three strains by infection with the recombinant M13 phage mGP1-2 and addition of isopropyl-β-D-thiogalactopyranoside (final concentration, 1 mM), and induced proteins were detected using [$^{35}$S] methionine. As shown in FIG. 5, induction of XL-1 Blue(pJS104) resulted in expression of a 160-kD protein and several smaller proteins which presumably represent degradation products. In contrast, when XL-1 Blue (pJS103) and XL-1 Blue(pT7-7) were induced, there was no expression of these proteins. There was no 45-kD protein induced in any of the three strains. This experiment suggested that the 6.5-kb insert present in pJS106 contains the structural gene for the 160-kD outer membrane protein identified in DB117(pJS106). On the other hand, this analysis failed to establish the origin of the 45-kD membrane protein expressed by DB117(pJS106).

Adherence and invasion assays.

Adherence and invasion assays were performed with Chang epithelial cells [Wong-Kilbourne derivative, clone 1-5c-4 (human conjunctiva)], which were seeded into wells of 24-well tissue culture plates as previously described (St. Geme and Falkow, 1990). Adherence was measured after incubating bacteria with epithelial monolayers for 30 minutes as described (St. Geme et al., 1993). Invasion assays were carried out according to our original protocol and involved incubating bacteria with epithelial cells for four hours followed by treatment with gentamicin for two hours (100 μg/ml) (St. Geme and Falkow, 1990).

Nucleotide sequence determination and analysis.

Nucleotide sequence was determined using a Sequenase kit and double stranded plasmid template. DNA fragments were subcloned into pBluescript KS and sequenced along both strands by primer walking. DNA sequence analysis was performed using the Genetics Computer Group (GCG) software package from the University of Wisconsin (Devereux et al., 1984). Sequence similarity searches were carried out using the BLAST program of the National Center for Biotechnology Information (Altschul et al., 1990, J. Mol. Biol. 215:403–410). The DNA sequence described here will be deposited in the EMBL/GenBank/DDBJ Nucleotide Sequence Data Libraries.

Based on the our subcloning results, we reasoned that the central BglII site in pH187 was positioned within an open reading frame. Examination of a series of mini-Tn10 kan mutants supported this conclusion (FIG. 4). Consequently, we sequenced DHA on either side of this BglII site and identified a 4182 bp gene, which we have designated hap for Haemophilus adherence and penetration (FIG. 6). This gene encodes a 1394 amino acid polypeptide, which we have called Hap, with a calculated molecular mass of 155.4-kD, in good agreement with the molecular mass of the larger of the two novel outer membrane proteins expressed by DB117 (pN187) and the protein expressed after induction of XL-1 Blue/pJS104. The hap gene has a G+C content of 39.1%, similar to the published estimate of 38.7% for the whole genome (Kilian, 1976, J. Gen. Microbiol. 93:9–62). Putative −10 and −35 promoter sequences are present upstream of the initiation codon. A consensus ribosomal binding site is lacking. A sequence similar to a rho-independent transcription terminator is present beginning 39 nucleotides beyond the stop codon and contains interrupted inverted repeats with the potential for forming a hairpin structure containing a loop of three bases and a stem of eight bases. Similar to the situation with typical E coli terminators, this structure is followed by a stretch rich in T residues. Analysis of the predicted amino acid sequence suggested the presence of a 25 amino acid signal peptide at the amino terminus. This region has characteristics typical of procaryotic signal peptides, with three positive H-terminal charges, a central hydrophobic region, and alanine residues at positions 23 and 25 (−3 and −1 relative to the putative cleavage site) (von Heijne, 1984, J. Mol. Biol. 173:243–251).

Comparison of the deduced amino acid sequence of Hap with other proteins. A protein sequence similarity search was performed with the predicted amino acid sequence using the BLAST network service of the National Center for Biotechnology Information (Altschul et al., 1990, supra). This search revealed homology with the IgA1 proteases of *H. influenzae* and *Neisseria gonorrhoeae*. Alignment of the derived amino acid sequences for the hap gene product and the IgA1 proteases from four different *H. influenzae* strains revealed homology across the extent of the proteins (FIG. 7), with several stretches showing 55–60% identity and 70–80% similarity. Similar levels of homology were noted between the hap product and the IgA1 protease from N. gonorrhoeae strain MS11. This homology includes the region identified as the catalytic site of the IgA1 proteases, which is comprised of the sequence GDSGSPLF, (SEQ ID NO:8) where 2 is the active site serine characteristic of serine proteases (Brenner, 1988, Nature (London). 334:528–530; Poulsen et al., 1992, J. Bacteriol. 174:2913–2921). In the case of Hap, the corresponding sequence is GDSGSPMF (SEQ ID NO:7). The hap product also contains two cysteines corresponding to the cysteines proposed to be important in forming the catalytic domain of the IgA proteases (Pohlner et al., 1987, supra). Overall there is 30–35% identity and 51–55% similarity between the hap gene product and the *H. influenzae* and *N. gonorrhoeae* IgA proteases.

The deduced amino acid sequence encoded by hap was also found to contain significant homology to Tsh, a hemagglutinin expressed by an avian *E. coli* strain (Provence and Curtiss, 1994, supra). This homology extends throughout both proteins but is greatest in the H-terminal half of each. Overall the two proteins are 30.5% identical and 51.6% similar. Tsh is also synthesized as a preprotein and is secreted as a smaller form; like the IgA1 proteases and perhaps Hap, a carboxy terminal peptide remains associated with the outer membrane (D. Provence, personal communication). While this protein is presumed to have proteolytic activity, its substrate has not yet been determined. Interestingly, Tsh was first identified on the basis of its capacity to promote agglutination of erythrocytes. Thus Hap and Tsh are possibly the first members of a novel class of adhesive proteins that are processed analogously to the IgA1 proteases.

Homology was also noted with pertactin, a 69-kD outer membrane protein expressed by *B. pertussis* (Charles et al., 1989, Proc. Natl. Acad. Sci. USA. 86:3554–3558). The middle portions of these two molecules are 39% identical and nearly 60% similar. This protein contains the amino acid triplet arginine-glycine-aspartic acid (RGD) and has been shown to promote attachment to cultured mammalian cells via this sequence (Leininger et al., 1991, Proc. Natl. Acad. Sci. USA. 88:345–349). Although Bordetella species are not generally considered intracellular parasites, work by Ewanowich and coworkers indicates that these respiratory pathogens are capable of in vitro entry into human epithelial cells (Ewanowich et al., 1989, Infect. Immun. 57:2698–2704; Ewanowich et al., 1989, Infect. Immun. 57:1240–1247). Recently Leininger et al. reported that preincubation of epithelial monolayers with an RGD-containing peptide derived from the pertactin sequence specifically inhibited B. pertussis entry (Leininger et al., 1992, Infect. Immun. 60:2380–2385). In addition, these investigators found that coating of Staphylococcus aureus with purified pertactin resulted in more efficient S. aureus entry; the RGD-containing peptide from pertactin inhibited this pertactin-enhanced entry by 75%. Although the hap product lacks an RGD motif, it is possible that Hap and pertactin serve similar biologic functions for H. influenzae and Bordetella species, respectively.

Additional analysis revealed significant homology (34 to 52% identity, 42 to 70% similarity) with six regions of HpmA, a calcium-independent hemolysin expressed by Proteus mirabilis (Uphoff and Welch, 1990, supra).

The hap locus is distinct from the H. influenzae IgA1 protease gene.

Given the degree of similarity between the hap gene product and H. influenzae IgA1 protease, we wondered whether we had isolated the IgA1 protease gene of strain N187. To examine this possibility, we performed IgA1 protease activity assays. Among H.influenzae strains, two enzymatically distinct types of IgA1 protease have been found (Mulks et al., 1982, J. Infect. Dis. 146:266–274). Type 1 enzymes cleave the Pro-Ser peptide bond between residues 231 and 232 in the hinge region of human IgA1 heavy chain and generate fragments of roughly 28-kD and 31-kD; type 2 enzymes cleave the Pro-Thr bond between residues 235 and 236 in the hinge region and generate 26.5-kD and 32.5-kD fragments. Previous studies of the parent strain from which DB117 was derived have demonstrated that this strain produces a type 1 IgA1 protease (Koomey and Falkow, 1984, supra). As shown in FIG. 8, comparison of the proteolytic activities of strain DB117 and strain N187 suggested that N187 produces a type 2 IgA1 protease. We reasoned that DB117(pN187) might generate a total of four fragments from IgA1 protease, consistent with two distinct cleavage specificities. Examination of DB117(pH187) revealed instead that this transformant produces the same two fragments of the IgA1 heavy chain as does DB117, arguing that this strain produces only a type 1 enzyme.

In an effort to obtain additional evidence against the possibility that plasmid pH187 contains the N187 IgA1 protease gene, we performed a series of Southern blots. As shown in FIG. 9, when genomic DNA from strain N187 was digested with EcoRI, BglII, or BamHI and then probed with the hap gene, one set of hybridizing fragments was detected. Probing of the same DNA with the iga gene from H. influenzae strain Rd resulted in a different set of hybridizing bands. Moreover, the iga gene failed to hybridize with a purified 4.8-kb fragment that contained the intact hap gene.

The recombinant plasmid associated with adherence and invasion encodes a secreted protein.

The striking homology between the hap gene product and the Haemophilus and Neisseria IgA1 proteases suggested the possibility that these proteins might be processed in a similar manner. The IgA1 proteases are synthesized as preproteins with three functional domains: the N-terminal signal peptide, the protease, and a C-terminal helper domain, which is postulated to form a pore in the outer membrane for secretion of the protease (Poulsen et al., 1989, supra; Pohlner et al., 1987, supra). The C-terminal peptide remains associated with the outer membrane following an autoproteolytic cleavage event that results in release of the mature enzyme. Consistent with the possibility that the hap gene product follows a similar fate, we found that DB117(pN187) produced a secreted protein approximately 110-kD in size that was absent from DB117(pGJB103) (FIG. 10). This protein was also produced by DB117(pJS106), but not by DB117(pJ5102) or DB117(pJS105). Furthermore, the two mutants with transposon insertions within the hap coding region were deficient in this protein. In order to determine the relationship between hap and the secreted protein, this protein was transferred to a PVDF membrane and N-terminal amino acid sequencing was performed. Excessive background on the first cycle precluded identification of the first amino acid residue of the free amino terminus. The sequence of the subsequent seven residues was found to be HTYFGID, (SEQ ID NO:9) which corresponds to amino acids 27 through 33 of the hap product.

The introduction of hap into laboratory strains of E. coli strains was unable to endow these organisms with the capacity for adherence or invasion. In considering these results, it is noteworthy that the E. coli transformants failed to express either the 160-kD or the 45-kD outer membrane protein. Accordingly, they also failed to express the 110-kD secreted protein. The explanation for this lack of expression is unclear. One possibility is that the H. influenzae promoter or ribosomal binding site was poorly recognized in E. coli. Indeed the putative −35 sequence upstream of the hap initiation codon is fairly divergent from the δ70 consensus sequence, and the ribosomal binding site is unrecognizable. Alternatively, an accessory gene may be required for proper export of the Hap protein, although the striking homology with the IgA proteases, which are normally expressed and secreted in E. coli, argues against this hypothesis.

In considering the possibility that the hap gene product promotes adherence and invasion by directly binding to a host cell surface structure, it seems curious that the mature protein is secreted from the organism. However, there are examples of other adherence factors that are also secreted. Filamentous hemagglutinin is a 220-kD protein expressed by B. pertussis that mediates in vitro adherence and facilitates natural colonization (Relman et al., 1989, Proc. Natl. Acad. Sci. U.S.A. 86:2637–2641; Kimura et al. , 1990, Infect. Immun. 58:7–16). This protein remains surface-associated to some extent but is also released from the cell. The process of Filamentous hemagglutinin secretion involves an accessory protein designated FhaC, which appears to be localized to the outer membrane (Willems et al., 1994, Molec. Microbiol. 11:337–347). Similarly, the Ipa proteins implicated in Shigella invasion are also secreted. Secretion of these proteins requires the products of multiple genes within the mxi and spa loci (Allaoui et al., 1993, Molec. Microbiol. 7:59–68; Andrews et al., 1991, Infect. Immun. 59:1997–2005; Venkatsan et al., 1992, J. Bacteriol. 174:1990–2001).

It is conceivable that secretion is simply a consequence of the mechanism for export of the hap gene product to the surface of the organism. However, it is noteworthy that the secreted protein contains a serine-type protease catalytic domain and shows homology with the P. mirobilis hemolysin. These findings suggest that the mature Hap protein may possess proteolytic activity and raise the possibility that Hap promotes interaction with the host cell at a distance by modifying the host cell surface. Alternatively, Hap may modify the bacterial surface in order to facilitate interaction with a host cell receptor. It is possible that hap encodes a molecule with dual functions, serving as both adhesin and protease.

Analysis of outer membrane and secreted proteins.

Outer membrane proteins were isolated on the basis of sarcosyl insolubility according to the method of Carlone et al. (1986, J. Clin. Microbiol. 24:330–332). Secreted proteins were isolated by centrifuging bacterial cultures at 16,000 g for 10 minutes, recovering the supernatant, and precipitating with trichloroacetic acid in a final concentration of 10%. SDS-polyacrylamide gel electrophoresis was performed as previously described (Laemmli, 1970, Nature (London). 227:680–685).

To identify proteins that might be involved in the interaction with the host cell surface, outer membrane protein profiles for DB117(pN187) and DB117(pGJB103) were compared. As shown in FIG. 3, DB117(pN187) expressed two new outer membrane proteins: a high-molecular-weight protein approximately 160-kD in size and a 45-kD protein. E. coli HB101 harboring pN187 failed to express these proteins, suggesting an explanation for the observation that HB100(pN187) is incapable of adherence or invasion.

Previous studies have demonstrated that a family of antigenically-related high-molecular-weight proteins with similarity to filamentous hemagglutinin of Bordetella pertussis mediate attachment by nontypable H. influenzae to cultured epithelial cells (St. Geme et al., 1993). To explore the possibility that the gene encoding the strain H187 member of this family was cloned, whole cell lysates of N187, DB117(pN187), and DB117 (pGJB103) were examined by Western immunoblot. our control strain for this experiment was H. influenzae strain 12. Using a polyclonal antiserum directed against HMW1 and HMW2, the prototypic proteins in this family, we identified a 140-kD protein in strain H187 (not shown). In contrast, this antiserum failed to react with either DB117(pN187) or DB117(pGJB103) (not shown), indicating that pN187 has no relationship to HMW protein expression.

Determination of amino terminal sequence. Secreted proteins were precipitated with trichloroacetic acid, separated on a 10% SDS-polyacrylamide gel, and electrotransferred to a polyvinylidene difluoride (PVDF) membrane (Matsudaira, 1987, J. Biol. Chem. 262:10035–10038). Following staining with Coomassie Brilliant Blue R-250, the 110-kD protein was cut from the PVDF membrane and submitted to the Protein Chemistry Laboratory at Washington University School of Medicine for amino terminal sequence determination. Sequence analysis was performed by automated Edman degradation using an Applied Biosystems Model 470A protein sequencer.

Examination of IgA1 protease activity. In order to assess IgA1 protease activity, bacteria were inoculated into broth and grown aerobically overnight. Samples were then centrifuged in a microphage for two minutes, and supernatants were collected. A 10 $\mu$l volume of supernatant was mixed with 16 $\mu$l of 0.5 $\mu$g/ml human IgA1 (Calbiochem), and chloramphenicol was added to a final concentration of 2 $\mu$g/ml. After overnight incubation at 37° C., reaction mixtures were electrophoresed on a 10% SDS-polyacrylamide gel, transferred to a nitrocellulose membrane, and probed with goat anti-human IgA1 heavy chain conjugated to alkaline phosphatase (Kirkegaard & Perry). The membrane was developed by immersion in phosphatase substrate solution (5-bromo-4-chloro-3-indolylphosphate toluidinium-nitro blue tetrazolium substrate system; Kirkegaard & Perry).

Immunoblot analysis. Immunoblot analysis of bacterial whole cell lysates was carried out as described (St. Geme et al., 1991).

Southern hybridization. Southern blotting was performed using high stringency conditions as previously described (St. Geme and Falkow, 1991).

Microscopy.

i. Light microscopy. Samples of epithelial cells with associated bacteria were stained with Giemsa stain and examined by light microscopy as described (St. Geme and Falkow, 1990).

ii. Transmission electron microscopy. For transmission electron microscopy, bacteria were incubated with epithelial cell monolayers for four hours and were then rinsed four times with PBS, fixed with 2% glutaraldehyde/1% osmium tetroxide in 0.1 M sodium phosphate buffer pH 6.4 for two hours on ice, and stained with 0.25% aqueous uranyl acetate overnight. Samples were then dehydrated in graded ethanol solutions and embedded in polybed. Ultrathin sections (0.4 $\mu$m) were examined in a Phillips 201c electron microscope.

As shown in FIG. 2, DB117(pN187) incubated with monolayers for four hours demonstrated intimate interaction with the epithelial cell surface and was occasionally found to be intracellular. In a given thin section, invaded cells generally contained one or two intracellular organisms. Of note, intracellular bacteria were more common in sections prepared with strain N187, an observation consistent with results using the gentamicin assay. In contrast, examination of samples prepared with strain DB117 carrying cloning vector alone (pGJB103) failed to reveal internalized bacteria (not shown).

Having described the preferred embodiments of the present invention it will appear to those of ordinary skill in the art that various modifications may be made to the disclosed embodiments, and that such modifications are intended to be within the scope of the present invention.

What is claimed is:

1. A recombinant Haemophilus adhesion and penetration protein encoded by a nucleic acid, which nucleic acid will hybridize under high stringency conditions to a nucleic acid having a sequence as shown in SEQ ID NO:1.

2. A recombinant Haemophilus adhesion and penetration protein which has an amino acid sequence as shown in SEQ ID NO:2.

3. A composition comprising a pharmaceutically acceptable carrier and a Haemophilus adhesion and penetration protein according to claim 1 or 2.

4. A method of treating a patient comprising administering the composition of claim 3, wherein said Haemophilus adhesion and penetration protein shares at least one epitope or determinant with the 160 kD, 110 kD or 45 kD Haemophilus adhesion and penetration protein of *H. influenzae*, wherein said composition is in an amount which is effective for the therapeutic or prophylactic treatment of Haemophilus.

5. A method of inducing an immune response in a patient comprising the step of, administering to said patient the composition of claim 3, wherein said composition is in an amount which is effective to induce an immune response.

* * * * *